(12) United States Patent
John et al.

(10) Patent No.: US 11,045,427 B2
(45) Date of Patent: Jun. 29, 2021

(54) HOLLOW NANOPARTICLES WITH HYBRID DOUBLE LAYERS

(71) Applicant: THE ADMINISTRATORS OF THE TULANE EDUCATIONAL FUND, New Orleans, LA (US)

(72) Inventors: Vijay John, Destrehan, LA (US); Gary McPherson, Mandeville, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 15/695,387

(22) Filed: Sep. 5, 2017

(65) Prior Publication Data
US 2018/0071225 A1   Mar. 15, 2018

Related U.S. Application Data

(62) Division of application No. 14/378,921, filed as application No. PCT/US2013/026745 on Feb. 19, 2013, now abandoned.
(Continued)

(51) Int. Cl.
*A61K 9/50* (2006.01)
*C09B 61/00* (2006.01)
(Continued)

(52) U.S. Cl.
CPC ............ *A61K 9/5089* (2013.01); *A61K 9/501* (2013.01); *A61K 9/5094* (2013.01); *A61K 9/51* (2013.01);
(Continued)

(58) Field of Classification Search
None
See application file for complete search history.

(56) References Cited

U.S. PATENT DOCUMENTS

| | | |
|---|---|---|
| 2003/0181535 A1 | 9/2003 | Van Hardeveld et al. |
| 2009/0178589 A1 | 7/2009 | Yoneyama |
| 2010/0056366 A1* | 3/2010 | Lee .................. B01J 21/063 |
| | | 502/300 |

FOREIGN PATENT DOCUMENTS

| | | |
|---|---|---|
| EA | 009837 B1 | 4/2008 |
| RU | 2366501 C1 | 9/2009 |

OTHER PUBLICATIONS

Ikeda et al. "Selective adsorption of glucose-derived carbon precursor on amino-functionalized porous silica for fabrication of hollow carbon sphere with porous walls", Chem Mter., 2007 19, 4335-4340. (Year: 2007) (Year: 2007).*

(Continued)

*Primary Examiner* — Isis A Ghali
(74) *Attorney, Agent, or Firm* — Marshall, Gerstein & Borun LLP

(57) ABSTRACT

The present invention discloses the morphology of hollow, double-shelled submicrometer particles generated through a rapid aerosol-based process. The inner shell is an essentially hydrophobic carbon layer of nanoscale dimension (5-20 nm), and the outer shell is a hydrophilic silica layer of approximately 5-40 nm, with the shell thickness being a function of the particle size. The particles are synthesized by exploiting concepts of salt bridging to lock in a surfactant (CTAB) and carbon precursors together with iron species in the interior of a droplet. This deliberate negation of surfactant templating allows a silica shell to form extremely rapidly, sealing in the organic species in the particle interior. Subsequent pyrolysis results in a buildup of internal pressure, forcing carbonaceous species against the silica wall to form an inner shell of carbon. The incorporation of magnetic iron oxide into the shells opens up applications in external stimuli-responsive nanomaterials.

20 Claims, 32 Drawing Sheets

Related U.S. Application Data

(60) Provisional application No. 61/599,788, filed on Feb. 16, 2012, provisional application No. 61/610,798, filed on Mar. 14, 2012, provisional application No. 61/621,642, filed on Apr. 9, 2012.

(51) Int. Cl.

| | |
|---|---|
| *C09B 67/08* | (2006.01) |
| *C09B 11/24* | (2006.01) |
| *B82Y 30/00* | (2011.01) |
| *B01J 21/06* | (2006.01) |
| *B01J 35/00* | (2006.01) |
| *C09C 1/40* | (2006.01) |
| *C09C 1/24* | (2006.01) |
| *C09C 1/30* | (2006.01) |
| *C09C 1/36* | (2006.01) |
| *B01J 13/22* | (2006.01) |
| *B01J 23/745* | (2006.01) |
| *B01J 13/14* | (2006.01) |
| *C09B 67/02* | (2006.01) |
| *A61K 9/51* | (2006.01) |
| *B01J 21/18* | (2006.01) |
| *H01M 4/36* | (2006.01) |
| *H01M 4/587* | (2010.01) |
| *H01M 4/86* | (2006.01) |
| *B01J 35/02* | (2006.01) |
| *B01J 35/10* | (2006.01) |
| *B01J 37/00* | (2006.01) |
| *B01J 37/08* | (2006.01) |
| *H01M 4/90* | (2006.01) |
| *H01M 10/0525* | (2010.01) |
| *H01M 10/052* | (2010.01) |
| *H01G 9/20* | (2006.01) |
| *B82Y 40/00* | (2011.01) |

(52) U.S. Cl.
CPC .............. *A61K 9/5192* (2013.01); *B01J 13/14* (2013.01); *B01J 13/22* (2013.01); *B01J 21/063* (2013.01); *B01J 21/18* (2013.01); *B01J 23/745* (2013.01); *B01J 35/002* (2013.01); *B01J 35/004* (2013.01); *B01J 35/0013* (2013.01); *B01J 35/0033* (2013.01); *B01J 35/023* (2013.01); *B01J 35/026* (2013.01); *B01J 35/1057* (2013.01); *B01J 35/1061* (2013.01); *B01J 35/1066* (2013.01); *B01J 37/0072* (2013.01); *B01J 37/08* (2013.01); *B82Y 30/00* (2013.01); *C09B 11/24* (2013.01); *C09B 61/00* (2013.01); *C09B 67/0008* (2013.01); *C09B 67/0097* (2013.01); *C09C 1/24* (2013.01); *C09C 1/30* (2013.01); *C09C 1/3607* (2013.01); *C09C 1/407* (2013.01); *H01M 4/366* (2013.01); *H01M 4/587* (2013.01); *H01M 4/8605* (2013.01); *H01M 4/8657* (2013.01); *H01M 4/9041* (2013.01); *H01M 10/0525* (2013.01); *B82Y 40/00* (2013.01); *C01P 2002/72* (2013.01); *C01P 2004/03* (2013.01); *C01P 2004/04* (2013.01); *C01P 2004/34* (2013.01); *C01P 2004/62* (2013.01); *C01P 2004/64* (2013.01); *C01P 2006/12* (2013.01); *C01P 2006/14* (2013.01); *C01P 2006/16* (2013.01); *C01P 2006/62* (2013.01); *H01G 9/2031* (2013.01); *H01M 10/052* (2013.01)

(56) References Cited

OTHER PUBLICATIONS

Tartaj et al. "The preparation of magnetic nanoparticles for application in biomedicine", J.Phys. D: Appl. Phys. 36 R-182-197. (Year: 2003).*

Agarawal et al., Microstructure evolution in aqueous solutions of cetyl trimethylammonium bromide (CTAB) and phenol derivatives, Colloids and Surfaces A: Physicochemical and Engineering Aspects, 281(1-3):246-53 (Jun. 2006).

Beck et al., A new family of mesoporous molecular sieves prepared with liquid crystal templates, J. Am. Chem. Soc., 114(27):10834-43 (1992).

Binks et al., Catastrophic Phase Inversion of Water-in-Oil Emulsions Stabilized by Hydrophobic Silica. Langmuir, 16(6):2539-47 (2000).

Binks et al., Colloidal Particles at Liquid Interfaces. Cambridge University Press (2006).

Binks et al., Influence of Particle Wettability on the Type and Stability of Surfactant-Free Emulsions. Langmuir, 16(23):8622-31 (2000).

Binks et al., Optical Microscope Absorbance Imaging of Carbon Black Nanoparticle Films at Solid and Liquid Surfaces. Langmuir, 22(4):1664-70 (2006).

Binks et al., Particles as surfactants-similarities and differences. Current Opinion in Colloid & Interface Science, 7(1-2):21-41 (2002).

Binks et al., Phase inversion of particle-stabilized materials from foams to dry water, Nature Materials, 5(11):865-9 (2006).

Binks et al., Silica Particle-Stabilized Emulsions of Silicone Oil and Water: Aspects of Emulsification. Langmuir, 20(4):1130-7 (2004).

Binks et al., tability of oil-in-water emulsions stabilised by silica particles. Physical Chemistry Chemical Physics, 1(12):3007-16 (1999).

Binks et al., Types of Phase Inversion of Silica Particle Stabilized Emulsions Containing Triglyceride Oil. Langmuir, 19(12):4905-12 (2003).

Boissiere et al., Aerosol route to functional nanostructured inorganic and hybrid porous materials, Adv. Mater., 23:599-623 (2011).

Brunauer et al., On a Theory of the van der Waals Adsorption of Gases, J. Am. Chem. Soc., 62(7):1723-32 (1940).

Cao et al., Microwave-assisted gas/liquid interfacial synthesis of flowerlike NiO hollow nanosphere precursors and their application as supercapacitor electrodes, J. Mater. Chem., 21:3204-9 (2011).

Chen et al., Porous Silica Nanocapsules and Nanospheres: Dynamic Self-Assembly Synthesis and Application in Controlled Release, Chem. Mater., 20(18):5894-900 (2008).

Choi et al., Highly Durable Graphene Nanosheet Supported Iron Catalyst for Oxygen Reduction Reaction in PEM Fuel Cells, J. The Electrochemical Soc., 159(1):B87 (Jan. 2012).

Cornelissen et al., Versatile synthesis of nanometer sized hollow silica spherest, Chem. Commun. (Camb.), (8):1010-1 (Apr. 2003).

Crossley et al., Solid Nanoparticles that Catalyze Biofuel Upgrade Reactions at the Water/Oil Interface. Science, 327(5961):68-72 (2010).

Dai et al., Self-Assembled Structure of Nanoparticles at a Liquid-Liquid Interface. Langmuir, 21(7):2641-3 (2005).

Ding et al., Formation of $SnC>2$ hollow nanospheres inside mesoporous silica nanoreactors. J. Am. Chem. Soc., 133:21-3 (2011).

Dinsmore et al., Colloidosomes: Selectively Permeable Capsules Composed of Colloidal Particles. Science, 298(5595):1006-9 (2002).

Dong et al., Accurate Control of Multishelled ZnO Hollow Microspheres for Dye-Sensitized Solar Cells with High Efficiency, Adv. Mater., 24(8):1046-9 (Feb. 2012).

Drelich et al., Evolution of water-in-oil emulsions stabilized with solid particles: Influence of added emulsifier. Colloids and Surfaces A: Physicochemical and Engineering Aspects, 365:(1-3):171-7 (2010).

Flint et al., The Temperature of Cavitation, Science, 253(5026):1397-9 (Sep. 1991).

(56) References Cited

OTHER PUBLICATIONS

Frelichowska et al., Pickering emulsions with bare silica. Colloids and Surfaces A: Physicochemical and Engineering Aspects, 343(1-3):70-4 (2009).
Frelichowska et al., Topical delivery of lipophilic drugs from o/w Pickering emulsions. International Journal of Pharmaceutics 371(1-2):56-63 (2009).
Fritz et al., Evaluation of small-angle scattering data of charged particles using the generalized indirect Fourier transformation technique, J. Chem. Phys., 113:9733 (2000).
Fritz et al., Structure and interaction in dense colloidal systems: evaluation of scattering data by the generalized indirect Fourier transformation method, J. Phys.: Condens. Matter, 18:S2403 (2006).
Fujiwara et al., Direct encapsulation of BSA and DNA into silica microcapsules (hollow spheres), J. Biomed. Mater. Res. A, 81(1):103-12 (Apr. 2007).
Gao et al., FePt@CoS2 Yolk-Shell Nanocrystals as a Potent Agent to Kill HeLa Cells, J. Am. Chem. Soc., 129(5):1428-33 (2007).
Ge et al., Synthesis of porous hollow silica spheres using polystyrene-methyl acrylic acid latex template at different temperatures, J. Physics Chem. Solids, 70(11):1432-7 (Nov. 2009).
Glatter et al., Determination of particle-size distribution functions from small-angle scattering data by means of the indirect transformation method, J. Applied Crystallography, 13(1):7-11 (Feb. 1980).
Glatter et al., Elastic light scattering from nonspherical and polydisperse particles in the size range from 100 to 2000 NM, Makromolekulare Chemie. Macromolecular Symposia banner, 15(1):191-200 (Mar. 1988).
Glatter et al., Interpretation of elastic light scattering data in real space: II. Nonspherical and inhomogeneous monodisperse systems, J. Colloid and Interface Science, 122(2):484-95 (Apr. 1988).
Glatter et al., Interpretation of elastic light scattering data: III. Determination of size distributions of polydisperse systems, J. Colloid and Interface Science, 122(2):496-506 (Apr. 1988).
Glatter, Comparison of two different methods for direct structure analysis from small-angle scattering data, J. Applied Crystallography, 21(6):886-90 (Dec. 1988).
Glatter, Evaluation of small-angle scattering data from lamellar and cylindrical particles by the indirect transformation method, J. Applied Crystallography, 13(6):577-84 (Dec. 1980).
Graf et al., Metallodielectric Colloidal Core-Shell Particles for Photonic Applications, Langmuir, 18(2):524-34 (2002).
Guo et al., Highly catalytic activity of Pt electrocatalyst supported on sulphated SnO(2)/multi-walled carbon nanotube composites for methanol electro-oxidation, J. Power Sources, 198:127-31 (Jan. 2012).
Guo et al., Hollow graphene oxide spheres self-assembled by W/O emulsion. Journal of Materials Chemistry, 20(23):4867-74 (2010).
He et al., An efficient reduction route for the production of Pd—Pt nanoparticles anchored on graphene nanosheets for use as durable oxygen reduction electrocatalysts, Carbon, 50(1):265-74 (Jan. 2012).
Hentze et al., Silica hollow spheres by templating of catanionic vesicles. Langmuir, 19(4), 1069-1074 (2003).
Horikoshi et al., On the stability of surfactant-free water-in-oil emulsions and synthesis of hollow SiO2 nanospheres. Colloids and Surfaces A: Physicochemical and Engineering Aspects, 372(1-3):55-60 (2010).
Hosseini et al., Preparation of a nanocomposite of magnetic, conducting nanoporous polyaniline and hollow manganese ferrite, Polymer Journal, 43(9):745-50 (Jul. 2011).
Hsu et al., The use of carbon nanotubes coated with a porous nitrogen-doped carbon layer with embedded Pt for the methanol oxidation reaction, J. Power Sources, 198:83-9 (2012).
Im et al., Polymer hollow particles with controllable holes in their surfaces, Nat. Mater., 4:671-5 (2005).
International Application No. PCT/US2013/026745, International Search Report and Written Opinion, dated Jun. 27, 2013.
Jiang et al., Ultrasonic synthesis of nitrogen-doped carbon nanofibers as platinum catalyst support for oxygen reduction. Journal of Power Sources 2011, 196, (22), 9356-9360.

Jin et al., The Preparation of Monodisperse Cationic Polystyrene and its Application to the Synthesis of Hollow Silica Spheres, Australian J. Chem., 63(10):1418-22 (Oct. 2010).
Jin et al., Titanium Containing ?-MnO2 (TM) Hollow Spheres: One-Step Synthesis and Catalytic Activities in Li/Air Batteries and Oxidative Chemical Reactions, Adv. Functional Mater., 20(19):3373-82 (Oct. 2010).
Jing et al., Ultrasound-triggered smart drug release from multifunctional core-shell capsules one-step fabricated by coaxial electrospray method, Langmuir, 27(3):1175-80 (Feb. 2011).
Katoch et al., Preparation of highly stable TiO(2) sols and nanocrystalline TiO(2) films via a low temperature sol-gel route, J. Sol-Gel Science and Technology, 61(1):77-82 (2012).
Kim et al., Fabrication of hollow palladium spheres and their successful application to the recyclable heterogeneous catalyst for suzuki coupling reactions, J. Am. Chem. Soc., 124(26):7642-3 (Jul. 2002).
Kim et al., Ultrasound-Triggered Smart Drug Release from a Poly(dimethylsiloxane)-Mesoporous Silica Composite, 18(23):3083-8 (Dec. 2006).
Kim et al., Ultrastable mesostructured silica vesicles, Science, 282(5392):1302-5 (Nov. 1998).
Kresge et al., Ordered mesoporous molecular sieves synthesized by a liquid-crystal template mechanism, Nature, 359:710-2 (1992).
Lai et al., General Synthesis and Gas-Sensing Properties of Multiple-Shell Metal Oxide Hollow Microspheres, Angew. Chem. Int. Ed., 50(12):2738-41 (Mar. 2011).
Lai et al., Recent advances in micro-/nano-structured hollow spheres for energy applications: From simple to complex systems, Energy Environ. Sci., 5:5604-18 (2012).
Lee et al., Advanced fabrication of metal-organic frameworks: template-directed formation of polystyrene@ZIF-8 core-shell and hollow ZIF-8 microspheres, Chem. Commun. (Camb.), 48(2):221-3 (Jan. 2012).
Lei et al., Growth of Polyaniline on Hollow Carbon Spheres for Enhancing Electrocapacitance, J. Phys. Chem. C, 114(46):1986774 (2010).
Li et al., Highly sensitive WO3 hollow-sphere gas sensors, Inorg. Chem., 43(17):5442-9 (Aug. 2004).
Li et al., Polymer replicas of photonic porous silicon for sensing and drug delivery applications, Science, 299(5615):2045-7 (Mar. 2003).
Liang et al., Pt hollow nanospheres: facile synthesis and enhanced electrocatalysts, Angew. Chem. Int. Ed. Engl., 43(12):1540-3 (Mar. 2004).
Liu et al., A simple approach to the synthesis of hollow microspheres with magnetite/silica hybrid walls, J. Colloid Interface Sci., 333(1):329-34 (May 2009).
Liu et al., Yolk-Shell Hybrid Materials with a Periodic Mesoporous Organosilica Shell: Ideal Nanoreactors for Selective Alcohol Oxidation, Adv. Functional Mater., 22(3):591-9 (Feb. 2012).
Liu et al., Yolk/shell nanoparticles: new platforms for nanoreactors, drug delivery and lithium-ion batteries, Chem. Commun., 47:12578-91 (2011).
Lou et al., Designed synthesis of coaxial SnC>2@carbon hollow nanospheres for highly reversible lithium storage. Adv. Mater. 21: 2536-9 (2009).
Lou et al., Encapsulation and Ostwald Ripening of Au and Au—Cl Complex Nanostructures in Silica Shells, Adv. Functional Mater., 16(13):1679-84 (Sep. 2006).
Lou et al., Hollow micro-/nanostructures: synthesis and applications, Adv. Mater., 20:3987-4019 (2008).
Lou et al., Shell-by-Shell Synthesis of Tin Oxide Hollow Colloids with Nanoarchitectured Walls: Cavity Size Tuning and Functionalization, Small, 3(2):261-5 (Feb. 2007).
Lou et al., Template-Free Synthesis of SnO2 Hollow Nanostructures with High Lithium Storage Capacity, Adv. Mater., 18(17):2325-9 (Sep. 2006).
Lu et al., Aerosol-assisted self-assembly of mesostructured spherical nanoparticles, Nature, 398:223-6 (1999).
Ma et al., Three-Dimensional Nitrogen-Doped Carbon Nanotubes/Graphene Structure Used as a Metal-Free Electrocatalyst for the Oxygen Reduction Reaction, J. Phys. Chem. C, 115(50):24592-7 (2011).

(56) References Cited

OTHER PUBLICATIONS

Mandal et al., Production of Hollow Polymeric Microspheres by Surface-Confined Living Radical Polymerization on Silica Templates, Chem. Mater., 12(11):3481-7 (2000).
Matsui et al., Assembly of untreated single-walled carbon nanotubes at a liquid-liquid interface. Carbon, 47(6):1444-50 (2009).
Metz et al., Nanotextured gold coatings on carbon nanofiber scaffolds as ultrahigh surface-area electrodes. Journal of Power Sources 2012, 198, 393-401.
Nie et al., Platinum supported on reduced graphene oxide as a catalyst for hydrogenation of nitroarenes, Carbon, 50(2):586-96 (Feb. 2012).
Park et al., Preparation of hollow silica microspheres in W/O emulsions with polymers, J. Colloid Interface Sci., 266(1):107-14 (Oct. 2003).
Saravanan et al., Hollow a-LiVOPO4 sphere cathodes for high energy Li-ion battery application, J. Mater. Chem., 21:10042-50 (2011).
Seo et al., A homochiral metal-organic porous material for enantioselective separation and catalysis, Nature, 404(6781):982-6 (Apr. 2000).
Shen et al., Emulsions Stabilized by Carbon Nanotube-Silica Nanohybrids. Langmuir, 25(18):10843-51 (2009).
Singh et al., Structural evolution in cationic micelles upon incorporation of a polar organic dopant, Langmuir, 20(23):9931-7 (Nov. 2004).
Suarez et al., Synthesis of Highly Uniform Mesoporous Sub-Micrometric Capsules of Silicon Oxycarbide and Silica, Chem. Mater., 19(13):3096-8 (2007).
Sunkara et al., Modifying metal nanoparticle placement on carbon supports using an aerosol-based process, with application to the environmental remediation of chlorinated hydrocarbons, Langmuir, 27(12):7854-9 (Jun. 2011).
Suzuki et al., Janus Microgels Prepared by Surfactant-Free Pickering Emulsion-Based Modification and Their Self-Assembly. J.Am. Chem. Soc., 129(26):8088-9 (2007).
Tacchini et al., Hydrothermal synthesis of ID TiO(2) nanostructures for dye sensitized solar cells. Materials Science and Engineering B—Advanced Functional Solid-State Materials, 177(1):19-26 (2012).
Tan et al., Surfactant solubilization and the direct encapsulation of interfacially active phenols in mesoporous silicas, Langmuir, 24(3):1031-6 (Feb. 2008).
Teng et al., Synthesis of thin-walled carbon nanocages and their application as a new kind of nanocontainer, J. Mater. Chem., 21:5443-50 (2011).
Tissot et al., SiOH-Functionalized Polystyrene Latexes. A Step toward the Synthesis of Hollow Silica Nanoparticles, Chem. Mater., 14(3):1325-31 (2002).
Uhm et al., A facile route for preparation of non-noble CNF cathode catalysts in alkaline ethanol fuel cells, Electrochimica Acta, 56(25):9186-90 (Oct. 2011).
Venkataraman et al., Water-in-Trichloroethylene Emulsions Stabilized by Uniform Carbon Microspheres. Langmuir, 28(2):1058-63 (2012).
Vignati et al., Pickering Emulsions: Interfacial Tension, Colloidal Layer Morphology, and Trapped-Particle Motion. Langmuir, 19(17):6650-6 (2003).
Wang et al., Amphiphobic Carbon Nanotubes as Macroemulsion Surfactants. Langmuir, 19(8):3091-3 (2003).
Wang et al., Double-layer coating of SrCO(3)/TiO(2) on nanoporous TiO(2) for efficient dye-sensitized solar cells, Phys. Chem. Chem. Phys., 14(2):816-22 (2012).
Wang et al., Facile fabrications of noble metal nanoparticles encapsulated in hollow silica with radially oriented mesopores: multiple roles of the N-lauroylsarcosine sodium surfactant, Chem. Commun., 47:7680-2 (2011).
Wang et al., Synthesis and Lithium Storage Properties of Co3O4 Nanosheet-Assembled Multishelled Hollow Spheres, Adv. Functional Mater., 20(10):1680-6 (May 2010).
Wang et al., Synthesis of submicrometer hollow particles with nanoscale double-layer shell structure, Langmuir, 28:13783-7 (2012).

Wietecha et al., Platinum nanoparticles anchored on chelating group-modified graphene for methanol oxidation, J. Power Sources, 198:30-5 (Jan. 2012).
Wu et al., Biocompatibility, MR imaging and targeted drug delivery of a rattle-type magnetic mesoporous silica nanosphere system conjugated with PEG and cancer-cell-specific ligands, J. Mater. Chem., 21:3037-45 (2011).
Wu et al., Catalytic nano-rattle of Au@hollow silica: towards a poison-resistant nanocatalyst, J. Mater. Chem., 21:789-94 (2011).
Wu et al., Raspberry-like Silica Hollow Spheres:? Hierarchical Structures by Dual Latex-Surfactant Templating Route, J. Phys. Chem. C, 111(27):9704-8 (2007).
Xu et al., Synthesis and utilization of monodisperse hollow polymeric particles in photonic crystals, J. Am. Chem. Soc., 126(25):7940-5 (Jun. 2004).
Xu et al., Urchin-like GdPO4 and GdPO4:Eu3+ hollow spheres-hydrothermal synthesis, luminescence and drug-delivery properties, J. Mater. Chem., 21:3686-94 (2011).
Yang et al., Hollow silica nanocontainers as drug delivery vehicles, Langmuir, 24(7):3417-21 (Apr. 2008).
Yang et al., Mesoporous CeO2 Hollow Spheres Prepared by Ostwald Ripening and Their Environmental Applications, Eur. J. Inorg. Chem., 2010(21):3354-9 (Jul. 2010).
Yin et al., Formation of hollow nanocrystals through the nanoscale Kirkendall effect, Science, 304(5671):711-4 (Apr. 2004).
Yin et al., Functionalizing carbon nanotubes for effective electrocatalysts supports by an intermittent microwave heating method. Journal of Power Sources 2012, 198, 1-6.
Yoon et al., Template synthesis of nanostructured silica with hollow core and mesoporous shell structures, Current Applied Physics, 6(6):1059-63 (Oct. 2006).
Yuan et al., C12mimBr Ionic Liquid/SDS Vesicle Formation and Use as Template for the Synthesis of Hollow Silica Spheres, Langmuir, 26(14):11726-31 (2010).
Zha et al., Monodisperse Temperature-Sensitive Microcontainers, Adv. Mater., 14(15):1090-2 (Aug. 2002).
Zhan et al., Carbothermal Synthesis of Aerosol-Based Adsorptive-Reactive Iron-Carbon Particles for the Remediation of Chlorinated Hydrocarbons, Ind. Eng. Chem. Res., 50(23):13021-9 (Aug. 2011).
Zhan et al., Multifunctional Iron-Carbon Nanocomposites through an Aerosol-Based Process for the In Situ Remediation of Chlorinated Hydrocarbons, Environ. Sci. Technol., 45(5):1949-54 (2011).
Zhang et al., A facile in situ hydrophobic layer protected selective etching strategy for the synchronous synthesis/modification of hollow or rattle-type silica nanoconstructs, 22:12553-61 (2012).
Zhang et al., Carbon Nanofibers Decorated with Poly(furfuryl alcohol)-Derived Carbon Nanoparticles and Tetraethylorthosilicate-Derived Silica Nanoparticles, Langmuir, 27(23):14627-31 (2011).
Zhang et al., Directing single-walled carbon nanotubes to self-assemble at water/oil interfaces and facilitate electron transfer. Chem. Comm., (36):4273-5 (2008).
Zhang et al., Formation of ZnMn2O4 Ball-in-Ball Hollow Microspheres as a High-Performance Anode for Lithium-Ion Batteries, Adv. Mater., 24(34):4609-13 (Sep. 2012).
Zhang et al., Iron tetrasulfophthalocyanine functionalized graphene as a platinum-free cathodic catalyst for efficient oxygen reduction in microbial fuel cells, J. Power Sources, 197:93-6 (Jan. 2012).
Zhao et al., Fabrication of uniform hollow mesoporous silica spheres and ellipsoids of tunable size through a facile hard-templating route, J. Mater. Chem., 19:2778-83 (2009).
Zhao et al., Hollow Micro/Nanomaterials with Multilevel Interior Structures, Adv Mater., 21(36):3621-38 (2009).
Zheng et al., Surfactant Templating Effects on the Encapsulation of Iron Oxide Nanoparticles within Silica Microspheres, Langmuir, 23(9):5143-7 (2007).
Zhou et al., Double-Shelled CoMn2O4 Hollow Microcubes as High-Capacity Anodes for Lithium-Ion Batteries, Adv. Mater., 24(6):745-8 (Feb. 2012).
Zhu et al., Stimuli-responsive controlled drug release from a hollow mesoporous silica sphere/polyelectrolyte multilayer core-shell structure, Angew. Chem. Int. Ed. Engl., 44(32):5083-7 (Aug. 2005).
Zoldesi et al., Deformable hollow hybrid silica/siloxane colloids by emulsion templating, Langmuir, 22(9):4343-52 (Apr. 2006).

(56) References Cited

OTHER PUBLICATIONS

Zoldesi et al., Synthesis of Monodisperse Colloidal Spheres, Capsules, and Microballoons by Emulsion Templating, Adv. Mater., 17(7):924-8 (Apr. 2005).

* cited by examiner

HOLLOW NANOPARTICLES WITH HYBRID DOUBLE LAYERS

CROSS-REFERENCES TO RELATED APPLICATIONS

This is a non provisional patent application of U.S. Provisional Patent Application Ser. No. 61/599,788, filed 16 Feb. 2012; U.S. Provisional Patent Application Ser. No. 61/610,798, filed 14 Mar. 2012; and U.S. Provisional Patent Application Ser. No. 61/621,642, filed 9 Apr. 2012.

Priority of U.S. Provisional Patent Application Ser. No. 61/599,788, filed 16 Feb. 2012; U.S. Provisional Patent Application Ser. No. 61/610,798, filed 14 Mar. 2012; and U.S. Provisional Patent Application Ser. No. 61/621,642, filed 9 Apr. 2012, each of which is hereby incorporated herein by reference, is hereby claimed.

STATEMENT REGARDING FEDERALLY SPONSORED RESEARCH

Funding was received from the US Department of Energy (grant DE-FG02-05ER46243), the National Science Foundation (grants 0933734, 1034175, and 1236089), and the Gulf of Mexico Research Initiative. The United States government has certain rights in this invention.

COMPACT DISK SUBMISSION

Not Applicable.

BACKGROUND OF INVENTION

Field of the Invention

The present invention relates to hollow nanoparticles. More particularly, the present invention relates to methods for fabricating double layer hollow nanoparticles.

The discovery of mesoporous silica templated by surfactants has led to tremendous interest in developing new classes of porous materials. It is now well-known now that the introduction of a templating surfactant such as cetyl trimethylammonium bromide (CTAB) into a solution containing a silica precursor such as tetraethyl orthosilicate (TEOS) leads to the formation of ordered mesoporous silica. Of significance is the rapid synthesis of such materials by the aerosol based method of making porous materials by incorporating surfactants into precursor solutions of a silica precursor. The aerosol method is advantageous because it is continuous, effective and economical. A very recent and comprehensive review (X. W. Lou, Lynden A. Archer, and Zichao Yang, *Hollow Micro-/Nanostructures: Synthesis and Applications*, Adv. Mater. 2008, 20, 3987-4019) describes the versatility and use of the process to produce functional inorganic materials.

This invention discloses the use of similar methods to produce unexpected non-mesoporous materials.

Description of Related Art

Hollow particles are of considerable interest because of their wide range of applications in encapsulation, catalysis, biomolecule separation, controlled drug release, and sensor technologies/biosensors. Typically, the preparation of such hollow particles requires building a desirable material layer around a core, followed by removal of the core by dissolution or high temperature calcination. These synthesis approaches generally involve multistep operations and complex components, leading to difficulties in scale up to commercially viable quantities.

The present invention discloses a scalable, rapid aerosol-based process for fabricating hollow submicrometer particles with novel morphology, one where the shell is made up of two thin layers: an outer layer of silica (or other ceramic) and an inner layer of carbon. The exposed surfaces therefore have contrasting physical characteristics, with the outer surface being hydrophilic and the inner surface being hydrophobic. Additionally, the particles contain iron nanoparticles, making them magnetically responsive.

Double-shelled hollow particles have recently been pioneered through template-based methods to form $SnO_2$ layers for lithium storage enhancements, and these advances point to important applications of such materials.

A recent and comprehensive review of the aerosol process describes the versatility and use of the process to produce functional inorganic materials, and we refer the readers to this article for an excellent background of the process (See Boissiere, C.; Grosso, D.; Chaumonnot, A; Nicole, L.; Sanchez, C. Aerosol route to functional nanostructured inorganic and hybrid porous materials. *Adv. Mater.* 2011, 23, 599-623). The concept behind the present work is an important aspect of the aerosol process that has hitherto not been explored. It is well known now that the introduction of a templating surfactant such as cetyl trimethylammonium bromide (CTAB) into a solution containing a silica precursor such as tetraethyl orthosilicate (TEOS) leads to the formation of ordered mesoporous silica. In our recent work, however, we have surprisingly found that the inclusion of ferric chloride into the precursor solution completely negates the templating effect. Rather, the inclusion of the ferric salt leads to a binding of the CTAB and a phase segregation where the iron salt and CTAB become occluded within the interior of a rapidly forming shell of silica during the passage of the aerosol droplets through the heating zone of a tube furnace. Subsequent calcination of these particles leads to the burnoff of the organic surfactant species, leaving behind hollow silica particles containing magnetic iron oxides. The present invention is based on a new extension of this concept. If a rapid shell of silica is formed, can this shell act as a seal to prevent the escape of material from the interior of the particle? Specifically, if carbon precursors (sucrose) are introduced into the precursor solution, can the carbonization of sucrose be conducted in the interior of such thin-shelled silica particles? The first part of the schematic in FIG. 4 (I and II) illustrates the concept of aerosolization and the incorporation of carbon into the interior of the particle. The latter parts of FIG. 4 are related to the results that are described herein.

Various other methods have been developed to synthesize single layer hollow nanoparticles, including hard template, soft template, dual template, Ostwald ripening, as well as Kerkendall effect, but these preparation schemes generally involve multistep operations, complex components, and hence are less economical.

One-step aerosol-assisted process is an efficient approach to prepare single layer hollow nanoparticles. However, to our knowledge fabrication of double layer nanoparticles through a simple and effective aerosol assisted process have never been reported before.

Incorporated herein by reference are the following references:

X. W. Lou, Lynden A. Archer, and Zichao Yang, *Hollow Micro-/Nanostructures: Synthesis and Applications*, Adv. Mater. 2008, 20, 3987-4019.

Hu Wang, Jin-Gui Wang, Hui-Jing Zhou, Yu-Ping Liu, Ping-Chuan Sun and Tie-Hong Chen, *Facile fabrication of noble metal nanoparticles encapsulated in hollow silica with radially oriented mesopores: multiple roles of the N-lauroylsarcosine sodium surfactant*, Chem. Commun., 47, 7680-7682. 2011.

Yinqquin Wang, Bhanukiran Sunkara, Jinjing Zhan, Jibao He, Ludi Miao, Gary L. McPherson, Vijay T. John, and Leonard Spinu, *Synthesis of Submicrometer Hollow Particles with Nanoscale Double-Layer Shell Structure*, Langmuir 2012, 28, 13783-13787.

BRIEF SUMMARY OF THE INVENTION

The present invention provides bilayer hollow nanoparticles and a method of making the same.

In a preferred embodiment, a double layered nanoparticle is fabricated in a one-step aerosol-assisted synthesis method. In one embodiment, the outer layer is silica and the inner layer is carbon.

In another embodiment of the present invention, an outer silica layer of a bilayer nanoparticle may be etched away to fabricate hollow carbon spheres. In one embodiment a hollow sphere may encapsulate a substance. In yet another embodiment, the substance encapsulated may be a pharmaceutical compound.

In another embodiment of the present invention an inner carbon layer of hollow bilayer nanoparticles may be burnt away to fabricate silica spheres.

Another embodiment of the present invention may be to manufacture hollow bilayer nanoparticles with magnetic nanoparticles. In one embodiment, the magnetic nanoparticles may be iron. In addition to iron, it is possible to insert a variety of other metallic nanoparticles (tin, copper, palladium, chromium, zinc, rhodium, ruthenium, molybdenum—the whole series of transition metal oxides). In another embodiment, the magnetic nanoparticles may be used for drug delivery.

In another embodiment, bilayer particles may be used as amphiphilic particles to stabilize emulsions. In one embodiment, bilayer particles may be used in Pickering emulsions.

In another embodiment, bilayer particles may be used as catalytic materials. In one embodiment carbon and silica within bilayer particles may function as supports for catalytic materials.

In accordance with this invention, it is an object of this invention to incorporate iron oxide into the shell of the bilayer structure to make it magnetically responsive. The inner void allows entrapment of a high concentration of a drug agent which may be magnetically guided for targeted drug delivery.

In accordance with this invention, it is an additional object to etch away the silica layer to make hollow carbon spheres with applications to fuel cell technologies as electrode for fuel cells, for using carbon as a catalyst.

In accordance with this invention, it is an additional object to burn away carbon to make hollow silica spheres with application in drug delivery and as catalyst supports.

Some embodiments of the invention include eggshell type nanoparticles that are particles with an extremely thin outer layer that can crack or break upon a slight impact or ultrasonication. In some embodiments these eggshell particles may have a shell of 10-15 nm (though even a shell as thin as 5-7 nm and up to 20 nm thick can be useful). Some embodiments include methods of producing said eggshell particles comprising sending a precursor solution comprising a surfactant, a silica precursor, and a metal precursor such as a metal salt, through a heating zone. Some embodiments comprise a precursor solution with less silica precursor than a 1 to 8 ratio of metal salt to silica precursor.

Some embodiments of the invention include bilayer nanoparticles with protuberances referred to here as "nanohorns." In some embodiments, there may be at least one nanohorn with the nanoparticle comprising an outer layer of silica and an inner layer of carbon. Some embodiments include methods of producing said nanoparticles with nanohorns comprising sending a precursor solution comprised of a surfactant, a silica precursor, a metal precursor such as a metal salt, and a carbon precursor through a heating zone, and then pyrolyzing the particles. Some embodiments may further include calcination of the particles to remove the carbon layer, or etching of the particles to remove the silica layer.

Some embodiments of the invention include nanoparticles made with metal based precursors in place of a carbon based precursor. Some embodiments may use a titania precursor, such as titanium isopropoxide in place of a carbon precursor. In some embodiments, the silica may be etched away leaving titania nanospheres. In some embodiments, light is expected to penetrate the titania nanospheres.

Hollow nano and microparticles have a variety of applications in encapsulation, catalysis, energy storage, chemical sensing and controlled drug release. Typically they are prepared by forming a layer of the desired materials over a template which is then selectively removed by dissolution or burn-off to create a hollow core. In the present invention, a new method for manufacturing ceramic particles where a shell is created extremely rapidly, locking in chemical constituents in the interior. This is done using an aerosol based process where we have exploited salt bridging concepts to lock a surfactant (CTAB) and carbon precursors together with iron oxides in the interior of a droplet while a silica shell is allowed to form on the droplet surface. Subsequent pyrolysis results in a buildup of internal pressure forcing carbon formation as a second layer attached to the silica shell. Thus we have developed bilayer "amphiphilic" ceramic particles with a hollow interior. This new assembly method is expected to be a general approach to fabricate various hybrid double layer hollow particles with unique potential properties. In addition, the incorporation of magnetic iron oxide into the shells opens up opportunities in external stimuli responsive materials.

The present invention describes novel nanoparticles and methods of producing the same. The novel aspects of the present invention are the following: (1) the iron chloride ties up the surfactant (e.g., CTAB) so that the silica cannot grow inwards from the surface of the drop—this is why hollow particles are generated; and (2) when the carbon precursor is also enclosed in the interior, the pressure build up leads to the second shell being generated from the inside (as opposed to building shells from the outside through a layer-by-layer method). These are important differences from prior art and lead to the ability to be able to generate large quantities of hollow and double shelled particles.

BRIEF DESCRIPTION OF DRAWINGS

The following drawings form part of the present specification and are included to further demonstrate certain aspects of the present invention. The invention may be better understood by reference to one or more of these drawings in combination with the description of specific embodiments presented herein.

FIGS. 48(a) and (b) are images of aerosolized particles. FIGS. 48(c) and (d) are images of calcined particles.

FIGS. 49(a) and (b) are images of aerosolized particles. FIGS. 49(c) and (d) are images of calcined particles.

DETAILED DESCRIPTION OF THE INVENTION

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

The hollow particles of the claimed invention can be made of (a) silica; (b) silica-carbon double shelled; (c) silica-titania mixed shell; or (d) silica-titania-carbon with the outer shell being silica-titania and the inner shell being carbon. The silica in these particles can be etched out leaving (a) carbon hollow particles; (b) titania shelled hollow particles; or (c) titania-carbon particles.

Figure 6:
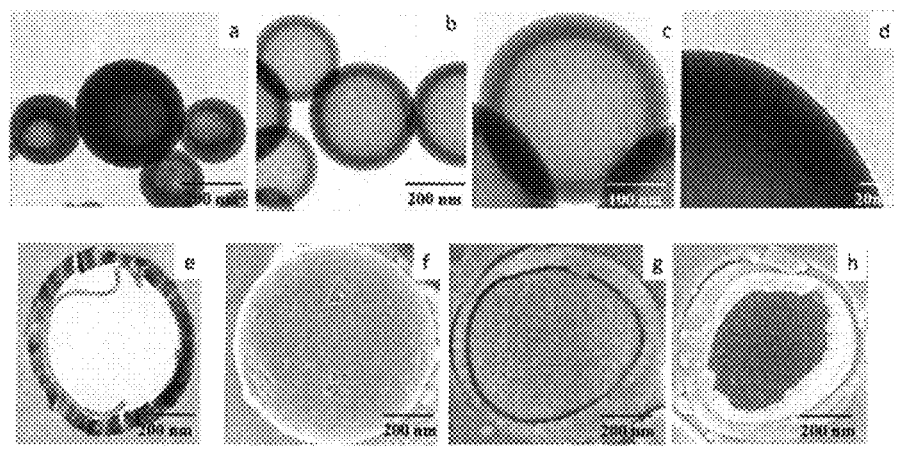
FIG. 6 shows representative electron micrographs of hollow nanoparticles with double silica/carbon layer shell: (a) TEM image of as-synthesized nanoparticles; (b) TEM image of pyrolyzed nanoparticles at low magnification; (c) TEM image of pyrolyzed nanoparticles at high magnification; (d) High resolution TEM image of a pyrolyzed nanoparticle; (e) Cross section TEM image of a pyrolyzed nanoparticle; (f) SEM image of a pyrolyzed nanoparticle at high magnification; (g) Cross section SEM image of a pyrolyzed nanoparticle with partial removal of the outer layer; (h) Cross section SEM image of a pyrolyzed nanoparticle.

All these hollow particles can be made to contain iron nanoparticles. In addition to iron, it is possible to also insert a variety of other metallic nanoparticles (tin, copper, palladium, chromium, zinc, rhodium, ruthenium, molybdenum, manganese, nickel, aluminum—in fact the whole series of transition metal oxides). It is noted that these particles are in addition to iron; for example, the nanoparticles within the hollow particles are either (a) iron; or (b) iron plus a second metal. The second metal can be inserted into the hollow particles through multiple pathways, such as for example, (a) it can be added to the precursor solution prior to aerosolization and thus gets incorporated into the hollow particles; or (b) it can be allowed to diffuse using the metal salt through the pores of premade hollow particles. Tin (Sn) is especially important as it can be used effectively for Li-ion batteries. We also note that the metal inside the hollow particles is loose and not attached to the shell. This qualifies denoting the particles as "rattle" type particles.

FIG. 1 illustrates an aerosol based process to make submicron particles. In one embodiment, the precursor solution may be aerosolized through a nozzle and the drops may pass through a furnace where solvent evaporation may occur together with chemical reaction. This so called "chemical reaction in an evaporating droplet" may result in small particles which may be collected on a filter. The process is easy to scale up to a semicontinuous production method where the product from the furnace can be directed towards a second filter set up when the first one is disconnected for particulate retrieval.

Normally, this process results in mesoporous particles, however, in one embodiment as FIG. 2 illustrates, increasing the amount of iron salt ($FeCl_3$) in solution unexpectedly leads to a loss of order in the mesoporous material and finally the formation of hollow particles. Embodiments describes here include a very rapid method of producing hollow particles, which may be used in encapsulation, catalysis, biomolecule separation, controlled drug release, and biosensor technologies. Typically the preparation of such hollow particles requires building a layer around a core followed by removing the core by dissolution or high temperature. Such schemes generally contain multistep operations and complex components, involving difficulties in scale up to commercially viable quantities. Developing a rapid technique to make such particles in reasonably large quantities would therefore be of technological significance.

As illustrated in FIG. 3, double layer hollow nanoparticles may be prepared using tetraethyl orthosilicate (TEOS) as a silica source and a monosaccharide or polysaccharide, such as sucrose (most preferable), glucose, cellulose, or cyclodextrins as a carbon source in the presence of ferric chloride (or other iron salt such as other ferric halides, or mixtures of iron salts) and surfactant, such as cetyltrimethyl ammonium bromide (CTAB, a directing agent), cetyltrimethyl ammonium chloride (CTAC) or other CTA-halides, such as cetyltrimethyl ammonium iodide (CTAI), cetyltrimethyl ammonium fluoride (CTAF), cetyltrimethyl ammonium astatide (CTAA). Also, instead of the silica source, zirconia, alumina or titania can be used. The precursor solution may be initially atomized to form aerosol droplets, which may then be sent through a drying zone and heating zone where preliminary solvent evaporation, silica condensation and sucrose dehydration may occur.

Typically, CTAB templates highly ordered hexagonal mesoporous silica through the aerosol process. However $FeCl_3$ in the precursor solution disrupts the formation of mesoporous silica due to preferential partitioning of the surfactant CTAB on ferric species, therefore the dense, low porous silica layer may be formed during the aerosol process. The iron chloride ties up the surfactant CTAB so that the silica cannot grow inwards from the surface of the drop—this is why hollow particles are generated.

As depicted in the schematic of FIG. 5, the hollow particle formation mechanism may involve two key and novel processes: 1) the formation of the silica shell due to the preferred silica condensation reaction along the gas-liquid interface of an aerosol droplet; and 2) the formation of an iron-surfactant rich core by the coagulation of ferric species in the presence of the surfactant. Upon mixing $FeCl_3$, TEOS and CTAB in an acidic ethanol/water solution, the hydrolysis of $FeCl_3$ generates ferric colloids that are stabilized by the electrical double layers of chloride anions. The added CTAB, however, serves as an indifferent electrolyte, promoting ferric colloid coagulation visualized by a translucent solution appearance. The coagulation effect is further supported by the fact that increased CTAB loading leads to larger CTAB/Fe cores and thinner silica shells. Higher indifferent electrolyte concentration in the precursor promotes the coagulation of ferric colloids, resulting in larger CTAB/Fe colloids. Subsequent atomization of the mixture generates aerosol droplets containing silicates, CTAB, the coagulated ferric species, ethanol and water. Solvent evaporation enriches these nonvolatile components and promotes faster silicate condensation along the gas/liquid interface, resulting in the formation of a silica-rich shell. Calcination of the particles removes the CTAB and converts the ferric core into an iron oxide nanoparticle possibly due to the sintering and/or ripening processes confined by the silica shell.

The schematic in FIG. 4 illustrates an embodiment where a carbon precursor is added to the precursor solution. The precursor solution (I) which now contains a carbon precursor (e.g., sucrose) is atomized to form aerosol droplets, which are then sent through a heating and a drying zone where preliminary solvent evaporation, silica condensation and sucrose dehydration occur.

The morphology of the hollow nanoparticles was evaluated by scanning electron microscopy (SEM) and transmission electron microscopy (TEM). The synthesized nanoparticles have well-defined spherical structures and the size is in the range of 100 to 1000 nm, which is consistent with characteristic droplet size distribution through aerosol process. The hollowness of synthesized nanoparticles is supported by TEM. The representative images of synthesized double layer hollow nanoparticles are shown in FIG. 6.

The nanoparticles have interesting morphology transition from ill-defined hollow structure (FIG. 6*a*) to well-defined double layer hollow structure after pyrolysis treatment (FIGS. 6*b* and 6*c*). The as-synthesized nanoparticles may have hollow irregular inner surface and the surface may become spherical after pyrolysis treatment, indicating the pyrolysis of nanoparticles effectively removes CTAB and the remaining sucrose. The thickness of two layers is variable with the size of nanoparticle. The silica shell layer can be about 5 nm to 100 nm thick and 50 nm to 5,000 nm in outer diameter. For example, the silica shell layer outer diameter can be about 100 nm to 1000 nm. The carbon layer can be about 5 nm to 100 nm thick and 50 to 5000 nm, 100 nm to 1,000 nm in outer diameter. For example, the carbon layer outer diameter can be about 100 nm to 1,000 nm. Based on TEM observation (FIG. 6d), it is clear that the thickness of the outer layer and inner layer are approximately 30 nm and 50 nm, respectively. Cross section TEM and SEM images (FIGS. 6e, 6g and 6h) further reveal the double layer nature of the hollow nanoparticles. The cross section TEM images show noodle like inner layer structure and fractured outer layer (FIG. 6e), which may be caused by the cutting procedure of cross section TEM sample preparation. The cross section SEM images (FIGS. 6g and 6h) of a synthesized nanoparticle further confirm the appearance of two distinct layers of the hollow particle.

Figure 4:
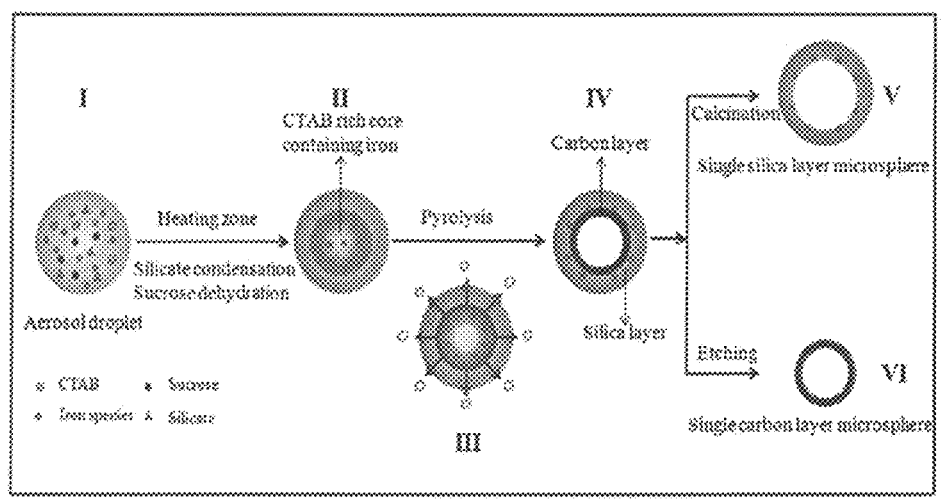
FIG. 4 illustrates an exemplary method for the formation of silica/carbon double layer hollow particles.
Figure 5:
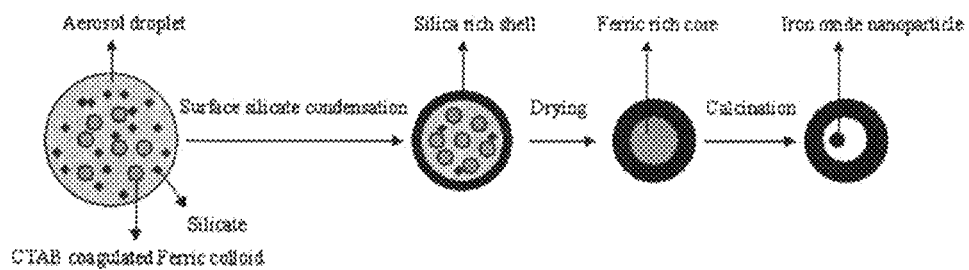
FIG. 5 illustrates an exemplary mechanism for formation of silica hollow sphere and encapsulation of iron oxide inside the nanoparticle sphere. The preferential partitioning of CTAB to the ferric species leads to depletion of CTAB from silicate regions and a segregation of dense silica as the shell and the ferric species in the core.
Figure 7:
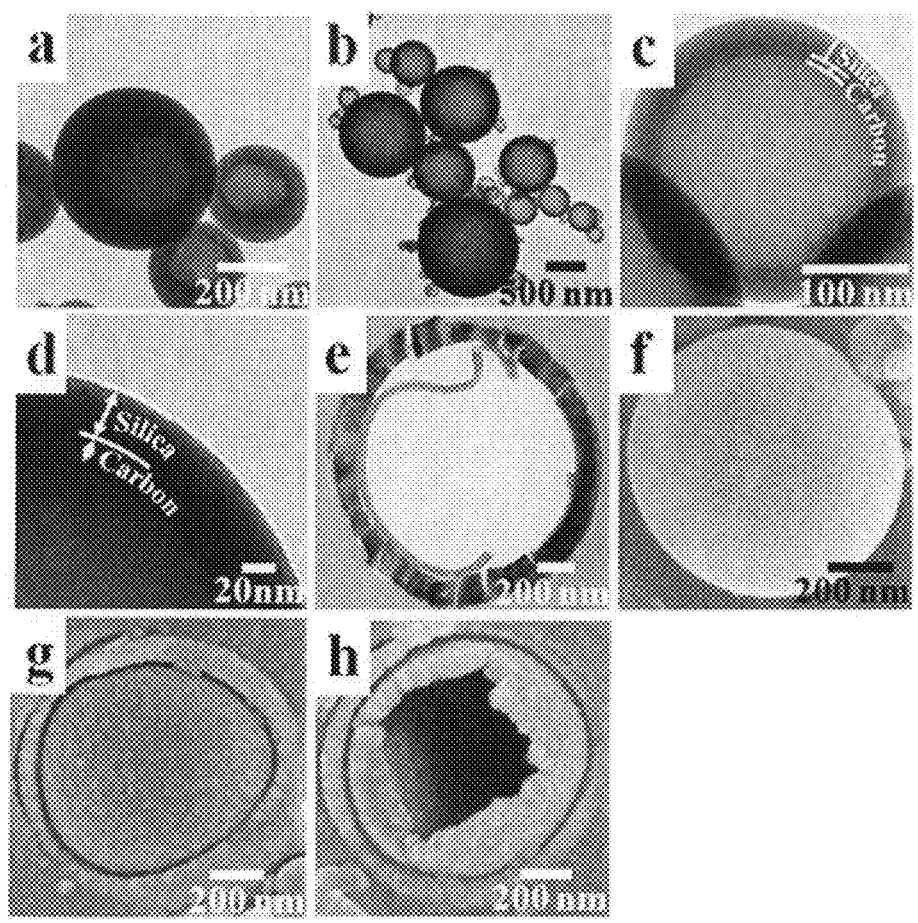
FIG. 7 shows representative electron micrographs of hollow particles with a double silica/carbon layer shell: (a) TEM image of as-synthesized particles; (b) TEM image of pyrolyzed particles at low magnification showing a wide range of particle sizes; (c) TEM image of a pyrolyzed particle at high magnification; (d) HRTEM image of a pyrolyzed particle showing the two layers; (e) Cross section TEM image of a pyrolyzed particle with a detached carbon layer; (f) SEM image of a pyrolyzed particle; (g) Cross section SEM image of a pyrolyzed particle where sectioning leaves an intact inner shell. (h) Cross section SEM image of a pyrolyzed particle where sectioning cuts across both shells to reveal the hollow interior.
Figure 8:
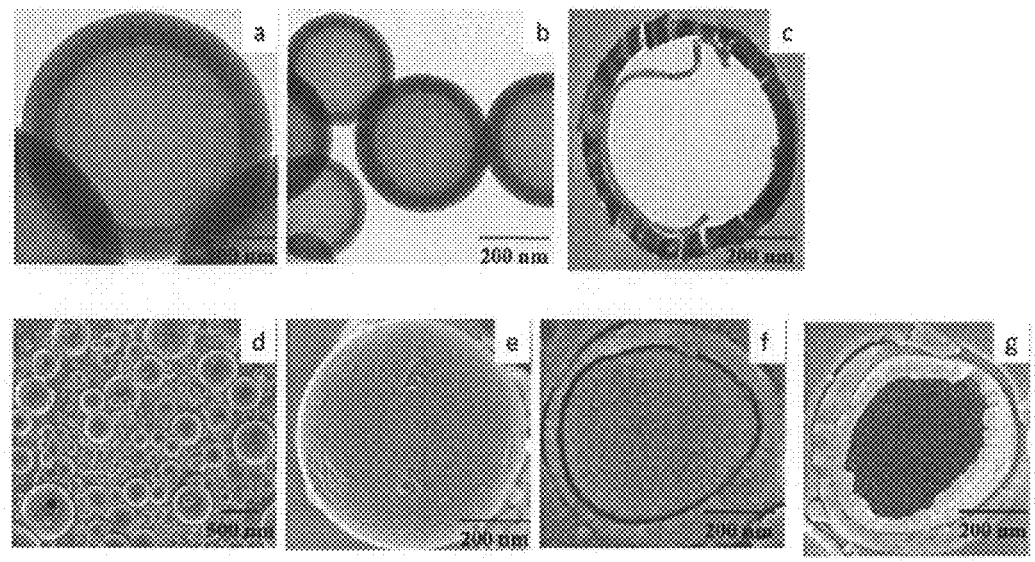
FIG. 8 shows representative electron micrographs of hollow microspheres with double layer silica/carbon shell: (a)-(b), TEM images of pyrolyzed microspheres; (c) Cross section TEM image of a pyrolyzed microsphere; (d)-(e), SEM images of pyrolyzed microspheres; (f)-(g), Cross section SEM images of pyrolyzed microspheres.
Figure 9:
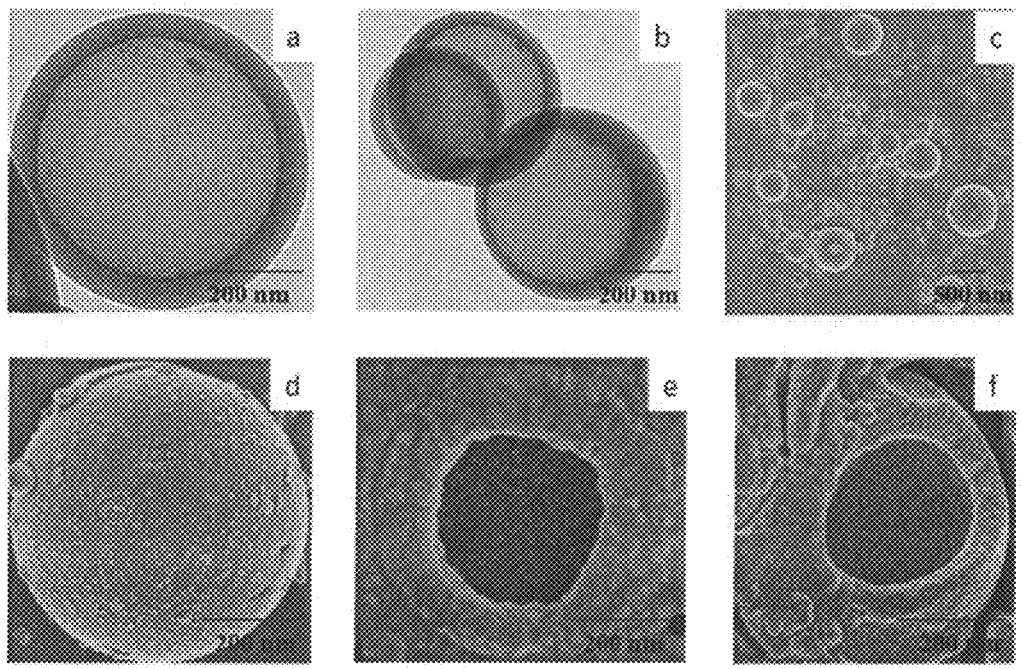
FIG. 9 shows further representative electron micrographs of hollow microspheres with double layer silica/carbon shell: (a)-(b), TEM images of calcined microspheres; (c)-(d), SEM images of calcined microspheres; (e)-(f), Cross section SEM images of calcined microspheres.
Figure 10:
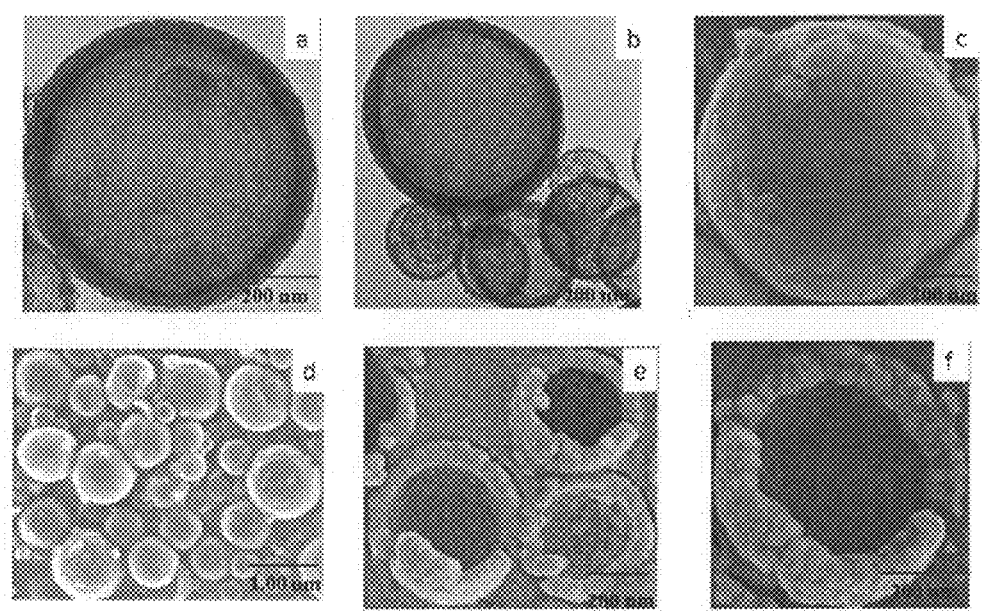
FIG. 10 shows further representative electron micrographs of hollow microspheres with double layer silica/carbon shell: (a)-(b), TEM images of etched microspheres; (c)-(d), SEM images of etched microspheres; (e)-(f), Cross section SEM images of etched microspheres.

The present invention demonstrates that in the presence of sucrose the much slower carbonization of the sugar would occur in the interior of a particle with a silica shell. FIG. 7a shows the nature of the particles obtained immediately after the aerosol process (II in FIG. 4). The particles are as yet poorly defined, although they do show evidence of significant internal void space.

In one embodiment, the as-synthesized particles are then pyrolyzed at 500° C. for 3 h in a tube furnace under flowing nitrogen gas to generate carbon species through full dehydration and carbonization. Instead of nitrogen, one could use a different inert gas, such as argon or any gas which one of ordinary skill in the art would know or discover through routine experimentation. The resultant observation is remarkable, as the carbon forms as a discrete second layer adjoining the silica shell leaving a fully hollow interior (IV in FIG. 1 and FIG. 7b). When the carbon precursor is enclosed in the interior, the pressure build up leads to the second shell being generated from the inside, as opposed to building shells from the outside through a layer-by-layer method. FIG. 7b provides a panoramic image of multiple particles showing a large size distribution, but also showing that every particle is hollow. The higher resolution images of FIGS. 7c and 7d shows the evidence of a double layer at progressively increasing resolution of the images. As FIG. 7d illustrates, the outer layer is approximately 40 nm thick, while the inner layer is less than 20 nm. The cross section TEM of a particle (FIG. 7e) shows that the sectioning process destroys the integrity of the layers. The striations seen in the outer layer are not pores but jagged edges created during thin (70 nm thickness) sectioning. It is clear that the broken inner layer also becomes separated from the outer layer upon sectioning. FIG. 7f illustrates the external morphology of a particle through SEM. FIGS. 7g and 7h were obtained by embedding the particles in epoxy resin, making just one cut to create a thick section which was then imaged through SEM. FIG. 7g shows a particle where the outer layer was cut away exposing an intact inner layer surface, while FIG. 7h illustrates a particle where both layers were cut revealing the interior voidage. We note that the particles shown in FIGS. 7e through 7h represent those at the upper end of the size distribution where clarity of the microstructure is achieved after the sectioning process.

The present invention demonstrates that reason for the generation of these double-layer particles is that the silica shell seals in the carbon precursors during the aerosolization process. During pyrolysis, the off gases generated build up a high internal pressure and push the carbonaceous species to the inner surface of the silica shell. Assuming the silica shell is impermeable until pressures are built up to force out the pyrolysis gases, the internal pressures generated can be as high as 175-200 atm. The pyrolysis gases are essentially forced out through micropores in the silica layer. The pyrolysis step is depicted through the schematic (III) in FIG. 4, and the final pyrolyzed material (IV) illustrates the generation of the double-layer particles.

Estimation of internal pressures generated during pyrolysis-Assumptions:
a) the outer silica layer is formed extremely rapidly to seal in carbon precursors;
b) an average particle size of 190 nm with a silica shell of 35 nm;
c) precursor concentrations in a droplet are the same as that in the precursor feed solution.

With these assumptions, the molar concentration of sucrose inside a droplet is 0.137M. If we assume a droplet dimension also of 190 nm, the droplet (and eventually the particle) contains $3.94 \times 10^{-18}$ moles of sucrose. The dehydration reaction of sucrose during pyrolysis is $C_{12}H_{22}O_{11} \rightarrow 12C + 11H_2O$ (g) Hence, the moles of generated gas species (superheated steam) is $$n = 11 \times 3.94 \times 10^{-18} \text{ moles} = 4.33 \times 10^{-17} \text{ moles}$$

Appling the ideal gas law, the internal pressure can be estimated:

$$P = nRT/V = (4.33 \times 10^{-17} \text{ mole}) \times (8.314 \text{ J K}^{-1} \text{ Mole}^{-1}) \times (500 + 273)$$
$$K / (4/3 \ \pi (190 - 35) \text{nm})^3) = 1.79 \times 10^7 \text{ Pa} = 177 \text{ atm}$$

Thus, the formation mechanism of double-layer hollow particles involves two steps: the generation of the silica layer due to the preferred silica condensation reaction along the gas-liquid interface of an aerosol droplet and the formation of the carbon layer by the dehydration and carbonization of dissolved sucrose during the subsequent pyrolysis.

Figure 11:
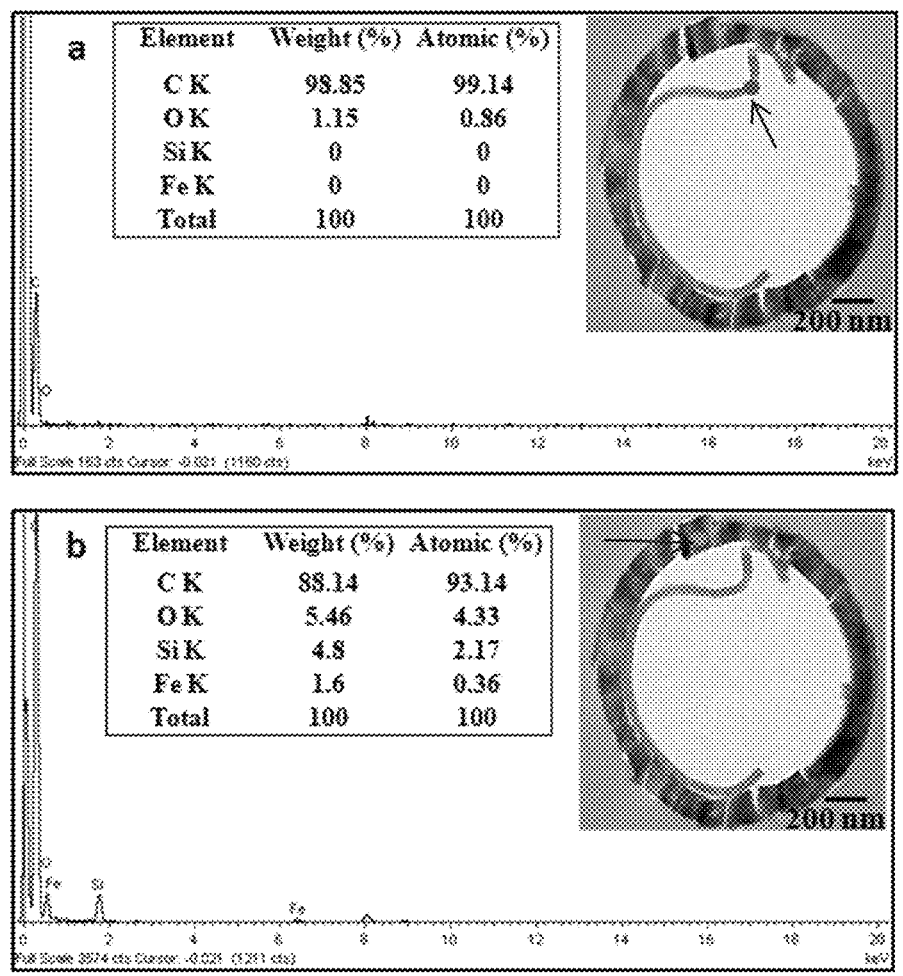
FIG. 11 illustrates energy dispersive spectroscopy (EDS) of exemplary double layer pyrolyzed hollow nanoparticles: (a) the carbon layer of cross section nanoparticles; (b) the silica layer of cross section nanoparticles.
Figure 12:
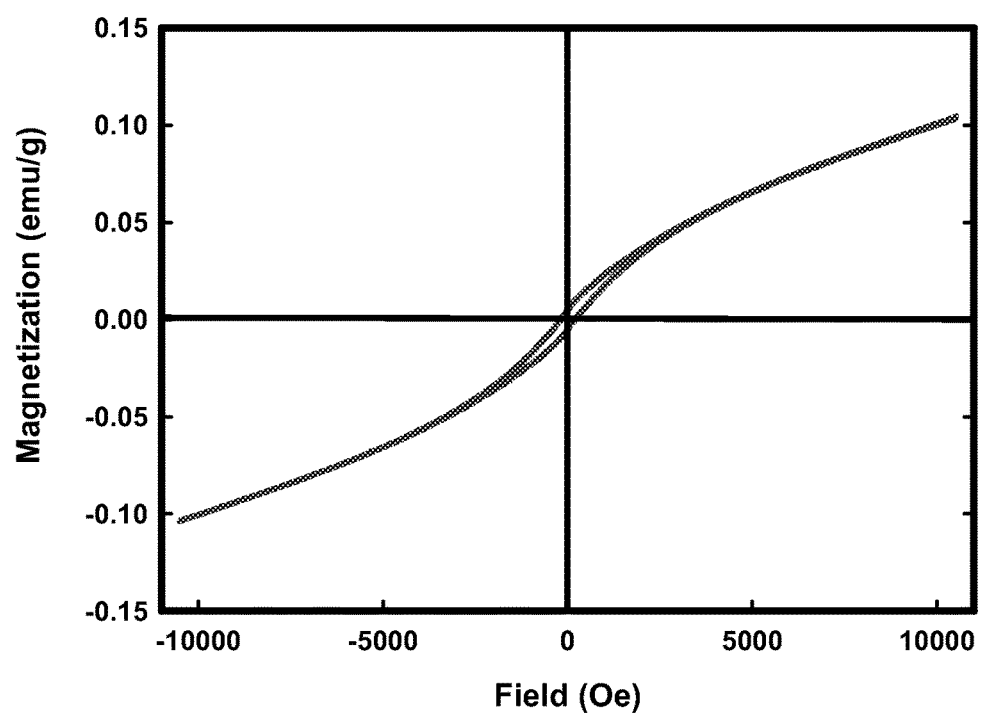
FIG. 12 illustrates a vibrating sample magnetometry hysteresis loop of exemplary double silica carbon layer hollow nanoparticles.

Electron Dispersive Spectrosocpy (EDS) indicates that the silica is confined to the outer layer (with a carbon background from the TEM grid), and carbon to the inner layer. Elemental analysis obtained by X-ray energy dispersive spectroscopy (EDS) of exemplary cross section sample reveals that the atomic ratio of C:O:Si:Fe of the inner carbon layer is 99.1:0.9:0:0, while that of the outer layer is 93.1: 4.3:2.2:0.4 (FIG. 11). In both cases, the carbon level is incidental as the particles are placed on a carbon grid. The noteworthy aspect of the EDS analysis is the lack of silica and iron in the inner layer and the significant presence of silica in the outer layer. Considering the results of EDS, we believe that the inner layer is a carbon layer and the outer layer is a silica layer. The EDS results also indicate that iron is incorporated in the silica layer of the hollow nanoparticles. From the magnetization curve (FIG. 12), it is clear that the double layer nanoparticles display a hysteretic behavior which is consistent with the ferromagnetism given by Fe nanoparticles.

To understand the structural characteristics of these particles further and to prove that the outer layer is silica and the inner layer is carbon, calcination and etching treatments were conducted to selectively remove the inner and outer layers, respectively. The resulting nanoparticles were characterized with SEM and TEM.

Figure 13:
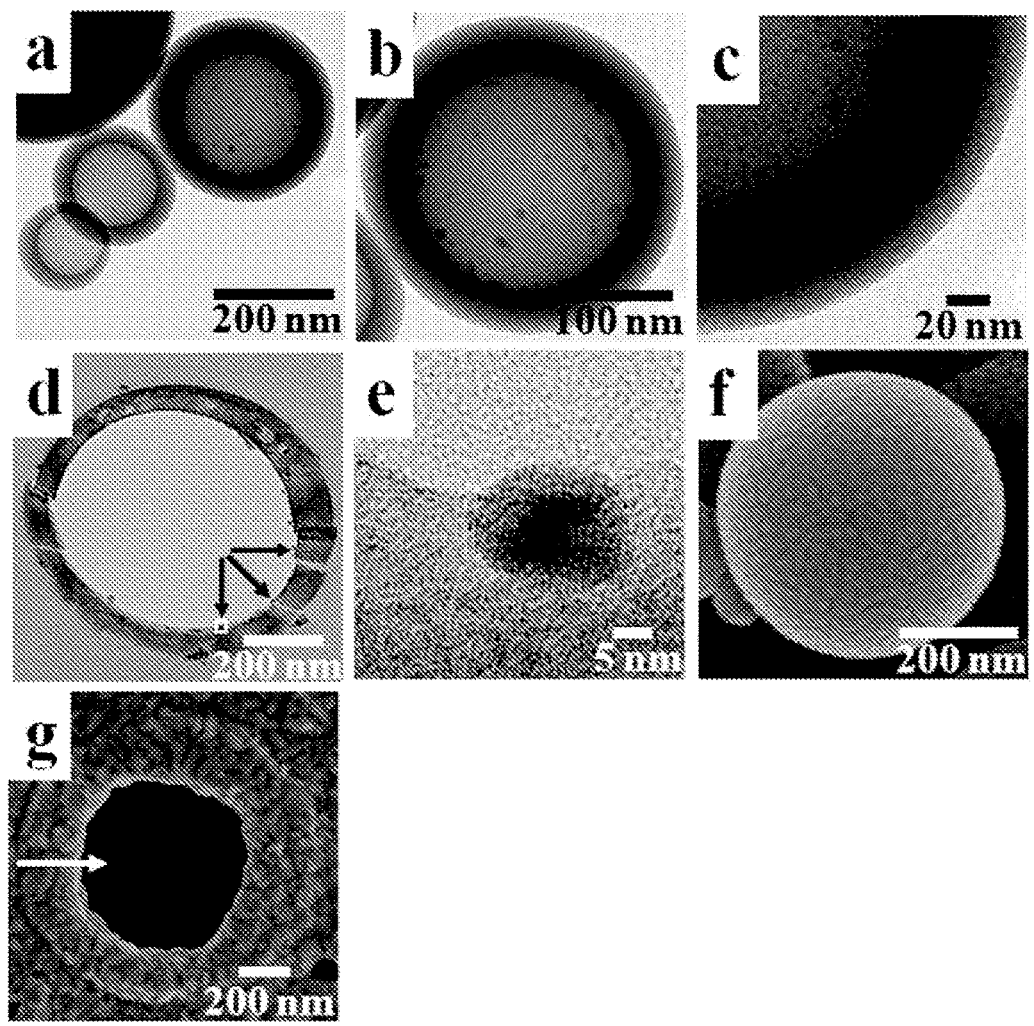
FIG. 13 shows representative electron micrographs of hollow particles with single silica layer shell: (a) TEM image of calcined particles at low magnification; (b) TEM image of a calcined particle at high magnification; (c) HRTEM image of a calcined particle; (d) Cross section TEM image of a pyrolyzed particle, locations of iron species (black dots) indicated by the arrows; (e) HRTEM image of iron species (small white box in panel d shows the location) on hollow particle inner surface; (f) SEM image of a calcined particle; (g) Cross section SEM image of a hollow calcined particle showing a crack-like interior surface.

To remove the carbon layer completely, the pyrolyzed particles were calcined at 500° C. for 3 h and an additional 2 h at 1000° C. The removal of the carbon layer from pyrolyzed particles leads to the morphology transition from double-layer particles to single silica-layer particles (FIG. 13a-c). The cross-sectional TEM (FIG. 13d) shows small dots in the inner periphery of the silica shell with a few within the silica shell. High-resolution TEM (HRTEM)

(FIG. 13e) and energy-dispersive spectroscopy (EDS) of these dots (see FIG. 11) indicate these are iron oxide nanoparticles.

Figure 20:
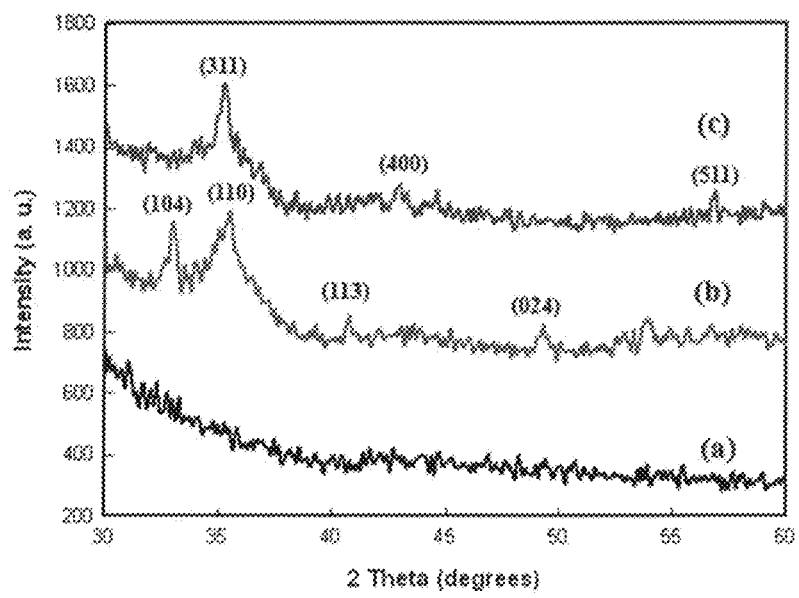
FIG. 20 illustrates XRD patterns (a) double layer particles pyrolyzed at 500° C. for 3 h; (b) particles calcined at 500° C. for 3 h and additional 1000° C. for 2 h; (c) calcined particles are further reduced at 400° C. for 2 h under the flow of $H_2/N_2$ (9% $H_2$).

X-ray diffraction for the double layer particles (FIG. 20, line (a)) implies that the iron species are nanoparticles with an insufficient number of diffraction planes for indexing. After calcination, the pattern (FIG. 20, line (b)) reveals that the peaks of incorporated calcined particles are reasonably consistent with hematite ($\alpha$-$Fe_2O_3$), the most thermodynamically stable polymorph of iron oxide. The peaks at 33.2, 35.6, 40.9, 49.5 2θ correspond to the (104), (110), (113) and (024) planes of hematite, respectively. The XRD pattern of particles after additional reduction at 400° C. for 2 h with 9% $H_2$ flow (FIG. 20, line (c)) can be indexed as magnetite ($Fe_3O_4$).

Figure 37:
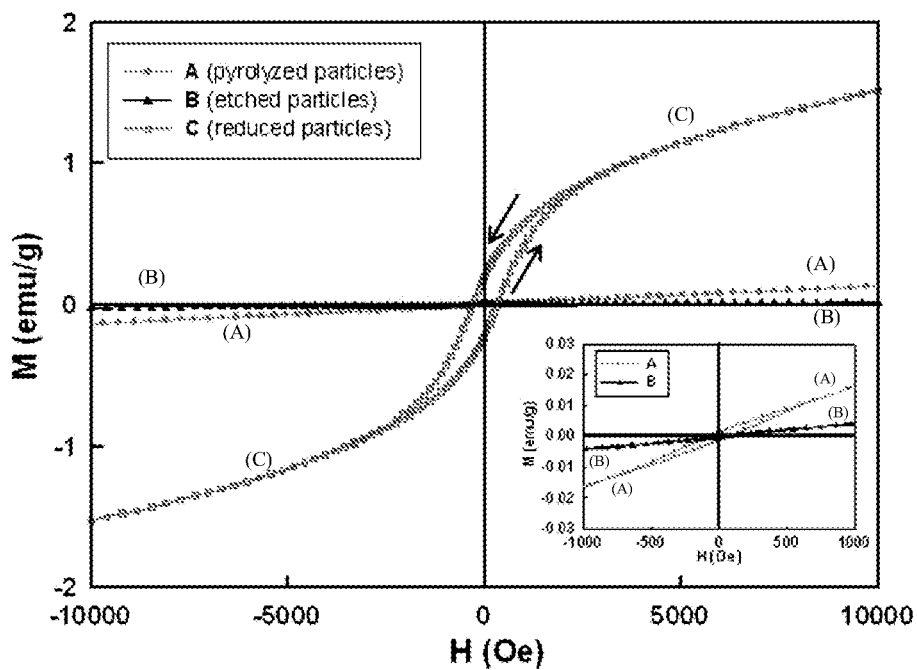
FIG. 37 illustrates magnetic hysteresis loops of pyrolyzed particles (sample A), etched particles (sample B) and particles reduced after calcination to form magnetitie (sample C).

A simple calculation assuming that the composition of the precursor solution is reflected in the relative silicon and iron atomic ratio in the bilayer particles and that the iron oxide particles are approximately 10 nm in diameter indicates that there are approximately 300 iron oxide nanoparticles in each hollow calcined particle. FIGS. 13f, 13g illustrate the external morphology of the particles and the interior of the cut particles, respectively. The system of cracks in the interior (shown by the arrow) may indicate pathways for the egress of $CO_2$ upon calcination of the carbon inner layer. The reduced particles exhibit ferromagnetic hysteretic behavior given by magnetite ($Fe_3O_4$). The magnetic properties of the samples with three different treatments were investigated at 300 K (FIG. 37). The pyrolyzed particles (sample A) display a combination of paramagnetism and weak ferromagnetic behavior (details shown in the inset). The etched particles (sample B) show virtually no magnetization, consistent with the observation that there are essentially no iron species associated with the carbon layer. The particles that are calcined and then reduced to form magnetite show a clear but weak ferromagnetic behavior (sample C). The corresponding remnant magnetization ($M_r$) and coercivity (Hc) of these particles are 0.341 emu/g and 331 Oe, respectively (FIG. 37).

Figure 14:
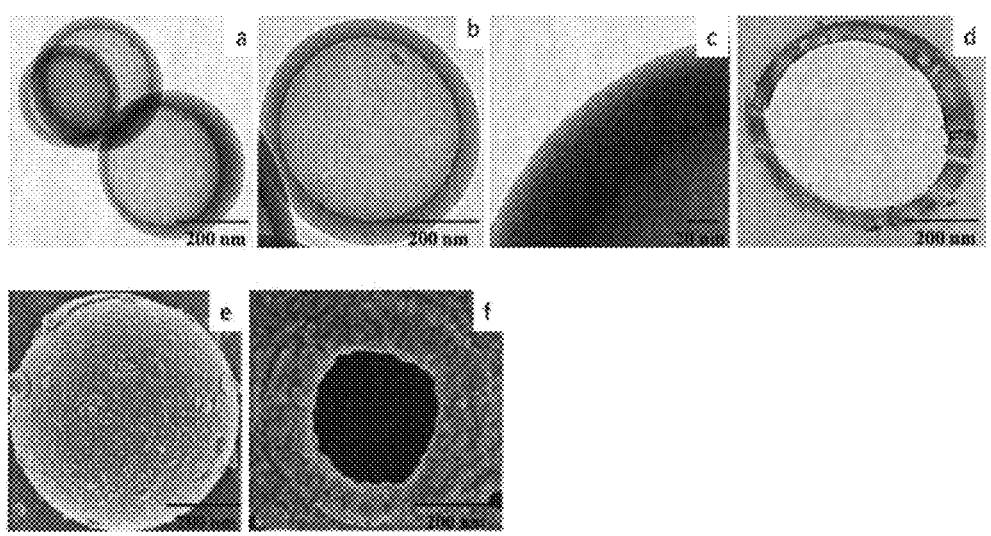
FIG. 14 shows representative electron micrographs of hollow nanoparticles with single silica layer shell: (a) TEM image of calcined nanoparticles at low magnification; (b) TEM image of a calcined nanoparticle at high magnification; (c) High resolution TEM image of a calcined nanoparticle; (d) Cross section TEM image of a pyrolyzed nanoparticle; (e) SEM image of a calcined nanoparticle; (f) Cross section SEM image of a calcined nanoparticle.

During calcinations treatment, oxygen molecules react with inner carbon layer of the nanoparticles and the oxidation product $CO_2$ diffuses out of the hollow nanoparticles. The complete removal of carbon layer of hollow nanoparticles was confirmed by TEM. The removal of carbon layer from pyrolyzed nanoparticles leads to the morphology transition from double layers nanoparticles to single silica layer nanoparticles (FIGS. 14a and 14b). From TEM observation (FIG. 14c), it is clear that the thickness of the single silica layer is approximately 60 nm, which is consistent with double layer nanoparticles. The cross section TEM images also show that the particle has single layer nature with few black dots located at both inner and outer surface (FIGS. 14d and 14e). The cross section SEM image (FIG. 14f) provides further confirmation of the single layer hollow nanoparticle after calcination.

Figure 15:
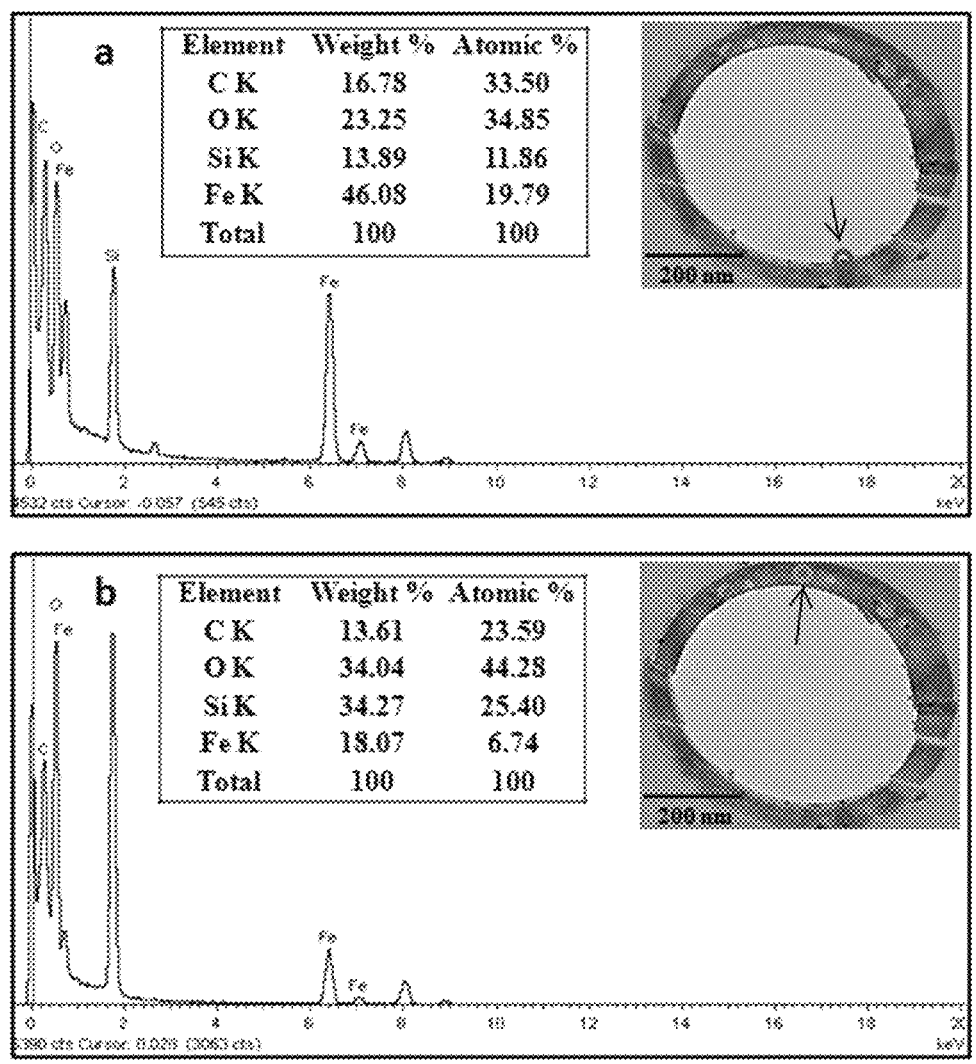
FIG. 15 illustrates EDS of calcined hollow particles: the cross section TEM images show the locations where EDS is acquired. (a) the circle focuses on a small particles represented by the tiny black dots (b) the circle focuses on the silica matrix.

In addition, the EDS results of calcined particles (FIG. 15) demonstrate that the atomic ratio of iron to silicon of the black dots on the inner surface is 19.8:11.9, while that of other area is 6.74:25.4. EDS result (FIG. 15) of these dots area demonstrates that they have significantly higher Fe atomic percentage (19.7%) than other area (6.74%), indicating that the calcination process converts the ionic iron into incorporated iron oxide nanoparticles. Considering these results, we conclude that the tiny black dots are iron oxide particles. Again, we discount the carbon levels as the particles are on a carbon grid.

Figure 16:
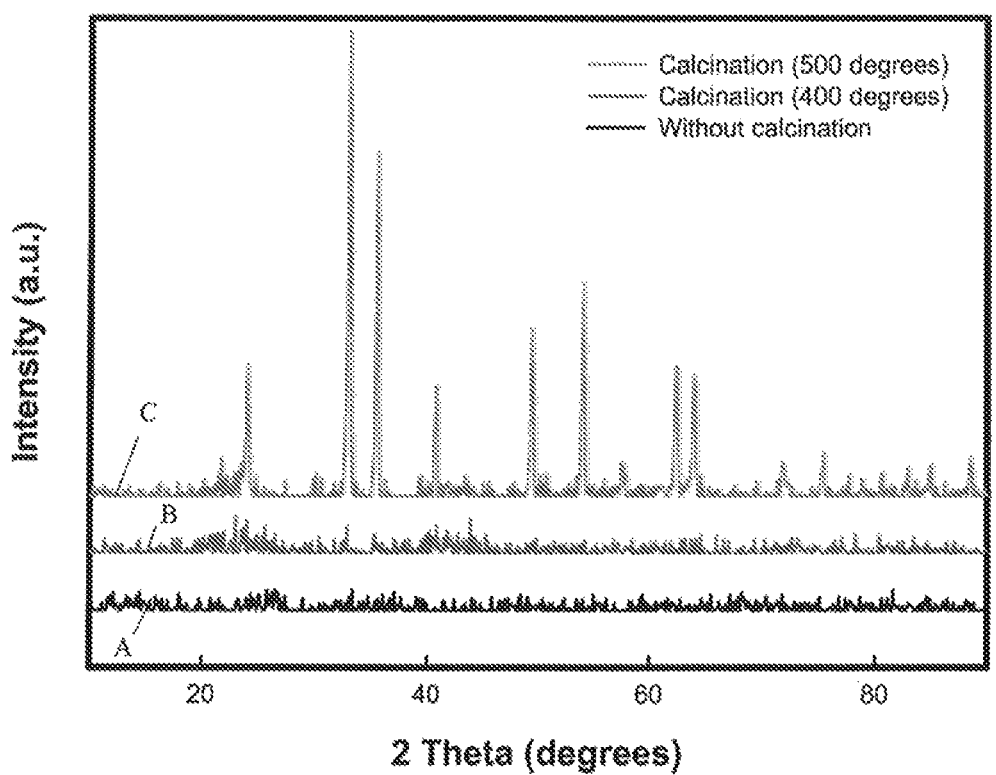
FIG. 16 illustrates representative XRD patterns of nanoparticles after different treatments: solid line identified as A for double layer nanoparticles without calcinations; solid line identified as B for nanoparticles treated with calcination at 400° C.; solid line identified as C for nanoparticles treated with calcination 500° C. (the XRD pattern can be indexed as Hematite ($\alpha\text{-}Fe_2O_3$).

X-ray diffraction (FIG. 16) reveals that the peaks of the incorporated nanoparticles are well consistent with hematite ($\alpha$-$Fe_2O_3$), the most thermodynamically stable polymorph of iron oxide. Meanwhile the strongest peak from the (1 0 4) plane of $\alpha$-$Fe_2O_3$ is centered at 2θ=33° with d-spacing of 2.70 Å. The average size of hematite crystallites deduced from Sherrer's equation for the most intense peak is found to be 16 nm.

Figure 17:
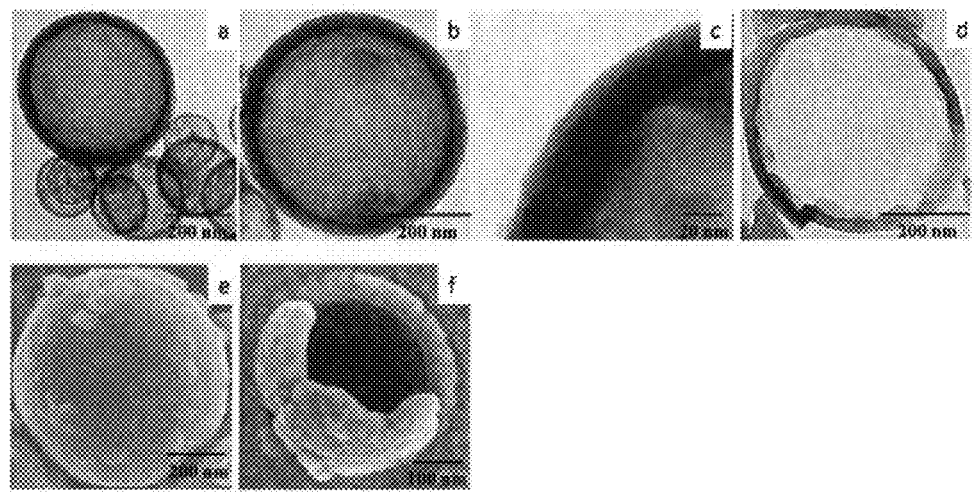
FIG. 17 shows representative electron micrographs of hollow nanoparticles with single carbon layer shell: (a) TEM image of an etched nanoparticles at low magnification; (b) TEM image of an etched nanoparticle at high magnification; (c) High resolution TEM image of an etched nanoparticle; (d) Cross section TEM of an etched nanoparticle; (e) SEM image of an etched nanoparticle at high magnification; (f) Cross section SEM image of an etched nanoparticle at low magnification.
Figure 18:
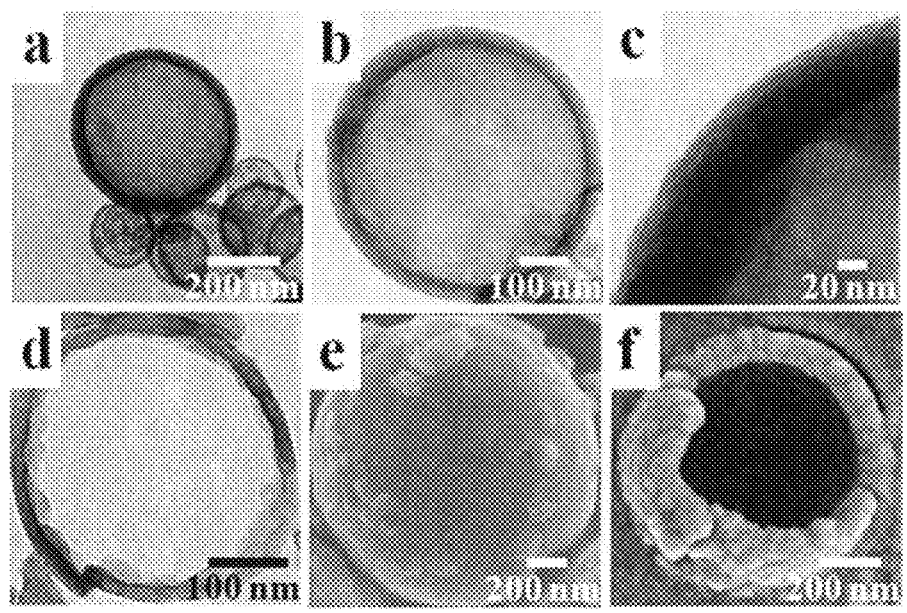
FIG. 18 shows representative electron micrographs of hollow particles with a single carbon layer shell: (a) TEM image of etched particles at low magnification; (b) TEM image of an etched particle at high magnification; (c) HRTEM image of an etched particle; (d) Cross section TEM of an etched particle; (e) SEM image of an etched particle; (f) Cross section SEM image of an etched particle.
Figure 19:
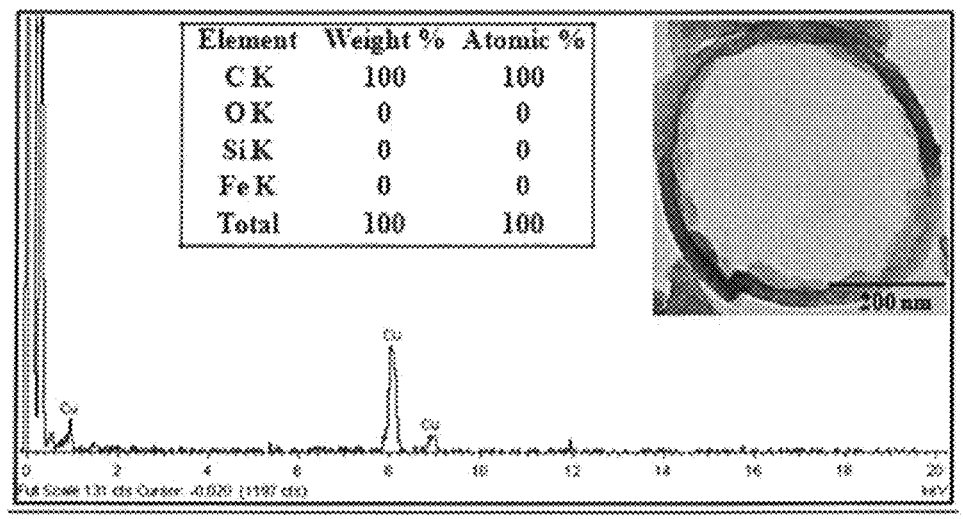
FIG. 19 illustrates EDS of etched hollow particles. Inserted cross section TEM image shows the location (black dot) where EDS is acquired.

To remove the silica layer from the double layer hollow particles, the pyrolyzed nanoparticles may be etched using 10% (v/v) HF solution (or other highly acidic solution such as HCl, sulfuric acid, or other highly acidic solution that a person having ordinary skill in the art would know or discover through routine experimentation) for 48 h. The silica layer of hollow nanoparticles reacts with HF solution, giving rise to $H_2SiF_6$, which can be washed out using deionized water. Silica can also be etched out also using a highly basic solution of for example NaOH, though one could use other highly basic solutions such as ammonium hydroxide, or other highly basic solution that a person having ordinary skill in the art would know or discover through routine experimentation. The representative TEM images (FIGS. 17a-c, 18a-c) of hollow nanoparticles after etching clearly demonstrate that the particles only have single layer structure, implicating the removal of silica layer by HF solution and preservation of hollow carbon microspheres. Additionally, the low magnification TEM image (FIG. 17a) indicates that the single layer nanoparticles are polydisperse, which is associated with aerosol synthesis process. EDS results (FIG. 19) of these nanoparticles demonstrate 100% carbon atomic percentage, indicating the complete removal of silica layer and its incorporated iron by etching treatment. There is no evidence of iron particles on the electron micrograph, and XRD also does not show the presence of iron species, indicating that the iron is confined to the silica and the silica-carbon interface. To further confirm these findings, the etched hollow nanoparticles were cut using Leica Microtome and their corresponding cross section SEM and TEM images were acquired (see FIGS. 17d and 18d). They show that the nanoparticles are hollow in nature with only single layer. Meanwhile, the regular SEM images indicate that the etched hollow carbon nanoparticles have some observable buds on their surface, which may be resulted from the gradually sucrose diffusion during high temperature aerosol process.

The cross section TEM shown in panels 17d and 18d illustrate an almost intact ring, as it is difficult to section without breaking the particle. Panels 17e and 18e show the SEM of the external morphology of an etched particle and panels 17f and 18f indicate the SEM of the cross section of a particle after a single cut to demonstrate that the particles are indeed hollow.

Figure 21:
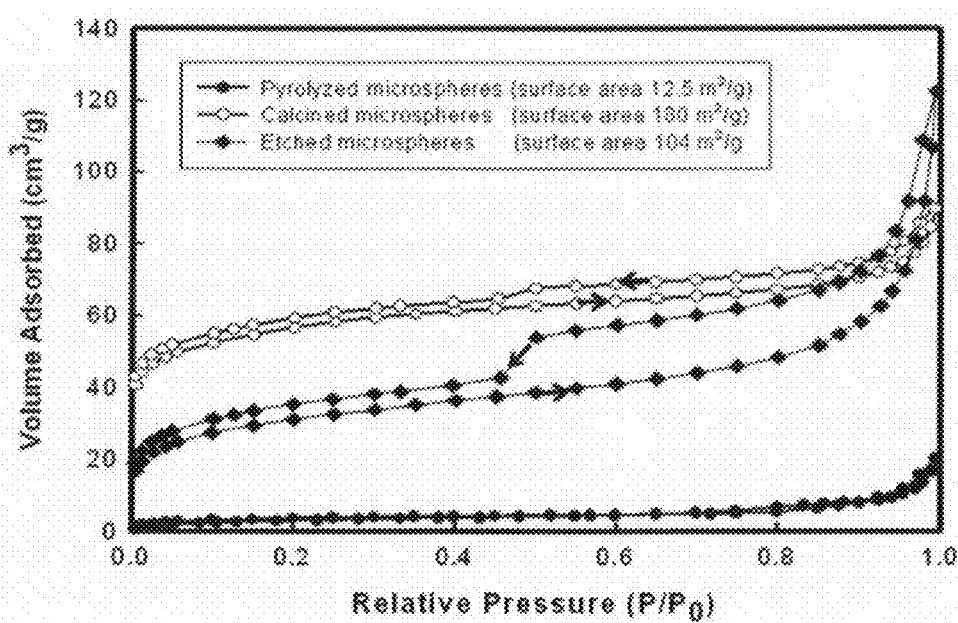
FIG. 21 illustrates nitrogen adsorption-desorption isotherms: (a) pyrolyzed hollow particles (black solid dots (●), BET surface area 12.5 $m^2/g$, the corresponding BJH desorption pore volume 0.0279 $cm^3/g$); (b) etched hollow particles (black solid diamonds (♦), BET surface area 104 $m^2/g$, the corresponding BJH desorption pore volume 0.162 $cm^3/g$); (c) calcined hollow particles (white hollow circles (o), BET surface area 180 $m^2/g$, the corresponding BJH desorption pore volume 0.112 $cm^3/g$).

FIG. 21 shows the $N_2$ adsorption isotherm obtained from the pyrolyzed double layer hollow particles. The surface area for these particles at 77 K was calculated using Brunauer-Emmet-Teller (BET) method. The BET surface area of double-layer hollow particles was found to be 12.5 $m^2/g$ and the corresponding Barret-Joyner-Halenda (BJH) desorption pore volume was determined to be 0.0279 $cm^3/g$. Upon calcination to silica hollow particles or etching to the carbon hollow particles, the surface areas increase to 180 $m^2/g$ (single silica layer) and 104 $m^2/g$ (single carbon layer), respectively (FIG. 21). The low surface area of the double-layer hollow particles implies the minimal porosity of the double-layer particles with pores opening up as the carbon is burnt away or the silica is etched away. Our interpretation is that the pores in the silica are essentially clogged with carbonaceous species during the pyrolysis step to produce the bilayer particles. Upon calcination, the burnoff of carbon exposes the silica pores. Etching away the silica exposes the intrinsic porosity of carbon. The lack of high porosity in the solid is to be expected since the materials are not templated to highly porous structures by the surfactant.

It should be pointed out that the dense, low-porosity silica outer layer of nanoparticles is due to the fact that the relative amounts of free CTAB is not high enough compared to TEOS to template mesoporous silica. The dense silica outer layer of nanoparticles also suggests a possible mechanism for inner carbon layer formation. During pyrolysis, the escape of organic gases in the nanoparticles through the dense silica structure may force the carbonaceous species to the silica wall resulting in the formation of the inner carbon layer of hollow nanoparticles.

The double-layer hollow particles that contain an internal carbon layer and an outer silica layer have been fabricated by a simple and effective aerosol-based process. The preparation is based on the concept of rapidly forming a silica shell that retains carbon precursors within the interior of the particle. Subsequent pyrolysis jams the carbon as a second layer against the silica shell.

The generation of a silica shell by negating the templating effect of the surfactant is expected to be quite general, allowing the encapsulation of a variety of other components in the interior of the particle. In addition to the generation of a new class of hybrid materials using the aerosol technique, the fact that these systems contain iron makes them magnetically responsive.

It is also possible to add layers to the double shelled particles. Silica is hydrophilic and carbon is hydrophobic, creating an ampiphilic particle. Building additional layers can be done by adding a carbon layer to the silica shell, and then adding a silica coating on the carbon layer. The building of additional layers is done by known layer-by-layer techniques.

Another embodiment of the present invention seeks to control and exploit particle properties through modulating layer thickness as described herein. These materials are expected to have multiple applications because they are able to incorporate the benefits of both carbon and silica and additionally include magnetic materials. Their uses as catalytic materials and in stabilizing emulsions are distinct directions of continuing research.

Applications

The following are some specific applications of these materials. All these applications are elaborated upon in the Lou et al. publication, which is incorporated herein by reference, which is a review of hollow particles.

1. Their use as electrode materials in Li-ion batteries.
2. Their use in catalysis and sensing.
3. Biomedical Applications of drug delivery. We particularly note the photothermic applications.
4. Fuel cell catalysts.
5. Photocatalysis.
6. Self-healing applications.
7. Materials for stabilizing interfaces, such as Pickering emulsions.

The present invention is able to make the hollow particles in large quantities because of the nature of the aerosol process.

None of the prior art processes listed in the literature is able to produce the double shelled particles. Because of the double shell, the present invention has a system that is hydrophilic on the exterior and hydrophobic on the interior. There is a distinct possibility that such systems will provide enhanced properties in catalysis and gas sensing.

The present invention is able to modulate the porosity of the shell particularly in systems with a single shell, going from an entirely nonporous to a porous system.

In addition to the applications listed in the Lou et al. publication, we propose there are environmental applications. There are potential applications to the environmental remediation of chlorinated compounds, of arsenic, and other chemicals, due to the catalytic materials in the hollow particles. Since the particles are hollow, they may have some extremely important applications in the remediation of oil spills. They can be filled with dispersants and sprayed onto oil spills. Such controlled delivery of dispersants can be efficacious in breaking up oil spills and dispersing the droplets. Additionally, the particles can be stabilized at an oil water interface to stabilize emulsion droplets. Finally the iron oxide within the particles makes them magnetically responsive and it may be possible to recover the oil through the formation of Pickering emulsions.

The hollow particles can be used to store agricultural pesticides which can be sprayed onto plants for controlled release.

The hollow particles can be used to store fertilizers which can be injected into the ground for controlled release. They can be temperature tuned by coating them with a wax that melts as the temperature increases in the growing season, releasing the fertilizer contents.

The hollow particles can be used to store enzymes for the biological breakdown of organophosphorous compounds. In application, these could be used against nerve agents.

Experimental Procedure

Synthesis of Hollow Silica-Carbon Bilayer Nanoparticles.

All chemicals are commercially available and were used as received. TEOS is used as the silica source and sucrose is used as the carbon source, together with ferric chloride and the surfactant (CTAB). Alternatively, the carbon source can be a monosaccharide or polysaccharide, such as sucrose (most preferable), glucose, cellulose, or cyclodextrins. Alternatively, the surfactant can be cetyltrimethyl ammonium bromide (CTAB), cetyltrimethyl ammonium chloride (CTAC) or other CTA-halides. Alternatively, instead of the silica source, zirconia, alumina or titania can be used.

Figure 1:
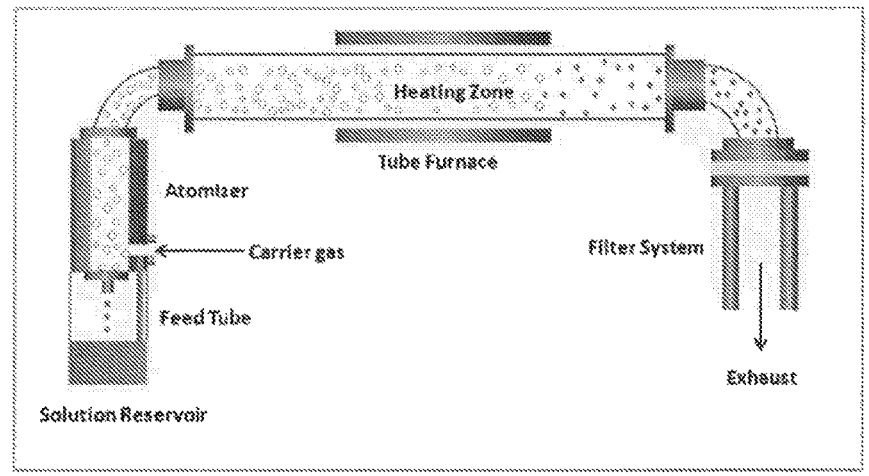
FIG. 1 illustrates an exemplary schematic of an aerosol based process to make submicron particles.
Figure 2:
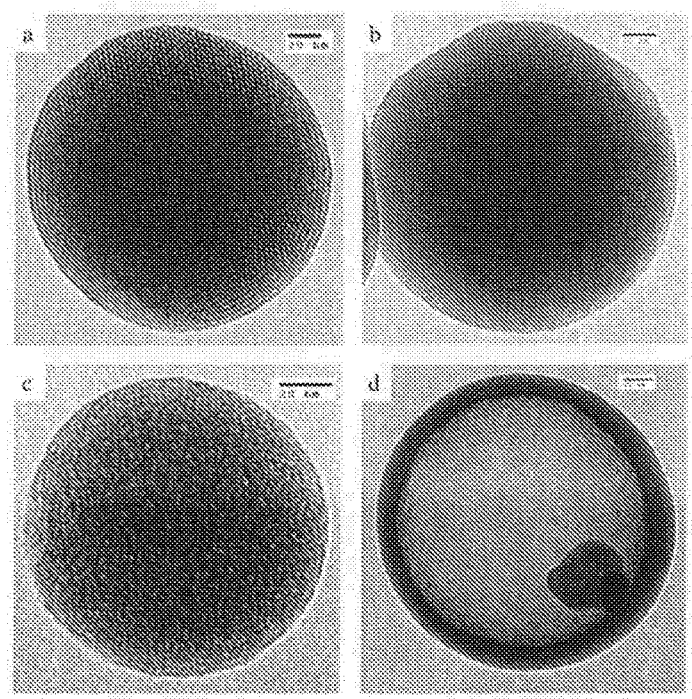
FIG. 2 illustrates exemplary TEM images of calcined particles synthesized with 1.1 g CTAB and 0 g (a), 0.15 g (b), 0.8 g (c) and 0.9 g (d) of $FeCl_3$. The scale bars are 20 nm in all the images.
Figure 3:
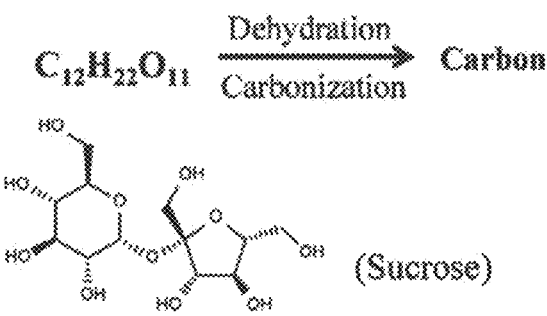
FIG. 3 illustrates one example of the carbon source.

In a typical synthesis, about 0.8 g-1.9 g, preferably 0.95 g, of $FeCl_3.6H_2O$ was first dissolved in 15 mL ethanol under vigorous stirring. Then about 0.1 g-2.2 g, preferably 1.1 g, of CTAB and about 1.0 mL-9.0 mL, preferably 4.5 mL, of TEOS were added to the solution, followed by 1.8 mL of a 0.1 M HCl solution and the dissolution of about 0.01 g-3 g, preferably 1.0 g, of sucrose. The resulting solution was then aged for 0.5 h and atomized using a commercial atomizer (Model 3076, TSI Inc.) to form aerosol droplets, which were passed through a quartz tube placed in a furnace (FIG. 1). The temperature of the heating zone was held at 400° C., and the entering gas pressure of $N_2$ was adjusted to yield a droplet residence time of about 15 seconds through the furnace. During passage through the heating zone, sucrose carbonization and silica condensation reactions occurred. The as-synthesized particles were collected by a filter system and then pyrolyzed at 500° C. for 3 h under the flow of $N_2$ gas.

It is noted that during passage through the heating zone, the coassembly of CTAB with silicate and the formation of mesoporous silica are disrupted by the preferential partitioning of CTAB on intermediate iron species such as FeO(OH). This salt bridging between the iron salt and CTAB locks the CTAB within the interior of a rapidly forming silica shell.

Synthesis of Hollow Silica Nanoparticles.

To obtain the single silica layer particles, the pyrolyzed particles were calcined at 500° C. for 3 h and additional 1000° C. for 2 h in air.

Synthesis of Hollow Carbon Nanoparticles.

To obtain the single carbon layer particles, the pyrolyzed particles were incubated with 10% HF solution for 48 h to remove silica layer.

Characterization

The morphology of the particles was characterized by field emission scanning electron microscopy (SEM, Hitachi S-4700, operated at 20 kV) and transmission electron microscopy (TEM, JEOL 2010, operated at 200 kV). The crystal phases present in the particles were identified using X-ray diffraction (XRD, Siemens, D 500, using Cu αK radiation at 1.54 Å.). The cross section samples for SEM and TEM were prepared by embedding particles within a resin (Embed 812) in 70° C. for 48 h and cut by a Leica ultracuts Microtome. Magnetic properties were characterized using a superconducting quantum interference device (SQUID, MPMS Quantum Design Inc.). The BET surface area of the particles was measured using the nitrogen sorption technique at 77K (Micromeritics, ASAP 2010).

While the double layer hollow particles constitute the key finding, there other aspects based on expanding on the conjecture that we can rapidly create a silica shell by preventing the templating effect of CTAB through salt bridging with $FeCl_3$.

Thin Silica Shells-Template-Free Synthesis of Ultrasound Responsive Hollow Silica Microspheres with Ultrathin Nanometer-Scale Shell Structures Novel ultrathin hollow silica microspheres have been synthesized using aerosol based process with reduced silica precursor loading (tetraethyl orthosilicate, TEOS). Hollow silica microspheres with ultrathin silica shell about 5 nm to 20 nm; or 7 nm to 20 nm, or 7 nm to 15 nm, for example 10 nm-15 nm are also conveniently cracked using ultrasonic treatment, which is one of the most promising external triggers. The ultrathin calcined hollow silica microspheres are presumably fractured by the transient cavitation, a well-known phenomenon of ultrasonication. In addition, the pore size of hollow silica microspheres can be uniquely adjusted by introducing sodium chloride into precursor solution. For example, pore sizes of 0.5 nm to 100 nm, for example 10 nm, in diameter can be obtained by with a NaCl:precursor solution ratio of 0.1:1.0 to 10:1.0. The microspheres with locked-in magnetic iron oxide open up further opportunities in magnetic stimuli responsive applications.

Figure 22:
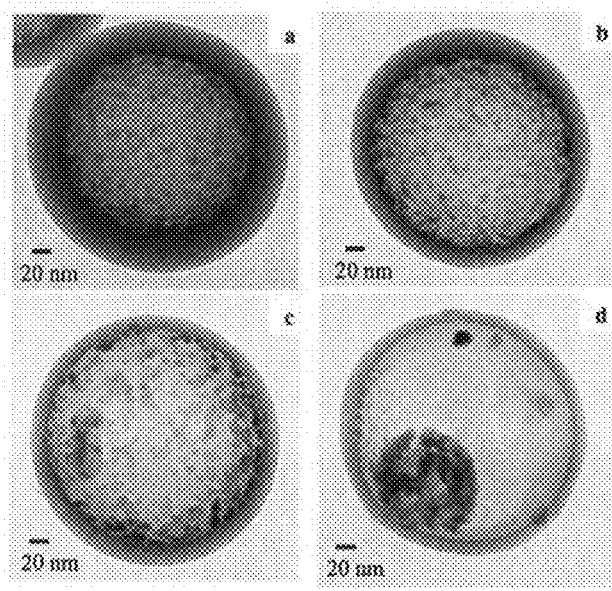
FIG. 22 shows representative electron micrographs of calcined hollow silica microspheres: (a) TEM image at Fe:Si molar ratio of 1:13; (b) TEM image at Fe:Si molar ratio of 1:8; (c) TEM image at Fe:Si molar ratio of 1:6; (d) TEM image at Fe:Si molar ratio of 1:2.7.
Figure 23:
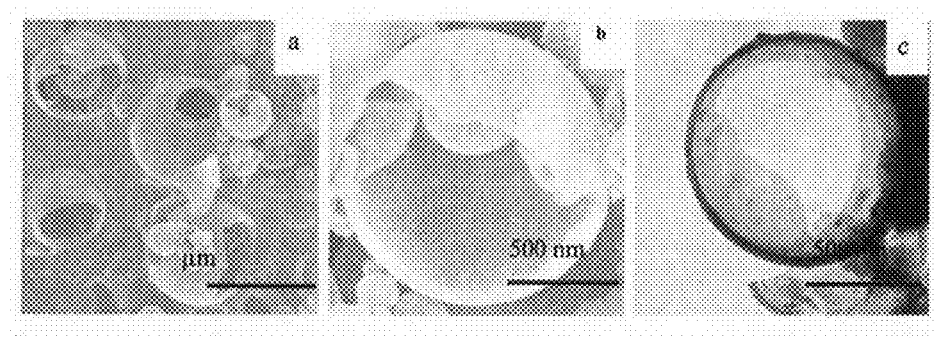
FIG. 23 shows representative electron micrographs of calcined hollow silica microspheres with Fe:Si molar ratio of 1:2.7 after ultrasonication treatment: (a) SEM image at low magnification; (b) SEM image at high magnification for a microsphere; (c) TEM image of a microsphere.
Figure 24:
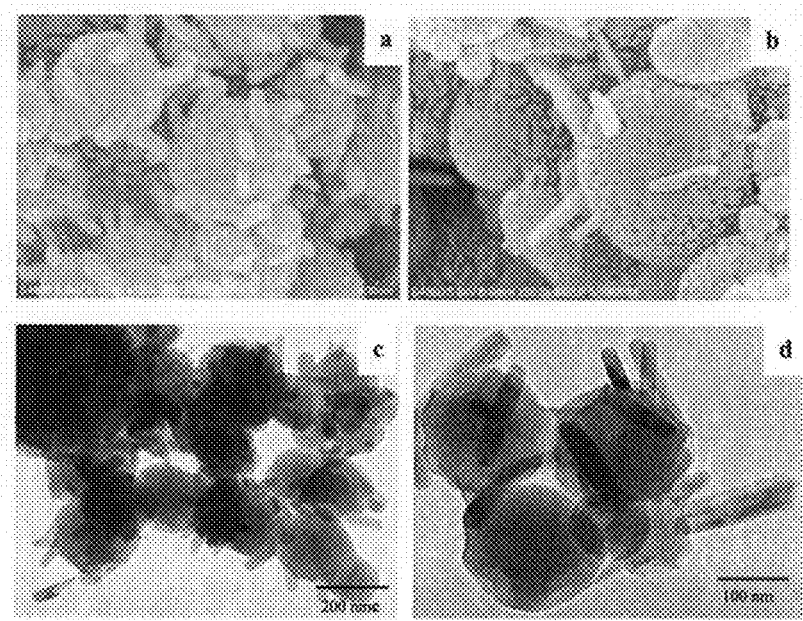
FIG. 24 shows exemplary nanoparticles with protrusions where increasing the sucrose concentration leads to the development of protrusions in the particles

In some embodiments, with decreased levels of tetraethoxy silane (TEOS) in the precursor, the silica shells become progressively thinner till we get shells that are about 5 nm-20 nm thin, for example 10-15 nm thin as shown in panel d of FIG. 22. Below this thickness it is difficult to prepare particles with the requisite consistency. Ultrasonication (150 watts power) easily results in the breakage of the particles as observed in FIG. 23. These "eggshell" type particles in principle can be developed into systems that release their contents as a burst through ultrasound induced rupture. We note that the systems of FIGS. 22 and 23 do not include a carbon precursor (sucrose). In some embodiments, a carbon precursor may be included for a double layer particle.

Hollow microspheres with controlled morphologies are of extensive interest due to their wide applications including encapsulation, biomolecule separation, catalysis, super-capacitors, gas sensing, drug delivery and energy storage. Recently, the research of hollow microspheres has been focused on design of complex structures, such as double shelled, rattle like and yolk shell structures. A variety of chemical strategies to synthesize such hollow microspheres have been applied, including the soft-template and hard-template processes. Particularly the hard template method, the most common route, requires building a desirable layer around a core and followed by the core removal by chemical etching or high temperature calcination.

Ultrasound is one of the most promising external triggers for encapsulated chemical release that can be accurately controlled by parameters, such as frequency, power density as well as duration. Although there are available methods for hollow microspheres preparation, the synthesis of ultrathin hollow microspheres that can be easily cracked by ultrasonic treatment is seldom reported. Therefore the present invention discloses a novel method to prepare ultrathin hollow microspheres and their potential applications.

It is well-known that surfactant cetyl trimethylammonium bromide (CTAB) typically templates highly ordered mesoporous silica through aerosol method when precursor solution contains silica source such as TEOS. However the present invention shows that the introducing of ferric chloride into the precursor solution disrupts the co-assembly of silicate and surfactant CTAB by preferential partitioning of CTAB and more positively charged ferric chloride under acidic condition. The iron chloride ties up the surfactant CTAB so that the silica cannot grow inwards from the surface of the drop, thereby generating hollow particles. The formation of silica rich shell is due to faster silica condensation along the gas-liquid interface of the aerosol droplets and subsequent high temperature calcination remove surfactant CTAB and converts the ferric species into iron oxides. However such synthesized hollow microspheres have relatively thick silica shell that cannot be conveniently ruptured by ultrasound irradiation. Based on this concept, can ultrathin hollow silica microspheres be formed by gradually decreasing silica precursor loading in the solution? Can the synthesized ultrathin silica microspheres be easily cracked by ultrasound treatment, so that encapsulated species can be released to the surrounding?

In the present invention, a simple and efficient aerosol based process is used to synthesize hollow silica microspheres with ultrathin shell thickness (typically approximately 10-15 nm) that can be easily cracked by external ultrasonic irradiation. In addition, the present invention discloses a uniquely tuned pore size on the hollow silica microspheres by conveniently adjusting sodium chloride concentrations in precursor solution.

Experimental

Preparation of Ultrathin Hollow Silica Microspheres

All chemicals are commercially available and were used as received. Alternatively, the surfactant can be cetyltrimethyl ammonium bromide (CTAB), cetyltrimethyl ammonium chloride (CTAC) or other CTA-halides. Alternatively, instead of the silica source, zirconia, alumina, titania or some other ceramic source can be used. In some embodiments, a carbon precursor may be included for a double-layer particle. The carbon source can be a monosaccharide or polysaccharide, such as sucrose (most preferable), glucose, cellulose, or cyclodextrins.

Figure 31:
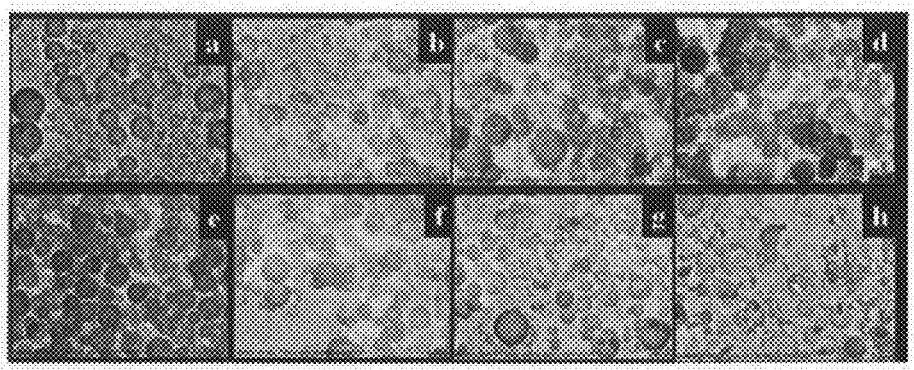
FIG. 31 shows SEM images of calcined microspheres before ultrasonic treatment with Fe:Si molar ratio of (a) 1:13, (b) 1:8, (c) 1:6 and (d) 1:2.7; SEM images of calcined microspheres after ultrasonic treatment with Fe:Si molar ratio of (e) 1:13, (f) 1:8, (g) 1:6 and (h) 1:2.7.

In a typical synthesis about 0.8 g-1.9 g, preferably 0.95 g, of $FeCl_3$ was first dissolved in 15 mL ethanol (95%, v/v) followed by the addition of about 0.1 g-2.2 g, preferably 1.1 g, of cetyltrimethyl ammonium bromide (CTAB). Then various amounts of TEOS (about 1.0 mL-9.0 mL, for example 10, 6, 4.5 and 2 mL) were added to the above solution under vigorous stirring at room temperature. 1.8 mL of 0.1M HCl solution was also added to the solution after 3 minutes stirring. The resulting solution was aged for 30 min and the precursor was then atomized to form aerosol droplets, which were then sent through the dying zone and heating zone of quartz tube. The temperature of the heating zone was held at 400° C. and the resulting particles were collected by a filter system maintained at 80° C. The as-synthesized particles were then calcined at 500° C. for 3 h.

Ultrasonic Treatments of Ultrathin Hollow Silica Microspheres

The parameters of ultrasonication used were set as 20 kHz (frequency) and 150 W (power output). During the experiment period, the ultrasonication probe was dipped into the sample solution. Each sample solution has 5 mg synthesized microspheres dispersed in 1.5 mL deionized (DI) water and was exposed to 5 min treatment in a sonic dismembrator (Fisher Scientific, model 550). The samples were then centrifuged for 10 minutes at 12,000 rpm. The percentage of damaged microspheres was then compared to evaluate the rupture effect.

Tuning Porosity of Hollow Silica Microspheres

Similar to the synthesis of ultrathin hollow silica particles, about 0.8 g-1.9 g, preferably 0.95 g, of $FeCl_3$ was first dissolved in 13.3 mL ethanol followed by the addition of about 0.1 g-2.2 g, preferably 1.1 g, of CTAB. Then 1.0 mL-9 mL, preferably 2 mL, TEOS were added to the above solution under stirring at room temperature. 3.5 mL of 0.1M HCl solution with about 0.01 g-1.0 g, preferably 0.4 g, NaCl was also added to the solution after 3 minutes. The as-synthesized particles from aerosol process were then calcined at 500° C. for 3 h to remove surfactant CTAB and convert iron species to iron oxides. FIG. 39 shows single layer hollow silica particles washed with deionized water, wherein adding salt (NaCl) in the precursor makes the shells porous. Molar ratio of $NaCl/FeCl_3=1/1$.

Dye-Encapsulation Experiment 1 mg hollow silica microspheres were dispersed into 1 mL Rhodamine solution (0.6 mg/mL) and then dried in atmospheric pressure. The dye-loaded microspheres were washed with DI water. Optical and fluorescence images of these samples were examined using inverted fluorescence microscope (model Olympus 1X71).

Hollow Silica Microspheres Characterization

The morphology and structures of the microspheres were evaluated using field emission scanning electron microscopy (SEM, Hitachi S-4700, operated at 20 kV), transmission electron microscopy (TEM), high-resolution TEM (HR-TEM) (JEOL 2010, operated at 200 kV) and X-ray diffraction (XRD, Siemens, D 500, using Cu αK radiation at 1.54 Å.). The specimens for TEM examination were obtained by dispersing microspheres in ethanol (95%, v/v) and drops of microsphere suspension were added onto a copper grid for TEM microscope.

The cross section samples for SEM and TEM were prepared by embedding silica microspheres within resin (Embed 812) in 70° C. for 48 h and cut by Leica ultracuts Microtome. The porosity of the microspheres was evaluated by the nitrogen sorption technique at 77K (Micromeritics, ASAP 2010).

Results and Discussion

The synthesis of ultrathin hollow silica microsphere is achieved through a simple and effective aerosol process, which is illustrated in FIG. 29. Typically, the precursor solution was first atomized to generate aerosol droplets, which were sent through the heating zone where silica dehydration and condensation reactions occurred. The morphology of synthesized hollow silica microspheres was evaluated by TEM and HRTEM. The representative TEM images in FIG. 29 show that these hollow silica microspheres are composed of a large number of spheres with diameter of 100 nm to 3000 nm, and more preferably 100-1000 nm. These images also reveal that these microspheres are of well-defined hollow structures, which show the bright center and dark trim. More importantly, the silica shell thickness of hollow silica microspheres is decreasing with the decreasing of TEOS loading in the precursor solution (FIG. 29*a-d*). In addition, the breakage of small percentage of ultrathin hollow silica microspheres prepared from the lowest TEOS loading (FIG. 29*d*) is noted after calcination treatment. This is reasonable because ultrathin silica shells of some microspheres cannot maintain their structures due to the decomposition of surfactant CTAB during calcination process that generates high internal pressure. It is also interesting to observe that the microspheres have morphology transition from ill-defined hollow structure (FIG. 29*e*) to well-defined hollow structure (FIG. 29*d*) after calcination treatment.

Based on TEM observation with high resolution (FIG. 29*f*), the ultrathin silica shell is not porous amorphous silica in nature. The $N_2$ adsorption desorption isotherm is then used to analyze the porosity of synthesized microspheres. Surface area for these microspheres at 77K is calculated using Brunauer-Emmet-Teller (BET) method. The BET surface area is found to be 13.8 $m^2/g$ which is close to its geometric surface area, indicating that these calcined silica microspheres are almost nonporous.

In order to clearly demonstrate the TEOS loading effect on silica shell thickness, TEM images of hollow silica microspheres made from various TEOS loadings with comparable size (200 nm-1000 nm in diameter, more preferably ~250 nm in diameter) are acquired (FIG. 30*a-d*). Obviously, the TEM images demonstrate that calcined hollow silica microspheres have decreased shell thicknesses with the lowering of TEOS loading. The thinnest shell thickness of silica microspheres from Fe:Si molar ratio of 1:2.7 is measured to be approximately 15 nm, while the thickest one from Fe:Si molar ratio of 1:2.7 is around 40 nm. The formation of silica shell is the result of hydrolysis and condensation of TEOS during the aerosol process. Therefore lower loading of silica precursor is expected to result in thinner silica shell, which is consistent with the observations in FIG. 30. Additionally, calcination treatment of as-synthesized microspheres converts iron species to iron oxides. X-ray diffraction (XRD) reveals that the peaks of incorporated iron oxide nanoparticles are well consistent with hematite ($\alpha$-$Fe_2O_3$), the most thermodynamically stable polymorph of iron oxide. Meanwhile the strongest peak from the (1 0 4) plane of $\alpha$-$Fe^2O^3$ is centered at $2\theta=33°$ with d-spacing of 2.70 Å.

Silica hollow microspheres prepared in different Fe:Si molar ratios (1:13 to 1:2.7) are subject to ultrasonic treatment to evaluate the rupture properties. SEM images in FIG. 31 reveal the external morphology of calcined silica microspheres before and after ultrasonic treatments. It is clear that calcined silica microspheres have well-defined spherical structures with the size of 100 to 1000 nm (FIG. 31*a-d*), which is consistent with characteristic droplet size distribution through aerosol process. Comparing the morphology of these microspheres before and after same ultrasonic treatments, it is interesting to observe that calcined hollow silica microspheres with thicker thicknesses (Si:Fe ratio≥6:1) are intact after ultrasonic treatment (FIG. 31*e-g*), while most of microspheres with ultrathin shell thicknesses (Si:Fe ratio=2.7:1) are ruptured (FIG. 31h) by ultrasound treatment (20 kHz, 150 W). Upon ultrasonic irradiation, ultrathin hollow silica microspheres keep cracking and eventually most of them collapse. This transformation kinetics of ultrathin silica microspheres is fast and it only take 5 minutes for ultrathin microspheres to turn into pieces.

Figure 32:
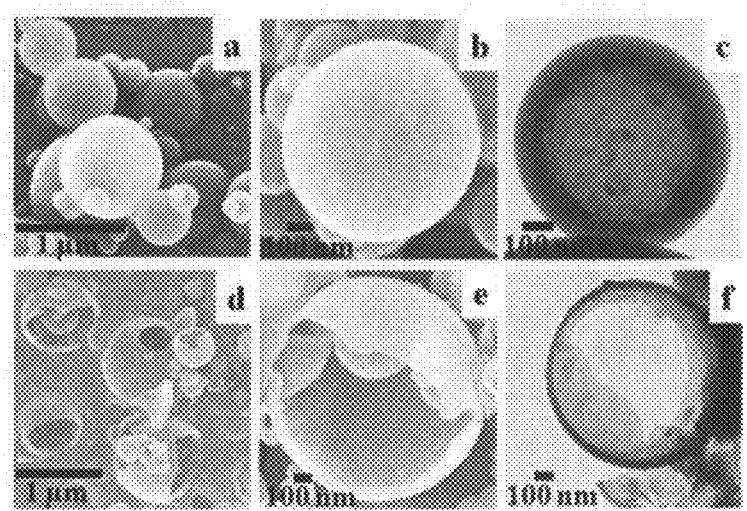
FIG. 32 illustrates representative electron micrographs of calcined hollow silica particles after ultrasonication treatment: (a) SEM image at low magnification with Fe:Si molar ratio of 1:13; (b) SEM image at high magnification with Fe:Si molar ratio of 1:13; (c) TEM image of a calcined particle with Fe:Si molar ratio of 1:13; (d) SEM image at low magnification with Fe:Si molar ratio of 1:2.7; (e) SEM image at high magnification with Fe:Si molar ratio of 1:2.7; (f) TEM image of a microsphere with Fe:Si molar ratio of 1:2.7.

To further reveal the structure of ruptured silica microspheres with ultrathin silica shell triggered by ultrasound, SEM and TEM images of calcined microspheres prepared from Fe:Si ratio of 1:13 and 1:2.7 are obtained and compared (FIG. 32a-f). The hollow silica microspheres (Fe:Si=1:2.7) are stable in air or in the aqueous solution before ultrasonic treatment. However, when an ultrasonic treatment (20 kHz, 150 W) is applied, the hollow silica structures are deconstructed. It is clear that most of silica microspheres (Fe:Si=1:2.7) are ruptured by ultrasound treatment (FIG. 32d-f), while silica microspheres of lower silica content (Fe:Si=1:13) remain intact (FIG. 32a-c). FIGS. 32c and 32f demonstrate that silica microspheres prepared from Fe:Si=1:13 have apparently significant thicker thickness, which can maintain the shell structure upon ultrasonic treatment. The ultrathin calcined hollow silica microspheres are presumably fractured by the transient cavitation, a well-known phenomenon of ultrasonication. In cavitation, extreme conditions of local temperature and pressure are known to exist at rapid heating and cooling rate, which can lead to explosion by gas buildup inside the microspheres and rupture the silica shell of microspheres. Additionally, the ultrasound wave generated by cavitation may accelerate hollow microspheres to high velocities and fracture the ultrathin silica shells.

It appears that a Fe:Si molar ratio of 1:2.7 is ideal for creating thin silica spheres. However, the Fe:Si molar ratio can vary from 0.5:3 to 5:3 and still create acceptable thin silica spheres for sonication destruction.

Figure 33:
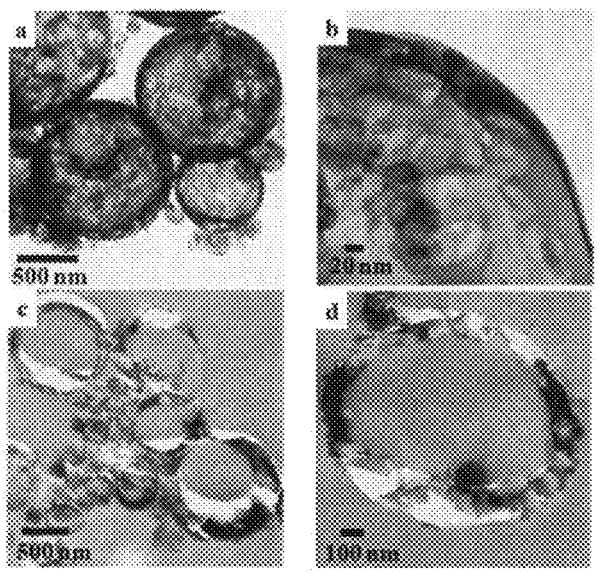
FIG. 33 illustrates representative TEM of calcined hollow silica microspheres: (a) Na:Fe molar ratio of 0.6:1 washed with DI water; (b) Na:Fe molar ratio of 1:1 washed with DI water; (c) cut section TEM at low magnification; (d) cut section TEM at high magnification.

The pore size tunability of hollow microspheres plays an important role in widening their applications. The porosity of hollow silica microspheres can be adjusted by varying the amount of sodium chloride loading while keeping all concentrations of other chemical species same. As shown in FIG. 33a, the introduction of about 0.01-1.0 g, preferably 0.4 g, sodium chloride results in hollow silica microspheres with porous structures. HRTEM reveals the detailed porous structure of the microspheres (FIG. 33b). To further confirm these findings, the hollow silica microspheres were cut using a Leica Microtone. The cut section TEM (FIGS. 33c and 33d) illustrates that these hollow microspheres have less dense area along the rings. The embedding epoxy resin can also be observed inside the particles, which indicates the silica shells are porous enough to let resin diffuse inside these microspheres during cut section TEM preparation.

Figure 34:
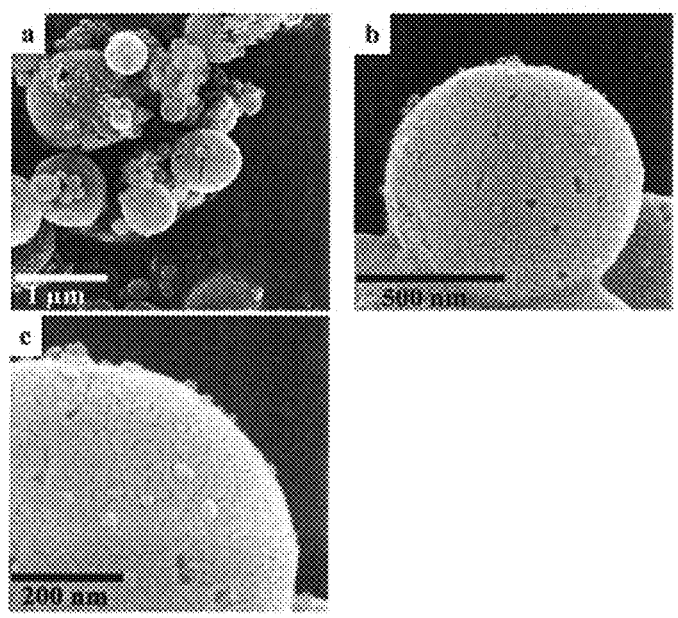
FIG. 34 illustrates representative SEM of calcined silica microspheres: (a) Na:Fe molar ratio of 2:1 washed with water; (b) Na:Fe molar ratio of 2:1 washed with water; (c) high resolution SEM.

The SEM images (FIG. 34) further provide the external morphology of such porous hollow particles. It is clear that these microspheres have irregular shape pores on silica shells, and the size of these pores is in the range of 0.5-100 nm, for example 10 nm. The BET surface area and desorption pore volume of these calcined hollow microspheres are calculated as 33.3 $m^2/g$ and 0.127 $cm^3/g$ respectively (FIG. 35), which are more than twice of those of silica microspheres prepared without sodium chloride. The surface area results demonstrate that introducing sodium chloride in the precursor solution can increase porosity by generating more channels along the silica shell. The mechanism of creating pore channel along the silica shell may be that silica condensation reaction and sodium chloride precipitation occur simultaneously along aerosol droplets.

Figure 35:
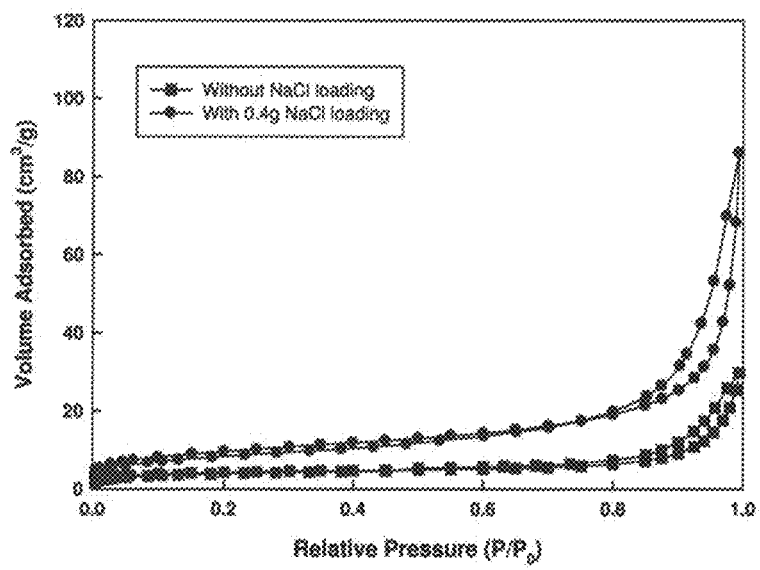
FIG. 35 shows Nitrogen adsorption-desorption isotherms: (a) silica particles without NaCl loading (black solid triangles, BET surface area 13.8 $m^2/g$, the corresponding BJH desorption pore volume 0.043 $cm^3/g$); (b) the silica particles with NaCl after washing (black diamonds, BET surface area 33.3 $m^2/g$, the corresponding BJH desorption pore volume 0.127 $cm^3/g$). (Na:Fe molar ratio is 2:1)

The XRD patterns of two groups of hollow silica microspheres: with and without washing treatments are shown in FIG. 35. It can be seen that silica microspheres before washing have both hematite and NaCl peak patterns, while silica microspheres after washing only have hematite pattern. This clearly indicates that washing procedure can remove NaCl particles on and inside the silica microspheres and therefore open up more available pores.

Figure 36:
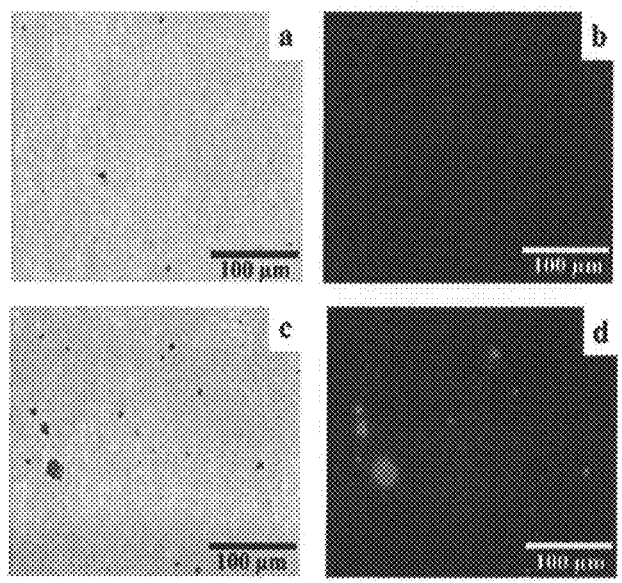
FIG. 36 shows Fluorescent micrographs of silica microspheres (a) Bright image of silica microspheres without NaCl; (b) Fluorescence image of silica microspheres without NaCl; (c) Bright field image of silica microspheres with 0.4 g NaCl; (d) Fluorescence image of silica microspheres with 0.4 g NaCl.

Dye-encapsulation experiments were also conducted by dispersing hollow silica microspheres (with and without sodium chloride loading) into Rhodamine B solution (2 mg/mL). Phase contrast (FIG. 36a, 36c) and fluorescence images (FIG. 36b, 36d) are acquired. The fluorescence images of these microspheres readily show that discrete red shapes (FIG. 36d) for microspheres prepared with sodium chloride, suggesting that rhodamine B molecules are entrapped inside hollow silica microspheres, which supports open pore structure along the silica shell.

The ultrathin hollow silica particles are synthesized through a simple and effective aerosol based process using reduced TEOS loading in the precursor solution. These hollow microspheres with ultrathin shell thickness can be easily ruptured by ultrasonication treatment in a short time via cavitation mechanism, which make them a promising material for ultrasound-triggered release application. The porosity of silica hollow microspheres can be conveniently tuned by introducing sodium chloride due to simultaneous silica condensation and sodium chloride precipitation. The fact that these novel microspheres have ultrathin silica shell makes them ultrasound responsive and expected to have wide range of applications where pulsatile encapsulated release is needed.

In another embodiment of the present invention, a dense carbon particle with a net-like or cage-like thin silica shell can be created. TEOS loading in the precursor solution is reduced to make a thinner silica shell, as seen in FIGS. 40-47. Generally, TEOS loading of 1 mL-2 mL will result in a relatively thick silica shell (about 20-40 nm thick), while TEOS loading of 0.75 mL-1 mL will result in a relatively thin silica shell (about 10-20 nm thick), and TEOS loading of 0.5 mL-0.75 mL will result in a relatively thin silica shell (about 5-7 nm thick), with a net-like or cage-like structure.

Figure 40:
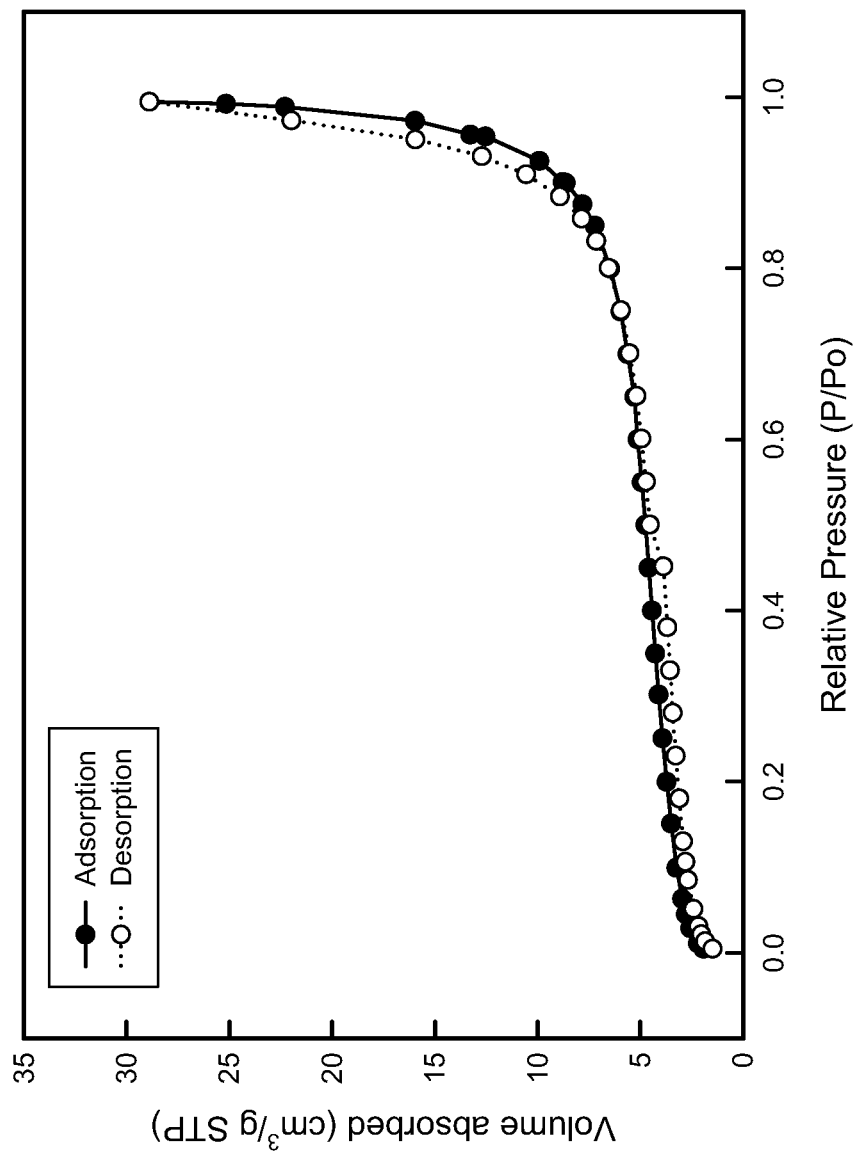
FIG. 40 shows nitrogen adsorption-desorption isotherm with a precursor of 2 ml TEOS and no sucrose after calcination.

FIG. 40 shows nitrogen adsorption-desorption isotherm with a precursor of 2 ml TEOS and no sucrose after calcination. The BET surface area is 13 $m^2/g$.

Figure 41:
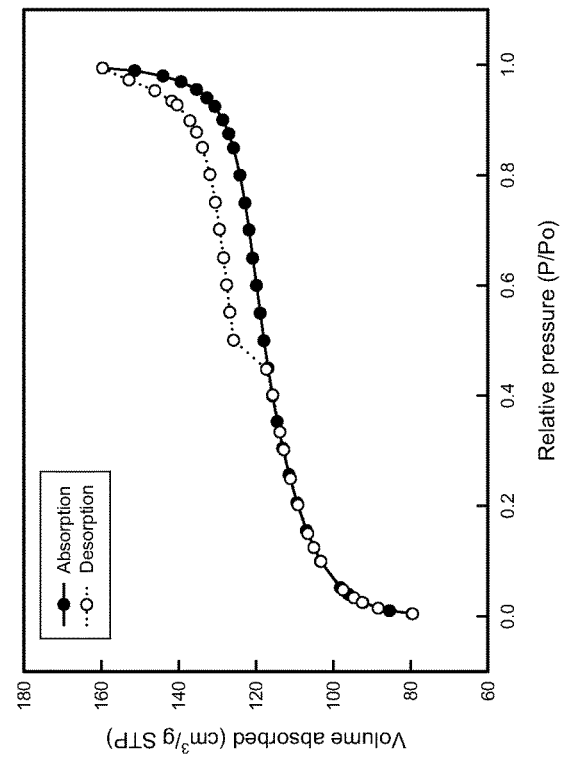
FIG. 41(a)-(b) shows TEM images of particles with a precursor of 2 ml TEOS and 0.5 g sucrose after calcination.
Figure 42:
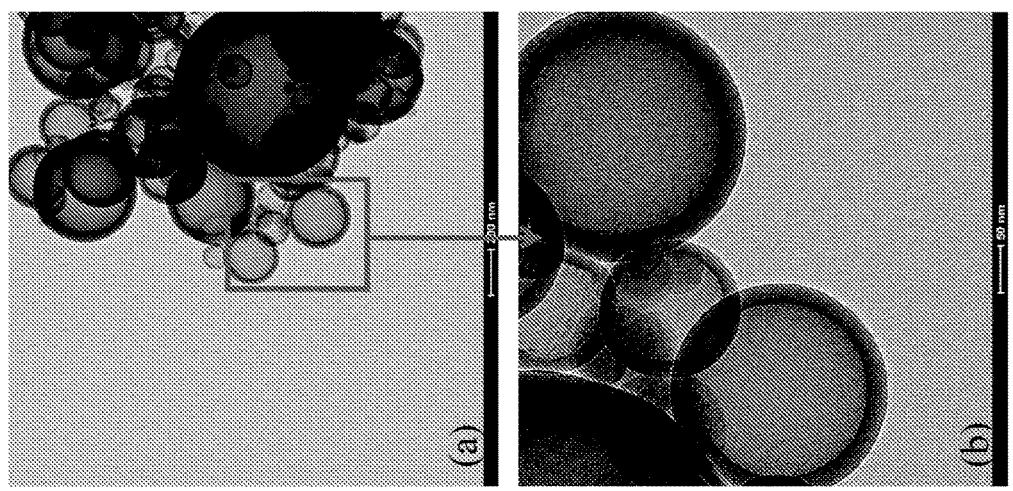
FIG. 42 shows nitrogen adsorption-desorption isotherm with a precursor of 2 ml TEOS and 0.5 g sucrose after calcination.
Figure 43:
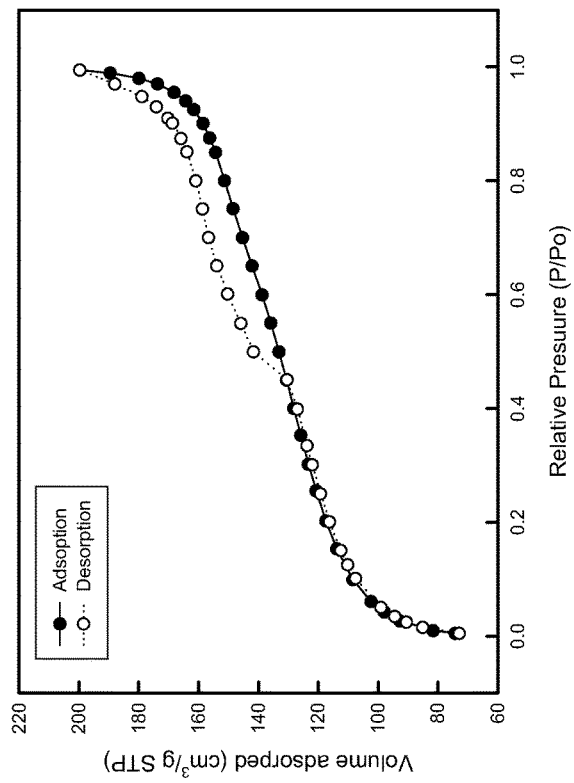
FIG. 43(a)-(b) shows TEM images of particles with a precursor of 1 ml TEOS and 0.5 g sucrose after calcination.

FIGS. 41(a)-(b) and 42 show TEM images of particles and nitrogen adsorption-desorption isotherm with a precursor of 2 ml TEOS and 0.5 g sucrose after calcination. The BET surface area is 339 $m^2/g$. As seen in FIG. 41, with the addition of carbon source-sucrose in the precursor solution, some of the carbon source are mixed within the silica layer during aerosolization. After calcination, carbon is burnt off leaving many pores in the silica shell, hence the particles have very high surface area.

Figure 44:
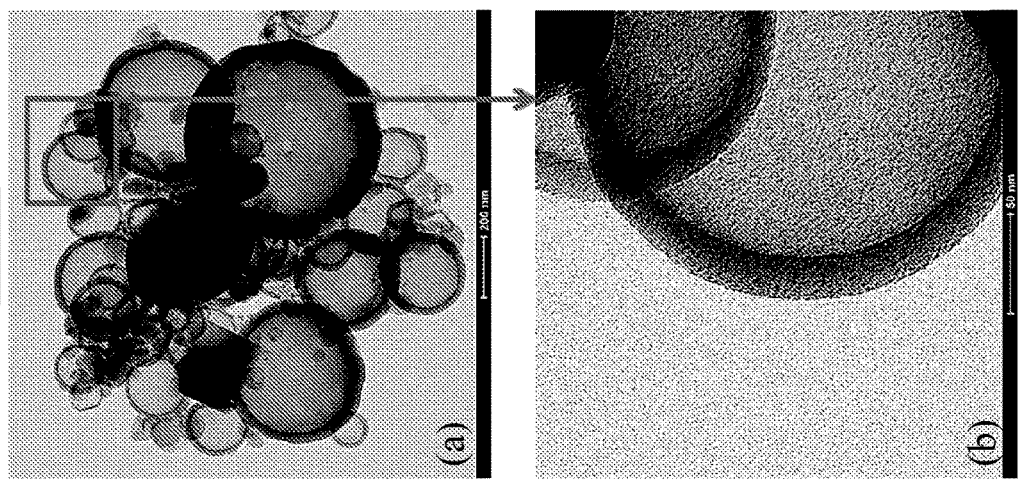
FIG. 44 shows nitrogen adsorption-desorption isotherm with a precursor of 1 ml TEOS and 0.5 g sucrose after calcination.
Figure 46:
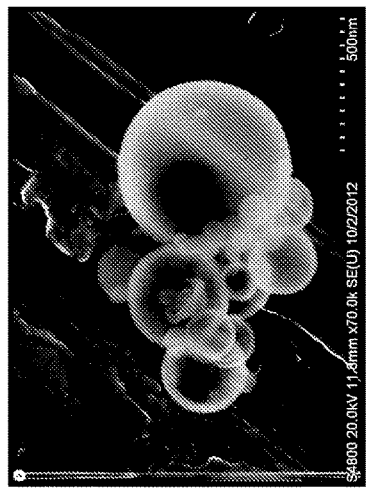
FIG. 46 shows SEM images of particles with a precursor of 0.75 ml TEOS and 0.5 g sucrose after calcination.
Figure 47:
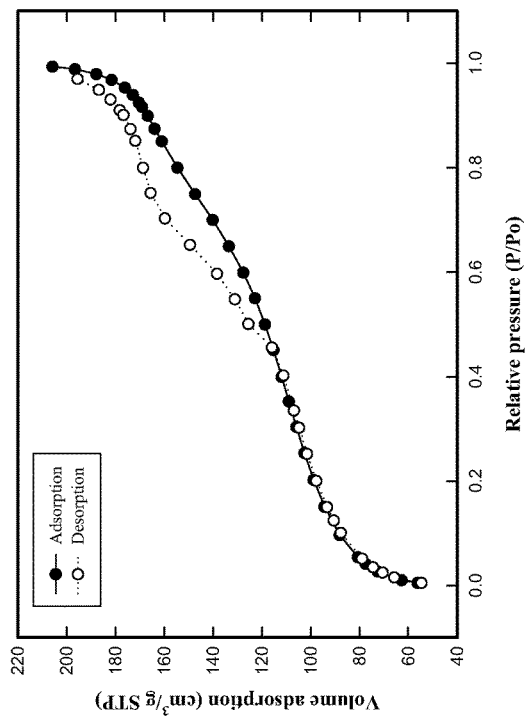
FIG. 47 shows nitrogen adsorption-desorption isotherm with a precursor of 0.75 ml TEOS and 0.5 g sucrose after calcination.
Figure 45:
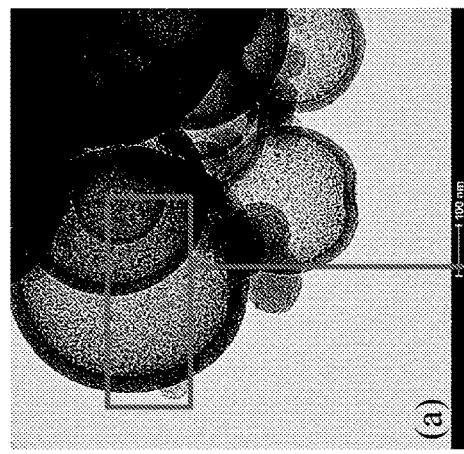
FIG. 45(a)-(b) shows TEM images of particles with a precursor of 0.75 ml TEOS and 0.5 g sucrose after calcination.

FIGS. 43(a)-(b) and 44 show TEM images of particles and nitrogen adsorption-desorption isotherm with a precursor of 1 ml TEOS and 0.5 g sucrose after calcination. The BET surface area is 372 $m^2/g$.

FIGS. 45(a)-(b), 46 and 47 show TEM and SEM images of particles and nitrogen adsorption-desorption isotherm with a precursor of 0.75 ml TEOS and 0.5 g sucrose after calcination. The BET surface area is 323 $m^2/g$.

| T = 400<br>TEOS | P = 10 psig<br>Sucrose | 2 furnaces<br>Observe |
|---|---|---|
| 2 ml | 0 g | Hollow thin shells after calcination. BET surface area is 13 m2/g. |
| 2 ml<br>molar ratio = 6:1 | 0.5 g | Hollow thin shells after calcination (10-40 nm). BET surface area is 339 m²/g. |
| 1 ml<br>molar ratio = 3:1 | 0.5 g | Hollow thin shells after calcination (10-20 nm). BET surface area is 372 m²/g. |
| 0.75 ml<br>molar ratio = 2.3:1 | 0.5 g | Hollow thin shells after calcination (10-20 nm). BET surface area is 323 m²/g. |
| 0.5 ml | 0.5 g | Cannot form spheres. |

With the same TEOS loading (1 ml), when the sucrose in the precursor solution is increasing from 0.5 g to 1 g, the morphology of the particles is changed from hollow to dense spheres. This is because the concentration of sucrose in the aerosol droplet is too high and it obstructs the diffusion of the silica source to the gas-liquid interface. So the silica source is mixed with carbon source and other species forming dense spheres.

Figure 48:
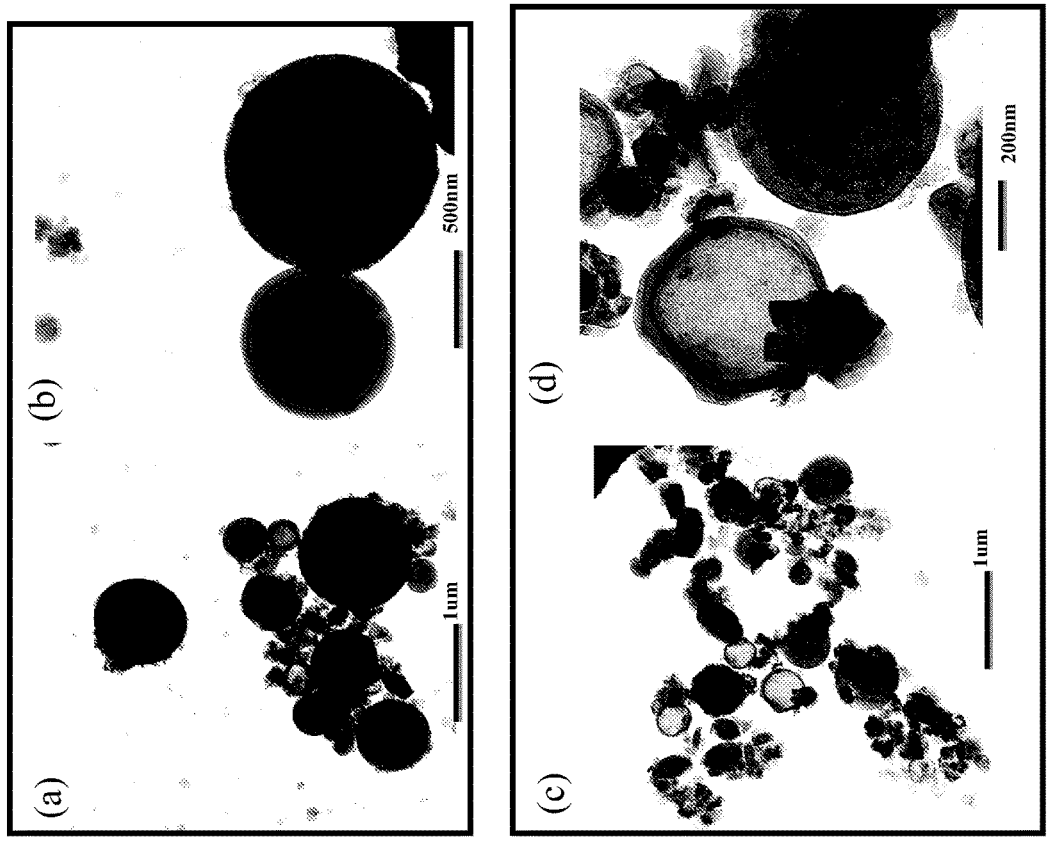
FIG. 48(a)-(d) shows TEM images of particles with a precursor of 1 ml TEOS and 0.75 g sucrose.

FIG. 48(a-d) shows TEM images of particles with a precursor of 1 ml TEOS and 0.75 g sucrose. FIGS. 48(a) and (b) are images of aerosolized particles. FIGS. 48(c) and (d) are images of calcined particles.

Figure 49:
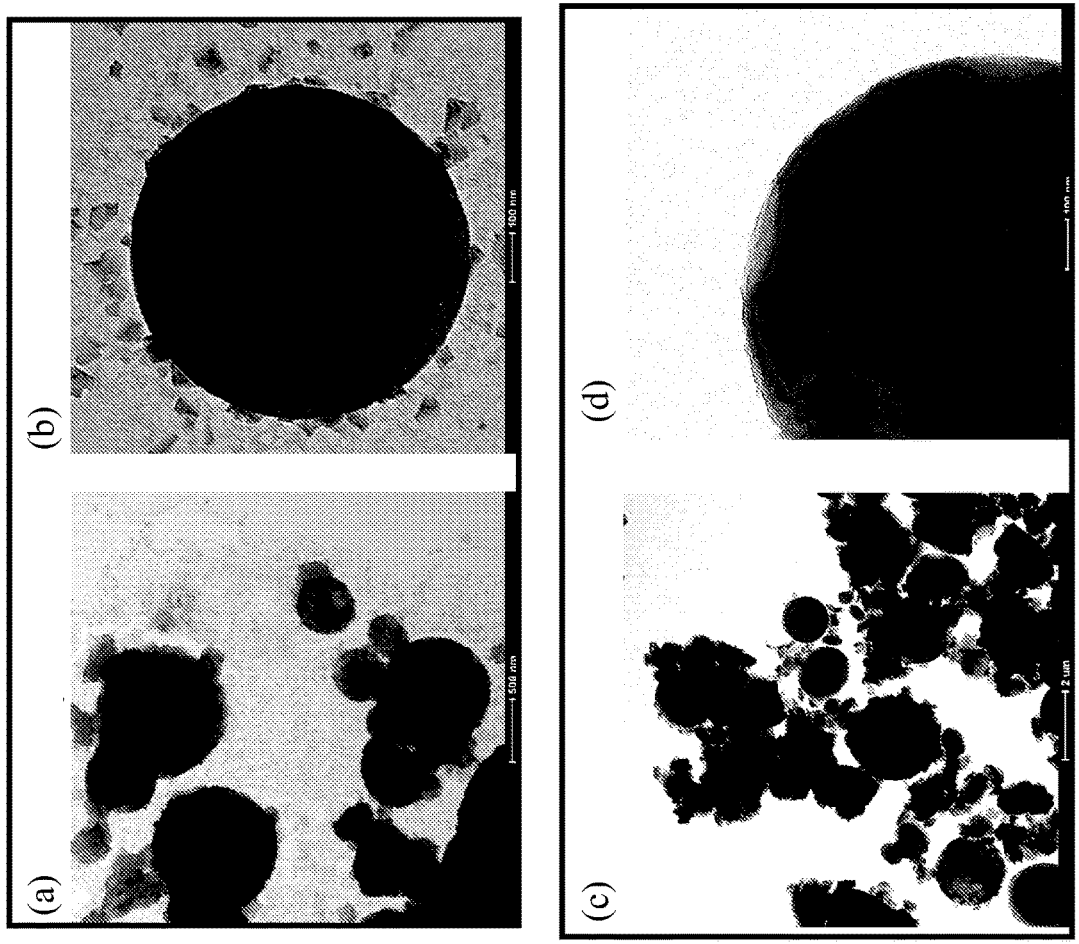
FIG. 49(a)-(d) shows TEM images of particles with a precursor of 1 ml TEOS and 1 g sucrose.

FIG. 49(a-d) shows TEM images of particles with a precursor of 1 ml TEOS and 1 g sucrose. FIGS. 49(a) and (b) are images of aerosolized particles. FIGS. 49(c) and (d) are images of calcined particles.

Figure 51:
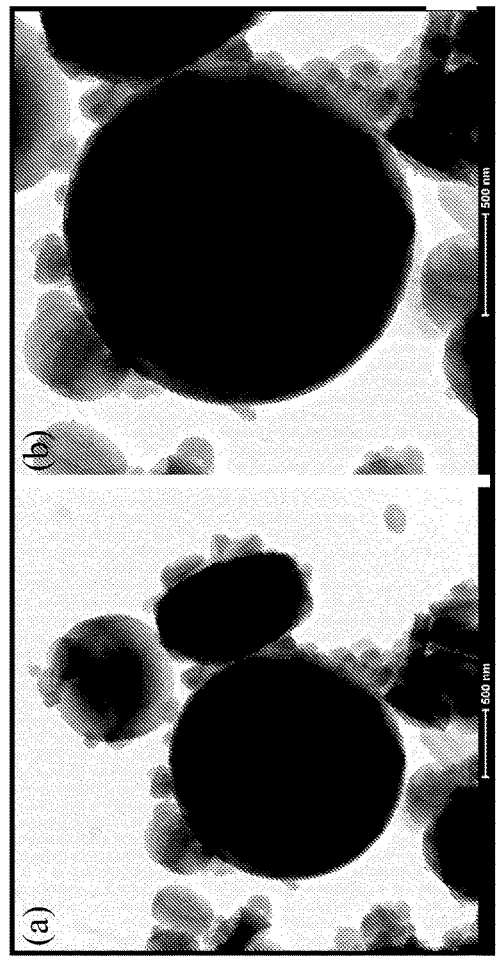
FIG. 51(a)-(b) shows TEM images of aerosolized particles with a precursor of 0.75 ml TEOS and 1 g sucrose.
Figure 52:
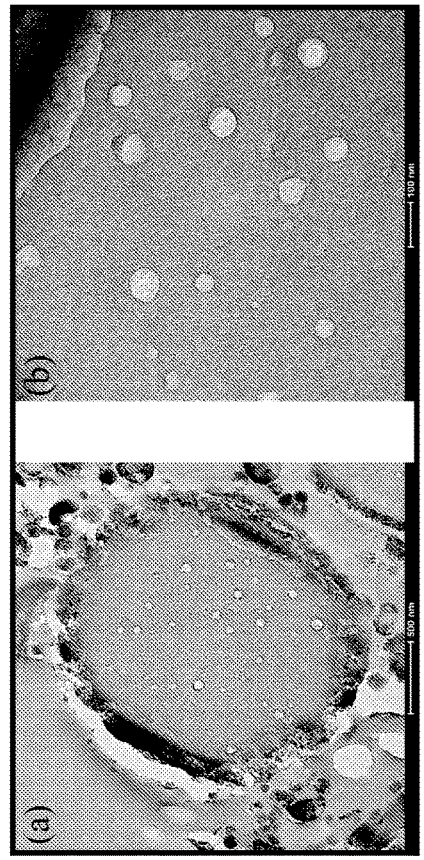
FIG. 52(a)-(b) shows cut section-TEM images of aerosolized particles with a precursor of 0.75 ml TEOS and 1 g sucrose.
Figure 50:
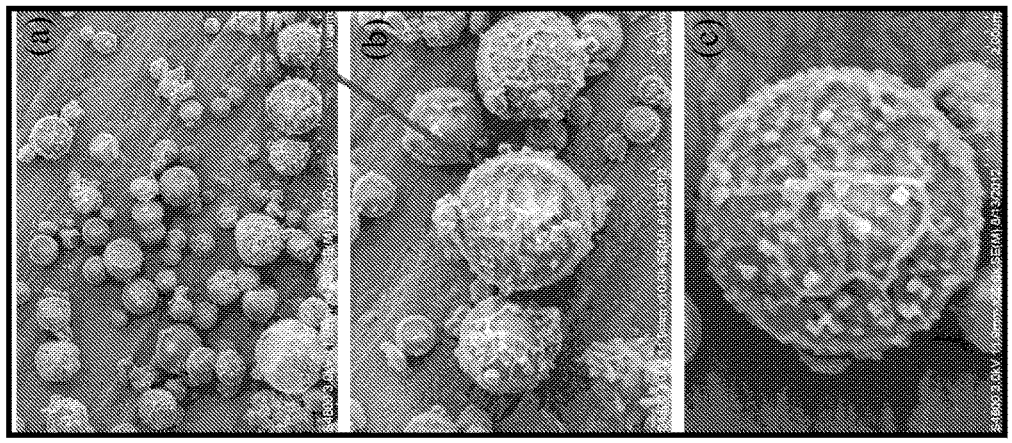
FIG. 50(a)-(c) shows SEM images of aerosolized particles with a precursor of 0.75 ml TEOS and 1 g sucrose.

FIG. 50(a-c) show SEM images of aerosolized particles with a precursor of 0.75 ml TEOS and 1 g sucrose. FIG. 51(a-b) show TEM images of aerosolized particles with a precursor of 0.75 ml TEOS and 1 g sucrose. FIGS. 52(a-b) show cut section-TEM images of aerosolized particles with a precursor of 0.75 ml TEOS and 1 g sucrose.

Figure 54:
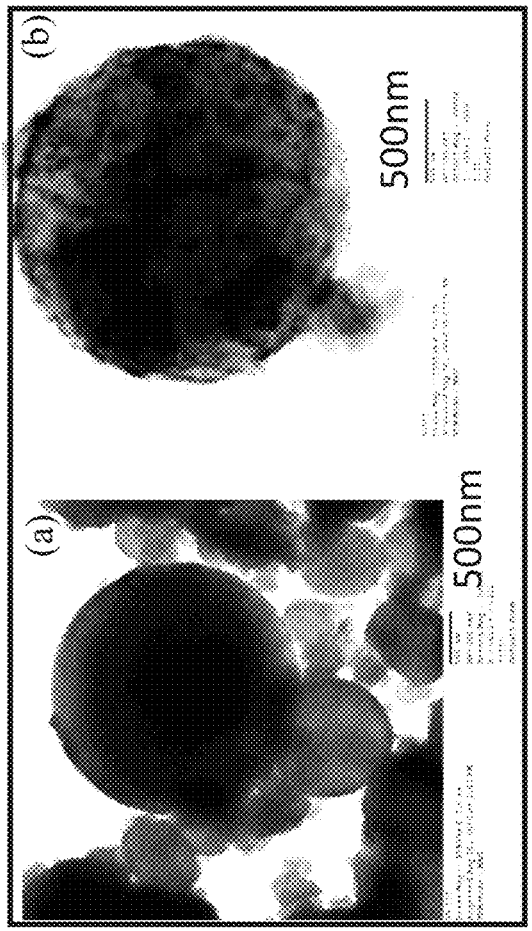
FIG. 54(a)-(b) shows TEM images of calcined particles with a precursor of 0.75 ml TEOS and 1 g sucrose.
Figure 55:
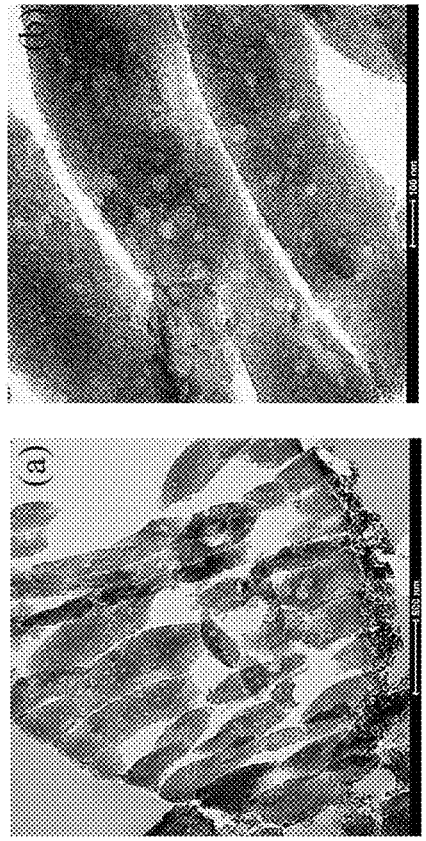
FIGS. 55(a)-(b) shows cut section-TEM images of calcined particles with a precursor of 0.75 ml TEOS and 1 g sucrose.
Figure 53:
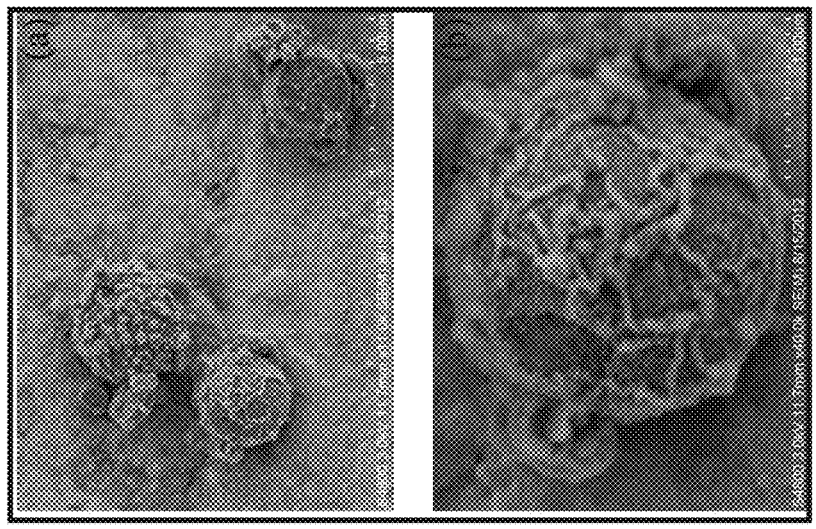
FIG. 53(a)-(b) shows SEM images of calcined particles with a precursor of 0.75 ml TEOS and 1 g sucrose.

FIG. 53(a-b) show SEM images of calcined particles with a precursor of 0.75 ml TEOS and 1 g sucrose. FIG. 54(a-b) show TEM images of calcined particles with a precursor of 0.75 ml TEOS and 1 g sucrose. FIGS. 55(a-b) show cut section-TEM images of calcined particles with a precursor of 0.75 ml TEOS and 1 g sucrose.

| TEOS | Sucrose | Observe |
|---|---|---|
| 1 ml<br>molar ratio = 3:1 | 0.5 g | Hollow thin shells after calcination (10-20 nm). BET surface area is 372 m2/g. |
| 1 ml<br>molar ratio = 2:1 | 0.75 g | After calcination, some (particles with diameter below 300 nm) are hollow and particles with large diameter are dense. There are pores inside the particles. |
| 1 ml<br>molar ratio = 1.5:1 | 1 g | After calcination, some of the particles are hollow but most particles are dense spheres. |
| 0.75 ml<br>molar ratio = 1:1 | 1 g | After synthesis, particles have cage-like structures. Most of the particles are not hollow. After calcination, particles still have cage-like structures. There are many pores on the particles. Most of the particles are not hollow. |

Nanohorns

In some embodiments, the carbon precursor concentration in the precursor solution may be increased, resulting in particles that have long protrusions, leading to a term coined as "nanohorns"

The pressure buildup during pyrolysis, rather than rupturing the shells, leads to yielding and the formation of these long protrusions some of which are longer than the particle diameter. This is an interesting structural feature as it implies that the hydrodynamics of such particles are significantly different from the hydrodynamics of spherical particles. Additionally, the protrusions may have significant consequences in the anchoring of these particles at fluid interfaces and the formation of Pickering emulsions. Such particles may not be able to easily rotate at an interface leading to the possibility of preparing a variety of Janus particles. An interesting aspect of these particles seems to be that they are not hollow internally. In other words, the excess carbon precursor loading leads to a yielding of the silica shell and the inability to firmly compress the carbon onto the silica shell.

In an exemplary synthesis, about 0.8 g-1.9 g, preferably 1.0 g, of $FeCl_3.6H_2O$ is first dissolved in 15 mL of ethanol followed by the addition of about 0.1 g-2.2 g, preferably 1.1 g, of CTAB. To this solution, 1.0 mL-9 mL, preferably 4.2 g, of TEOS, 1.8 mL of 0.1 M HCl and 2.0 g sucrose are added. The resulting solution is aged for 0.5 h under stirring. The precursor is first atomized to form aerosol droplets, which are then sent through a drying zone and heating zone where preliminary solvent evaporation and silica condensation occur. The temperature of the heating zone is held at 400° C. The resulting particles are collected by a filter maintained at 80° C. The as-synthesized particles are pyrolyzed at 500° C. for 3 h to generate nanohorn structure.

Using a Titania Precursor

Figure 25:
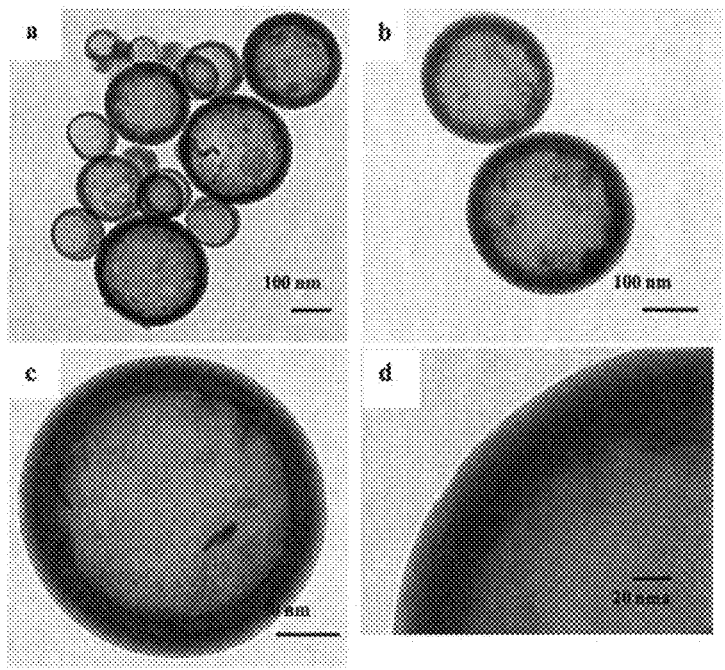
FIG. 25 shows exemplary silica-titanate hollow spheres.
Figure 26:
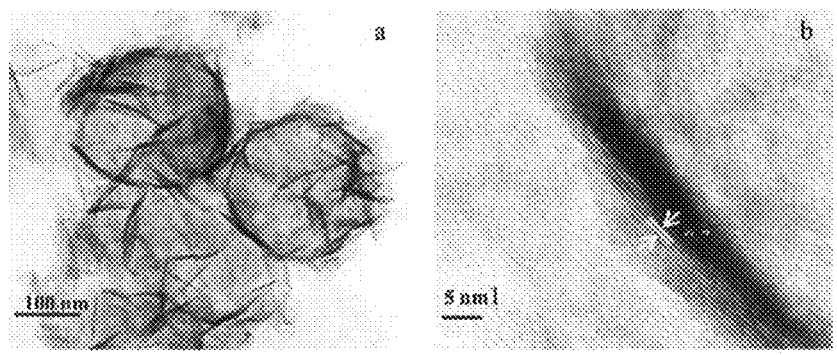
FIG. 26 shows representative TEM images of single titania layer hollow microspheres after etching and calcination treatment: (a) at low magnification; (b) HR TEM of spindle area.
Figure 38:
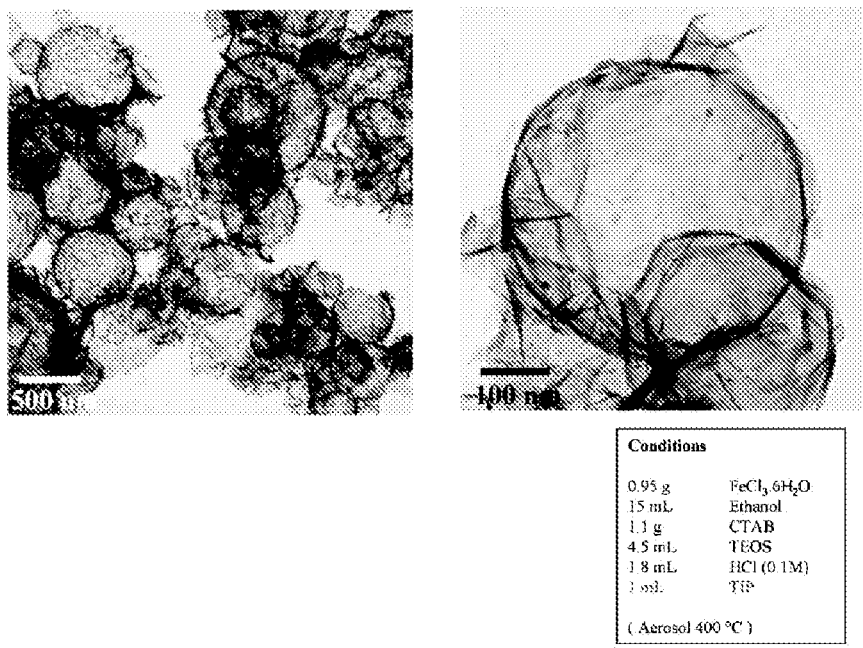
FIG. 38 illustrates wide open highly porous titania.
Figure 39:
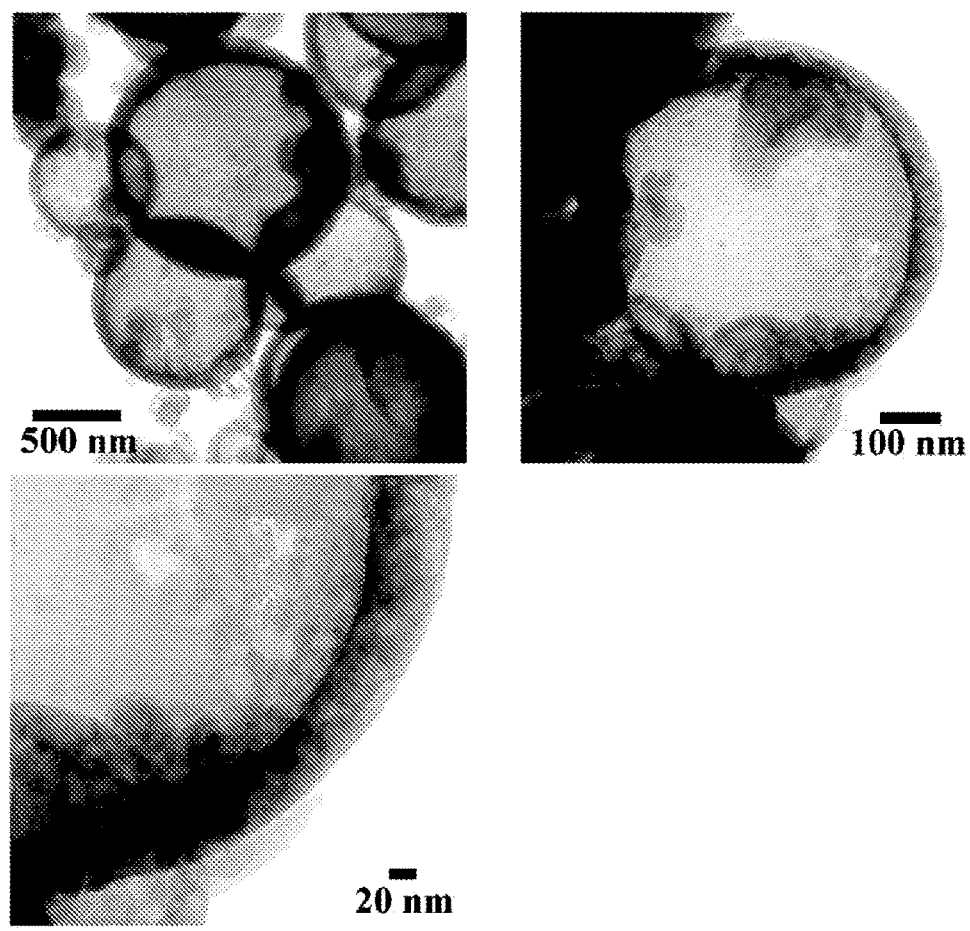
FIG. 39 shows single layer hollow silica particles washed with deionized water, wherein adding salt (NaCl) in the precursor makes the shells porous. Molar ratio of NaCl/$FeCl_3$=1/1.

In some embodiments, materials other than carbon precursors may be used in the precursor solution. In one embodiment, titanium isopropoxide (TIP) rather than sucrose may be introduced to the precursor solution. FIG. 25 illustrates exemplary results. There is evidence of a two layer structure indicating the ability of silica to form a rapid shell. However, there is no clear delineation between the two layers as silica titanate bonds can form (—Si—O—Ti—). In some embodiments, the silica may be etched out (using NaOH to selectively remove silica) leads to the fragile spherical structures of titania shown in FIG. 26. FIG. 38 shows wide open highly porous titania.

Both the double layer silica-titania particles and the etched particles have significant applications in photocatalysis. Light may be able to penetrate easily through the shell allowing efficient photocatalysis to take place. The buoyancy of these hollow particles might make them especially suitable to be used in oil spill mitigation technologies.

Figure 27:
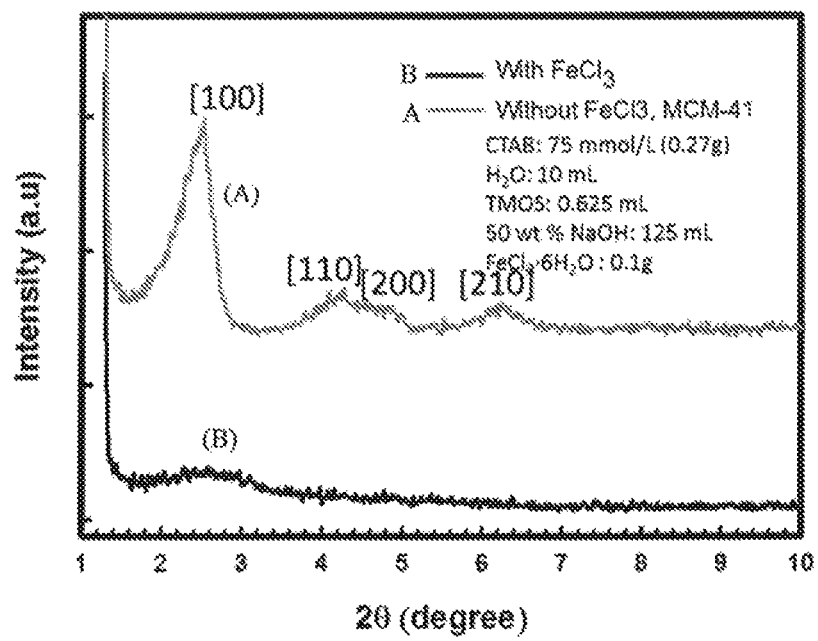
FIG. 27 shows an illustration that the addition of $FeCl_3$ leads to very weakly crystalline silicas and the negation of the templating effect of CTAB.
Figure 28:
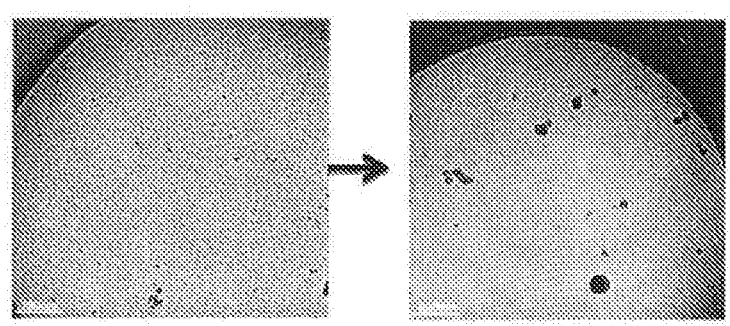
FIG. 28 shows an exemplary illustration of the transition from spherical CTAB micelles to long wormlike micelles upon incorporation of interfacially active phenols.
Figure 29:
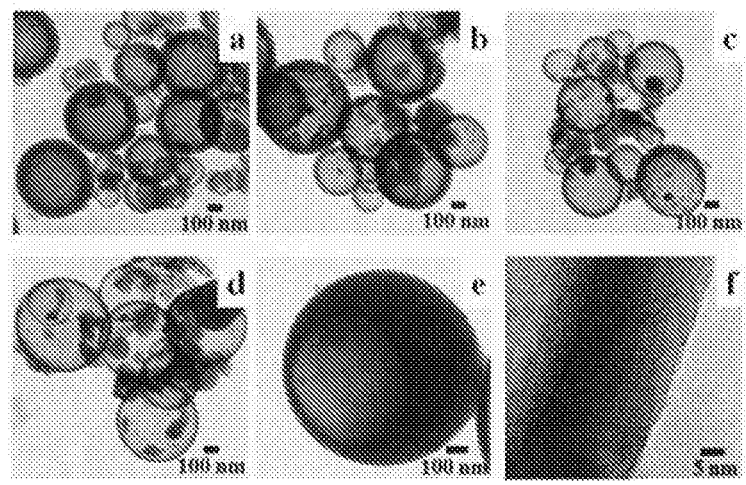
FIG. 29 illustrates representative electron micrographs of calcined hollow silica microspheres: (a) low magnification TEM image at Fe:Si molar ratio of 1:13; (b) low mganification TEM image at Fe:Si molar ratio of 1:8; (c) low magnification TEM image at Fe:Si molar ratio of 1:6; (d) low magnification TEM image at Fe:Si molar ratio of 1:2.7; (e) TEM image of an as-synthesized microsphere at Fe:Si molar ratio of 1:2.7; (f) HRTEM of a calcined microsphere at Fe:Si molar ratio of 1:2.7.
Figure 30:
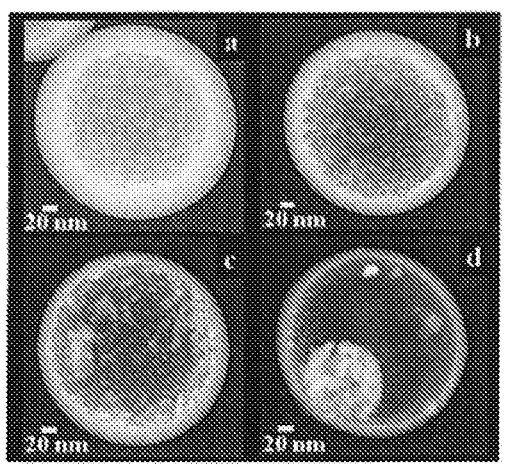
FIG. 30 illustrates representative electron micrographs of calcined hollow silica microspheres: (a) TEM image at Fe:Si molar ratio of 1:13; (b) TEM image at Fe:Si molar ratio of 1:8; (c) TEM image at Fe:Si molar ratio of 1:6; (d) TEM image at Fe:Si molar ratio of 1:2.7.

FIG. 27 illustrates that the addition of $FeCl_3$ destroys the hexagonally ordered structure of MCM-41 (ordered mesoporous silica obtained by templating silicas with CTAB). This is clear indication that the structure modifying effect of Fe (III) may also be present in solution based experiments.

In an exemplary synthesis, an aerosol precursor is prepared by mixing 3.5 mmol $FeCl_3.6H_2O$ and 3.0 mmol CTAB in ethanol (15 mL) first, followed by sonication for 5 min. To this solution, 3.3 mmol TIP, 20.3 mmol TEOS and 1.8 mL of 0.1 M HCl are added. The final precursor solution has a molar ratio of $FeCl_3.6H_2O$:TIP:TEOS:CTAB:HCl:EtOH=1:0.94:5.8:0.86:0.05:74. The solution is then aged for 30 min under magnetic stirring and atomized to form aerosol droplets which were sent through a drying zone and heating zone.

EXAMPLES

Examples and methods of use are described herein as a basis for teaching one skilled in the art to employ the invention in any appropriate manner. These examples disclosed herein are not to be interpreted as limiting.

Example 1: The Development of New Photocatalysts

Some embodiments may utilize thin silica shells with an inner backing primarily of titania indicates for photocatalysts with buoyant properties in solution. This has tremendous applications in cleaning and remediation technologies and in the development of dye sensitized solar cells. The photocatalytic activity of each $TiO_2$ sample will be evaluated by the degradation of Rhodamine B in deionized water. The reaction will be carried out in a RPR-100 Rayonet reactor (1.65×108 photons/s/cm3) using emission at 254 nm. In a typical experiment, 10 mg of TiO2 is added to 50 mL of a 1.0×10−5 mol·L−1 Rhodamine B solution and magnetically stirred in the dark for 30 min prior to irradiation, to achieve adsorption equilibrium of Rhodamine B with the catalyst. The samples are collected every 20 min by centrifugation to determine the degradation rate by UV-vis adsorption (553.5 nm, Shimadzu UV 1700). Comparisons with the standard photocatalyst (Degussa P25) will be made.

Example 2: The Development of New Classes of Colloidosomes

Embodiments can be used to solubilize/emulsify mutually immiscible phases forming emulsions that are stable over extended periods. Such surfactant free emulsions, also known as Pickering emulsions, are characterized by the degree of wettability of the particles by either the dispersed phase or the continuous phase as determined by the contact angle (θ), defined as $$\cos\theta = \frac{\gamma_{so} - \gamma_{sw}}{\gamma_{ow}}$$

where $\gamma_{so}$, $\gamma_{sw}$, and $\gamma_{ow}$ are the interfacial tensions at the solid-oil, solid-water, and oil-water interfaces, respectively. As a general rule of thumb, hydrophobic particles (θ>90°) preferentially disperse in the oil phase and stabilize water-in-oil emulsions, while hydophilic particles wetted by water (θ<90°) solubilize oil-in-water emulsions. The contact angle of colloidal particles at the interface is analogous to the hydrophilic-lipophilic balance of surfactants, and the value of the contact angle typically determines the nature of the emulsion (oil in water or water in oil) in systems that have similar amounts of the two phases. Mechanisms involved in the stabilization of particle based emulsions and phase transitions have been extensively discussed by Binks and coworkers and in recent years, particle stabilized emulsions have been used to develop novel applications ranging from the synthesis of Janus particles and colloidosomes to drug delivery and catalysis at interfaces. The self assembly of micro and nanoparticles at interfaces is also of much interest from the perspective of creating building blocks for hierarchical structures. In understanding the nature of Pickering emulsions and self-assembly at interfaces, model systems typically used are hydrophilic colloidal silicas or hydrophilic latex particles which form oil-in-water emulsions. Water-in-oil Pickering emulsions are usually studied through the use of hydrophobically modified silicas. The rapid development of applications involving carbon based materials has led to interest in the assembly of irregular sized carbon black particles, graphene sheets, and carbon nanotubes at interfaces.

The feasibility of forming water-in-trichloroethylene emulsions using carbon microspheres has been shown. While the work was done in relevance to environmental remediation of TCE., it is straightforward to substitute an oil phase (e.g. octane) instead of TCE. Cryo-SEM of water in TCE Pickering emulsions can illustrate the assembly of particles at the interface.

The approach in the present invention will be to use the bilayer particles to stabilize oil in water emulsions and then connect up the particles through formation of the Si—O—Si bond between particles. In one embodiment, the present invention can create novel colloidosomes of bilayer particles. It is also possible to individually use the silica shells to stabilize oil in water emulsions and the carbon shells to stabilize water in oil emulsions. One embodiment may comprise combination of the two systems to lead to the formation of bicontinuous emulsions stabilized by particles.

Acronymns
BET Brunauer-Emmet-Teller
BJH Barret-Joyner-Halenda
CTAA cetyltrimethyl ammonium astatide
CTAB cetyl trimethylammonium bromide
CTAF cetyltrimethyl ammonium fluoride
CTAI cetyltrimethyl ammonium iodide
DI deionized
EDS energy dispersive spectroscopy
Hc coercivity
HF Hydrogen fluoride
HRTEM High-resolution transmission electron microscopy
MCM-41 Mobil Composition of Matter No. 41
Mr magnetization
SEM scanning electron microscopy transmission electron microscopy
SQUID superconducting quantum interference device
TEM transmission electron microscopy
TEOS tetraethyl orthosilicate
TIP titanium isopropoxide
UV ultraviolet
XRD X-ray diffraction

REFERENCES

Fujiwara, M.; Shiokawa, K.; Hayashi, K.; Morigaki, K.; Nakahara, Y. Journal of Biomedical Materials Research Part A 2007, 81A, 103-112.

Liang, H.-P.; Zhang, H.-M.; Hu, J.-S.; Guo, Y.-G.; Wan, L.-J.; Bai, C.-L. Angewandte Chemie International Edition 2004, 43, 1540-1543.

Kim, S.-W.; Kim, M.; Lee, W. Y; Hyeon, T. Journal of the American Chemical Society 2002, 124, 7642-7643.

Seo, J. S.; Whang, D.; Lee, H.; Jun, S. I.; Oh, J.; Jeon, Y. J.; Kim, K. Nature 2000, 404, 982-986.

Chen, H.; He, J.; Tang, H.; Yan, C. Chemistry of Materials 2008, 20, 5894-5900.

Yang, J.; Lee, J.; Kang, J.; Lee, K.; Suh, J.-S.; Yoon, H.-G.; Huh, Y.-M.; Haam, S. Langmuir 2008, 24, 3417-3421.

Li, Y. Y; Cunin, F.; Link, J. R.; Gao, T.; Betts, R. E.; Reiver, S. H.; Chin, V.; Bhatia, S. N.; Sailor, M. J. Science 2003, 299, 2045-2047.

Li, X.-L.; Lou, T.-J.; Sun, X.-M.; Li, Y.-D. Inorganic Chemistry 2004, 43, 5442-5449.

Lou, X. W.; Archer, L. A.; Yang, Z. Advanced Materials 2008, 20, 3987-4019.

Tissot, I.; Reymond, J. P.; Lefebvre, F.; Bourgeat-Lami, E. Chemistry of Materials 2002, 14, 1325-1331.

Jin, X.; Cao, S.; Yuan, X.; Wu, W.; Hu, J.; Sheng, W. Australian Journal of Chemistry, 63, 1418-1422.

Ge, C.; Zhang, D.; Wang, A.; Yin, H.; Ren, M.; Liu, Y; Jiang, T.; Yu, L. Journal of Physics and Chemistry of Solids 2009, 70, 1432-1437.

Zhao, W.; Lang, M.; Li, Y.; Li, L.; Shi, J. Journal of Materials Chemistry 2009, 19, 2778-2783.

Yoon, S. B.; Kim, J. Y; Kim, J. H.; Park, S. G.; Kim, J. Y; Lee, C. W.; Yu, J. S. Current Applied Physics 2006, 6, 1059-1063.

Cornelissen, J. J. L. M.; Connor, E. F.; Kim, H.-C.; Lee, V. Y.; Magibitang, T.; Rice, P. M.; Volksen, W.; Sundberg, L. K.; Miller, R. D. Chemical Communications 2003, 1010-1011.

Kim, S. S.; Zhang, W.; Pinnavaia, T. J. Science 1998, 282, 1302-1305.

Zoldesi, C. I.; van Walree, C. A.; Imhof, A. Langmuir 2006, 22, 4343-4352.

Graf, C.; van Blaaderen, A. Langmuir 2001, 18, 524-534.

Zha, L. S.; Zhang, Y.; Yang, W. L.; Fu, S. K. Advanced Materials 2002, 14, 1090-1092.

Mandal, T. K.; Fleming, M. S.; Walt, D. R. Chemistry of Materials 2000, 12, 3481-3487.

Xu, X.; Asher, S. A. Journal of the American Chemical Society 2004, 126, 7940-7945.

Park, J.-H.; Oh, C.; Shin, S.-I.; Moon, S.-K.; Oh, S.-G. Journal of Colloid and Interface Science 2003, 266, 107-114.

Hentze, H.-P.; Raghavan, S. R.; McKelvey, C. A.; Kaler, E. W. Langmuir 2003, 19, 1069-1074.

Zoldesi, C. I.; Imhof, A. Advanced Materials 2005, 17, 924-928.

Yuan, J.; Bai, X.; Zhao, M.; Zheng, L. Langmuir, 26, 11726-11731.

Wu, X.; Tian, Y.; Cui, Y.; Wei, L.; Wang, Q.; Chen, Y. The Journal of Physical Chemistry C 2007, 111, 9704-9708.

Lou, X. W.; Yuan, C.; Rhoades, E.; Zhang, Q.; Archer, L. A. Advanced Functional Materials 2006, 16, 1679-1684.

Yin, Y; Rioux, R. M.; Erdonmez, C. K.; Hughes, S.; Somorjai, G. A.; Alivisatos, A. P. Science 2004, 304, 711-714.

Zheng, T.; Pang, J.; Tan, G.; He, J.; McPherson, G. L.; Lu, Y; John, V. T.; Zhan, J. Langmuir 2007, 23, 5143-5147.

Brunauer, S.; Deming, L. S.; Deming, W. E.; Teller, E. Journal of the American Chemical Society 1940, 62, 1723-1732.

Beck, J. S.; Vartuli, J. C.; Roth, W. J.; Leonowicz, M. E.; Kresge, C. T.; Schmitt, K. D.; Chu, C. T. W.; Olson, D. H.; Sheppard, E. W.; McCullen, S. B.; Higgins, J. B.; Schlenker, J. L., A NEW FAMILY OF MESOPOROUS MOLECULAR-SIEVES PREPARED WITH LIQUID-CRYSTAL TEMPLATES. Journal of the American Chemical Society 1992, 114, (27), 10834-10843.

Kresge, C. T.; Leonowicz, M. E.; Roth, W. J.; Vartuli, J. C.; Beck, J. S., ORDERED MESOPOROUS MOLECULAR-SIEVES SYNTHESIZED BY A LIQUID-CRYSTAL TEMPLATE MECHANISM. Nature 1992, 359, (6397), 710-712.

Lu, Y.; Fan, H.; Stump, A.; Ward, T. L.; Rieker, T.; Brinker, C. J., Aerosol-assisted self-assembly of mesostructured spherical nanoparticles. Nature 1999, 398, (6724), 223-226.

Lu, Y. F.; Fan, H. Y.; Stump, A.; Ward, T. L.; Rieker, T.; Brinker, C. J., Aerosol-assisted self-assembly of mesostructured spherical nanoparticles. Nature 1999, 398, (6724), 223-226.

Boissiere, C.; Grosso, D.; Chaumonnot, A.; Nicole, L.; Sanchez, C., Aerosol Route to Functional Nanostructured Inorganic and Hybrid Porous Materials. Advanced Materials 2011, 23, (5), 599-623.

Zheng, T.; Pang, J.; Tan, G.; He, J.; McPherson, G. L.; Lu, Y.; John, V. T.; Zhan, J., Surfactant Templating Effects on the Encapsulation of Iron Oxide Nanoparticles within Silica Microspheres. Langmuir 2007, 23, (9), 5143-5147.

Fujiwara, M.; Shiokawa, K.; Hayashi, K.; Morigaki, K.; Nakahara, Y., Direct encapsulation of BSA and DNA into silica microcapsules (hollow spheres). J. Biomed. Mater. Res. A 2007, 81A, (1), 103-112.

Kim, S.-W.; Kim, M.; Lee, W. Y.; Hyeon, T., Fabrication of Hollow Palladium Spheres and Their Successful Application to the Recyclable Heterogeneous Catalyst for Suzuki Coupling Reactions. J. Am. Chem. Soc. 2002, 124, (26), 7642-7643.

Liang, H.-P.; Zhang, H.-M.; Hu, J.-S.; Guo, Y.-G.; Wan, L.-J.; Bai, C.-L., Pt Hollow Nanospheres: Facile Synthesis and Enhanced Electrocatalysts. Angew. Chem. Int. Ed. 2004, 43, (12), 1540-1543.

Seo, J. S.; Whang, D.; Lee, H.; Jun, S. I.; Oh, J.; Jeon, Y. J.; Kim, K., A homochiral metal-organic porous material for enantioselective separation and catalysis. Nature 2000, 404, (6781), 982-986.

Li, Y. Y.; Cunin, F.; Link, J. R.; Gao, T.; Betts, R. E.; Reiver, S. H.; Chin, V.; Bhatia, S. N.; Sailor, M. J., Polymer Replicas of Photonic Porous Silicon for Sensing and Drug Delivery Applications. Science 2003, 299, (5615), 2045-2047.

Chen, H.; He, J.; Tang, H.; Yan, C., Porous Silica Nanocapsules and Nanospheres: Dynamic Self-Assembly Synthesis and Application in Controlled Release. Chem. Mater. 2008, 20, (18), 5894-5900.

Yang, J.; Lee, J.; Kang, J.; Lee, K.; Suh, J.-S.; Yoon, H.-G.; Huh, Y.-M.; Haam, S., Hollow Silica Nanocontainers as Drug Delivery Vehicles. Langmuir 2008, 24, (7), 3417-3421.

Li, X.-L.; Lou, T.-J.; Sun, X.-M.; Li, Y.-D., Highly Sensitive WO3 Hollow-Sphere Gas Sensors. Inorg. Chem. 2004, 43, (17), 5442-5449.

Tissot, I.; Reymond, J. P.; Lefebvre, F.; Bourgeat-Lami, E., SiOH-Functionalized Polystyrene Latexes. A Step toward the Synthesis of Hollow Silica Nanoparticles. Chem. Mater. 2002, 14, (3), 1325-1331.

Cornelissen, J. J. L. M.; Connor, E. F.; Kim, H.-C.; Lee, V. Y.; Magibitang, T.; Rice, P. M.; Volksen, W.; Sundberg, L. K.; Miller, R. D., Versatile synthesis of nanometer sized hollow silica spheres. Chem. Commun. 2003, (8), 1010-1011.

Park, J.-H.; Oh, C.; Shin, S.-I.; Moon, S.-K.; Oh, S.-G., Preparation of hollow silica microspheres in W/O emulsions with polymers. J. Colloid Interface Sci. 2003, 266, (1), 107-114.

Xu, X.; Asher, S. A., Synthesis and Utilization of Monodisperse Hollow Polymeric Particles in Photonic Crystals. Journal of the American Chemical Society 2004, 126, (25), 7940-7945.

Zoldesi, C. I.; Imhof, A., Synthesis of Monodisperse Colloidal Spheres, Capsules, and Microballoons by Emulsion Templating. Adv. Mater. 2005, 17, (7), 924-928.

Lou, X. W.; Yuan, C.; Rhoades, E.; Zhang, Q.; Archer, L. A., Encapsulation and Ostwald Ripening of Au and Au—Cl Complex Nanostructures in Silica Shells. Advanced Functional Materials 2006, 16, (13), 1679-1684.

Yoon, S. B.; Kim, J. Y; Kim, J. H.; Park, S. G.; Kim, J. Y.; Lee, C. W.; Yu, J. S., Template synthesis of nanostructured silica with hollow core and mesoporous shell structures. Curt Appl. Phys. 2006, 6, (6), 1059-1063.

Zoldesi, C. I.; van Walree, C. A.; Imhof, A., Deformable Hollow Hybrid Silica/Siloxane Colloids by Emulsion Templating. Langmuir 2006, 22, (9), 4343-4352.

Lou, X. W.; Yuan, C.; Archer, L. A., Shell-by-Shell Synthesis of Tin Oxide Hollow Colloids with Nanoarchitectured Walls: Cavity Size Tuning and Functionalization. Small 2007, 3, (2), 261-265.

Suarez, F. J.; Sevilla, M.; Alvarez, S.; Valdes-Solis, T.; Fuertes, A. B., Synthesis of Highly Uniform Mesoporous Sub-Micrometric Capsules of Silicon Oxycarbide and Silica. Chemistry of Materials 2007, 19, (13), 3096-3098.

Wu, X.; Tian, Y.; Cui, Y.; Wei, L.; Wang, Q.; Chen, Y, Raspberry-like Silica Hollow Spheres:??Hierarchical Structures by Dual Latex?*urfactant Templating Route. J. Phys. Chem. C 2007, 111, (27), 9704-9708.

Lou, X. W.; Archer, L. A.; Yang, Z., Hollow Micro-/Nanostructures: Synthesis and Applications. Adv. Mater. 2008, 20, (21), 3987-4019.

Ge, C.; Zhang, D.; Wang, A.; Yin, H.; Ren, M.; Liu, Y.; Jiang, T.; Yu, L., Synthesis of porous hollow silica spheres using polystyrene-methyl acrylic acid latex template at different temperatures. J. Phys. Chem. Solids 2009, 70, (11), 1432-1437.

Liu, J.; Deng, Y.; Liu, C.; Sun, Z.; Zhao, D., A simple approach to the synthesis of hollow microspheres with magnetite/silica hybrid walls. Journal of Colloid and Interface Science 2009, 333, (1), 329-334.

Zhao, W.; Lang, M.; Li, Y.; Li, L.; Shi, J., Fabrication of uniform hollow mesoporous silica spheres and ellipsoids of tunable size through a facile hard-templating route. J. Mater. Chem. 2009, 19, (18), 2778-2783.

Zhao, Y.; Jiang, L., Hollow Micro/Nanomaterials with Multilevel Interior Structures. Advanced Materials 2009, 21, (36), 3621-3638.

Jin, X.; Cao, S.; Yuan, X.; Wu, W.; Hu, J.; Sheng, W., The Preparation of Monodisperse Cationic Polystyrene and its Application to the Synthesis of Hollow Silica Spheres. Aust. J. Chem. 2010, 63, (10), 1418-1422.

Hosseini, S. H.; Rahimi, R.; Kerdari, H., Preparation of a nanocomposite of magnetic, conducting nanoporous polyaniline and hollow manganese ferrite. Polym J 2011, 43, (9), 745-750.

Wu, S.-H.; Tseng, C.-T.; Lin, Y.-S.; Lin, C.-H.; Hung, Y.; Mou, C.-Y., Catalytic nano-rattle of Au@hollow silica: towards a poison-resistant nanocatalyst. J. Mater. Chem. 2011, 21, (3), 789-794.

Lee, H. J.; Cho, W.; Oh, M., Advanced fabrication of metal-organic frameworks: template-directed formation of polystyrene@ZIF-8 core-shell and hollow ZIF-8 microspheres. Chemical Communications 2012, 48, (2), 221.

Sunkara, B.; Zhan, J. J.; Kolesnichenko, I.; Wang, Y. Q.; He, J. B.; Holland, J. E.; McPherson, G. L.; John, V. T., Modifying Metal Nanoparticle Placement on Carbon Supports Using an Aerosol-Based Process, with Application to the Environmental Remediation of Chlorinated Hydrocarbons. Langmuir 2011, 27, (12), 7854-7859.

Zhan, J. J.; Kolesnichenko, I.; Sunkara, B.; He, J. B.; McPherson, G. L.; Piringer, G.; John, V. T., Multifunctional Iron-Carbon Nanocomposites through an Aerosol-Based Process for the In Situ Remediation of Chlorinated Hydrocarbons. Environmental Science & Technology 2011, 45, (5), 1949-1954.

Zhane, J. J.; Sunkara, B.; Tang, J. J.; Wang, Y. Q.; He, J. B.; McPherson, G. L.; John, V. T., Carbothermal Synthesis of Aerosol-Based Adsorptive-Reactive Iron-Carbon Particles for the Remediation of Chlorinated Hydrocarbons. Industrial & Engineering Chemistry Research 2011, 50, (23), 13021-13029.

Agarwal, V.; Singh, M.; McPherson, G.; John, V.; Bose, A., Microstructure evolution in aqueous solutions of cetyl trimethylammonium bromide (CTAB) and phenol derivatives. Colloids and Surfaces a-Physicochemical and Engineering Aspects 2006, 281, (1-3), 246-253.

Tan, G.; Ford, C.; John, V. T.; He, J.; McPherson, G. L.; Bose, A., Surfactant solubilization and the direct encapsulation of interfacially active Phenols in mesoporous silicas. Langmuir 2008, 24, (3), 1031-1036.

Glatter, O.; Hofer, M., ELASTIC LIGHT-SCATTERING FROM NONSPHERICAL AND POLYDISPERSE PARTICLES IN THE SIZE RANGE FROM 100 TO 2000 NM. Makromolekulare Chemie-Macromolecular Symposia 1988, 15, 191-200.

Glatter, O.; Hofer, M., INTERPRETATION OF ELASTIC LIGHT-SCATTERING DATA .3. DETERMINATION OF SIZE DISTRIBUTIONS OF POLYDISPERSE SYSTEMS. Journal of Colloid and Interface Science 1988, 122, (2), 496-506.

Glatter, O.; Hofer, M., INTERPRETATION OF ELASTIC LIGHT-SCATTERING DATA IN REAL SPACE .2. NONSPHERICAL AND INHOMOGENEOUS MONODISPERSE SYSTEMS. Journal of Colloid and Interface Science 1988, 122, (2), 484-495.

Glatter, O., COMPARISON OF 2 DIFFERENT METHODS FOR DIRECT STRUCTURE-ANALYSIS FROM SMALL-ANGLE SCATTERING DATA. Journal of Applied Crystallography 1988, 21, 886-890.

Glatter, O., DETERMINATION OF PARTICLE-SIZE DISTRIBUTION-FUNCTIONS FROM SMALL-ANGLE SCATTERING DATA BY MEANS OF THE INDIRECT TRANSFORMATION METHOD. Journal of Applied Crystallography 1980, 13, Feb. 7-11.

Glatter, O., EVALUATION OF SMALL-ANGLE SCATTERING DATA FROM LAMELLAR AND CYLINDRICAL PARTICLES BY THE INDIRECT TRANSFORMATION METHOD. Journal of Applied Crystallography 1980, 13, Dec. 577-584.

Fritz, G.; Bergmann, A.; Glatter, O., Evaluation of small-angle scattering data of charged particles using the generalized indirect Fourier transformation technique. Journal of Chemical Physics 2000, 113, (21), 9733-9740.

Fritz, G.; Glatter, O., Structure and interaction in dense colloidal systems: evaluation of scattering data by the generalized indirect Fourier transformation method. Journal of Physics-Condensed Matter 2006, 18, (36), S2403-S2419.

Singh, M.; Ford, C.; Agarwal, V.; Fritz, G.; Bose, A.; John, V. T.; McPherson, G. L., Structural evolution in cationic micelles upon incorporation of a polar organic dopant. Langmuir 2004, 20, (23), 9931-9937.

Guo, D. J.; You, J. M., Highly catalytic activity of Pt electrocatalyst supported on sulphated $SnO(2)$/multi-walled carbon nanotube composites for methanol electrooxidation. Journal of Power Sources 2012, 198, 127-131.

Hsu, C. H.; Kuo, P. L., The use of carbon nanotubes coated with a porous nitrogen-doped carbon layer with embedded Pt for the methanol oxidation reaction. Journal of Power Sources 2012, 198, 83-89.

Yin, S. B.; Luo, L.; Xu, C.; Zhao, Y. L.; Qiang, Y. H.; Mu, S. C., Functionalizing carbon nanotubes for effective electrocatalysts supports by an intermittent microwave heating method. Journal of Power Sources 2012, 198, 1-6.

Jiang, Y.; Zhang, J.; Qin, Y. H.; Niu, D. F.; Zhang, X. S.; Niu, L.; Zhou, X. G.; Lu, T. H.; Yuan, W. K., Ultrasonic synthesis of nitrogen-doped carbon nanofibers as platinum catalyst support for oxygen reduction. Journal of Power Sources 2011, 196, (22), 9356-9360.

Metz, K. M.; Colavita, P. E.; Tse, K. Y.; Hamers, R. J., Nanotextured gold coatings on carbon nanofiber scaffolds as ultrahigh surface-area electrodes. Journal of Power Sources 2012, 198, 393-401.

Uhm, S.; Jeong, B.; Lee, J., A facile route for preparation of non-noble CNF cathode catalysts in alkaline ethanol fuel cells. Electrochimica Acta 2011, 56, (25), 9186-9190.

Zhang, Y.; Yarin, A. L., Carbon Nanofibers Decorated with Poly(furfuryl alcohol)-Derived Carbon Nanoparticles and Tetraethylorthosilicate-Derived Silica Nanoparticles. Langmuir 2011, 27, (23), 14627-14631.

Choi, J. Y.; Higgins, D.; Chen, Z. W., Highly Durable Graphene Nanosheet Supported Iron Catalyst for Oxygen Reduction Reaction in PEM Fuel Cells. Journal of the Electrochemical Society 2012, 159, (1), B87-B90.

He, W.; Jiang, H. J.; Zhou, Y.; Yang, S. D.; Xue, X. Z.; Zou, Z. Q.; Zhang, X. G.; Akins, D. L.; Yang, H., An efficient reduction route for the production of Pd—Pt nanoparticles anchored on graphene nanosheets for use as durable oxygen reduction electrocatalysts. Carbon 2012, 50, (1), 265-274.

Ma, Y. W.; Sun, L. Y.; Huang, W.; Zhang, L. R.; Zhao, J.; Fan, Q. L., Three-Dimensional Nitrogen-Doped Carbon Nanotubes/Graphene Structure Used as a Metal-Free Electrocatalyst for the Oxygen Reduction Reaction. Journal of Physical Chemistry C 2011, 115, (50), 24592-24597.

Nie, R. F.; Wang, J. H.; Wang, L. N.; Qin, Y.; Chen, P.; Hou, Z. Y., Platinum supported on reduced graphene oxide as a catalyst for hydrogenation of nitroarenes. Carbon 2012, 50, (2), 586-596.

Wietecha, M. S.; Zhu, J.; Gao, G. H.; Wang, N.; Feng, H.; Gorring, M. L.; Kasner, M. L.; Hou, S. E., Platinum nanoparticles anchored on chelating group-modified graphene for methanol oxidation. Journal of Power Sources 2012, 198, 30-35.

Zhang, Y. Z.; Mo, G. Q.; Li, X. W.; Ye, J. S., Iron tetrasulfophthalocyanine functionalized graphene as a platinum-free cathodic catalyst for efficient oxygen reduction in microbial fuel cells. Journal of Power Sources 2012, 197, 93-96.

Wang, S. T.; Zhang, X.; Zhou, G.; Wang, Z. S., Double-layer coating of SrCO(3)/TiO(2) on nanoporous TiO(2) for efficient dye-sensitized solar cells. Physical Chemistry Chemical Physics 2012, 14, (2), 816-822.

Tacchini, I.; Anson-Casaos, A.; Yu, Y. H.; Martinez, M. T.; Lira-Cantu, M., Hydrothermal synthesis of 1D TiO(2) nanostructures for dye sensitized solar cells. Materials Science and Engineering B-Advanced Functional Solid-State Materials 2012, 177, (1), 19-26.

Katoch, A.; Kim, H.; Hwang, T.; Kim, S. S., Preparation of highly stable TiO(2) sols and nanocrystalline TiO(2) films via a low temperature sol-gel route. Journal of Sol-Gel Science and Technology 2012, 61, (1), 77-82.

Binks, B. P.; Horozov, T. S., Colloidal Particles at Liquid Interfaces. Cambridge University Press: 2006.

Binks, B. P., Particles as surfactants-similarities and differences. Current Opinion in Colloid & Interface Science 2002, 7, (1-2), 21-41.

Binks, B. P.; Lumsdon, S. O., Influence of Particle Wettability on the Type and Stability of Surfactant-Free Emulsions. Langmuir 2000, 16, (23), 8622-8631.

Binks, B. P.; Lumsdon, S. O., Catastrophic Phase Inversion of Water-in-Oil Emulsions Stabilized by Hydrophobic Silica. Langmuir 2000, 16, (6), 2539-2547.

Suzuki, D.; Tsuji, S.; Kawaguchi, H., Janus Microgels Prepared by Surfactant-Free Pickering Emulsion-Based Modification and Their Self-Assembly. Journal of the American Chemical Society 2007, 129, (26), 8088-8089.

Dinsmore, A. D.; Hsu, M. F.; Nikolaides, M. G.; Marquez, M.; Bausch, A. R.; Weitz, D. A., Colloidosomes: Selectively Permeable Capsules Composed of Colloidal Particles. Science 2002, 298, (5595), 1006-1009.

Frelichowska, J.; Bolzinger, M.-A.; Pelletier, J.; Valour, J.-P.; Chevalier, Y., Topical delivery of lipophilic drugs from o/w Pickering emulsions. International Journal of Pharmaceutics 2009, 371, (1-2), 56-63.

Crossley, S.; Faria, J.; Shen, M.; Resasco, D. E., Solid Nanoparticles that Catalyze Biofuel Upgrade Reactions at the Water/Oil Interface. Science 2010, 327, (5961), 68-72.

Dai, L. L.; Sharma, R.; Wu, C.-y., Self-Assembled Structure of Nanoparticles at a Liquid-Liquid Interface. Langmuir 2005, 21, (7), 2641-2643.

Frelichowska, J.; Bolzinger, M.-A.; Chevalier, Y., Pickering emulsions with bare silica. Colloids and Surfaces A: Physicochemical and Engineering Aspects 2009, 343, (1-3), 70-74.

P. Binks, B.; O. Lumsdon, S., Stability of oil-in-water emulsions stabilised by silica particles. Physical Chemistry Chemical Physics 1999, 1, (12), 3007-3016.

Vignati, E.; Piazza, R.; Lockhart, T. P., Pickering Emulsions: Interfacial Tension, Colloidal Layer Morphology, and Trapped-Particle Motion. Langmuir 2003, 19, (17), 6650-6656.

Binks, B. P.; Whitby, C. P., Silica Particle-Stabilized Emulsions of Silicone Oil and Water: Aspects of Emulsification. Langmuir 2004, 20, (4), 1130-1137.

Drelich, A.; Gomez, F.; Clausse, D.; Pezron, I., Evolution of water-in-oil emulsions stabilized with solid particles: Influence of added emulsifier. Colloids and Surfaces A: Physicochemical and Engineering Aspects 2010, 365, (1-3), 171-177.

Horikoshi, S.; Akao, Y.; Ogura, T.; Sakai, H.; Abe, M.; Serpone, N., On the stability of surfactant-free water-in-oil emulsions and synthesis of hollow SiO2 nanospheres. Colloids and Surfaces A: Physicochemical and Engineering Aspects 2010, 372, (1-3), 55-60.

Binks, B. P.; Murakami, R., Phase inversion of particle-stabilized materials from foams to dry water. Nature materials 2006, 5, (11), 865-869.

Binks, B. P.; Rodrigues, J. A., Types of Phase Inversion of Silica Particle Stabilized Emulsions Containing Triglyceride Oil. Langmuir 2003, 19, (12), 4905-4912.

Binks, B. P.; Cui, Z. G.; Fletcher, P. D. I., Optical Microscope Absorbance Imaging of Carbon Black Nanoparticle Films at Solid and Liquid Surfaces. Langmuir 2006, 22, (4), 1664-1670.

Guo, P.; Song, H.; Chen, X., Hollow graphene oxide spheres self-assembled by W/O emulsion. Journal of Materials Chemistry 2010, 20, (23), 4867-4874.

Shen, M.; Resasco, D. E., Emulsions Stabilized by Carbon Nanotube-Silica Nanohybrids. Langmuir 2009, 25, (18), 10843-10851.

Matsui, J.; Yamamoto, K.; Miyashita, T., Assembly of untreated single-walled carbon nanotubes at a liquid-liquid interface. Carbon 2009, 47, (6), 1444-1450.

Wang, H.; Hobbie, E. K., Amphiphobic Carbon Nanotubes as Macroemulsion Surfactants. Langmuir 2003, 19, (8), 3091-3093.

Zhang, Y.; Shen, Y.; Kuehner, D.; Wu, S.; Su, Z.; Ye, S.; Niu, L., Directing single-walled carbon nanotubes to self-assemble at water/oil interfaces and facilitate electron transfer. Chemical Communications 2008, (36), 4273-4275.

Venkataraman, P.; Sunkara, B.; St. Dennis, J. E.; J., H.; John, V. T.; Bose, A., Water-in-Trichloroethylene Emulsions Stabilized by Uniform Carbon Microspheres. Langmuir 2012, 28, (2), 1058-1063.

Fujiwara, M.; Shiokawa, K; Hayashi, K; Morigaki, K; Nakahara, Y. Direct encapsulation of BSA and DNA into silica microcapsules (hollow spheres). J. Biomed. Mater. Res. A 2007, 81, 103-112.

Liang. H.-P.; Zhang H.-M.; Hu, J.-S.; Guo, Y.-G.; Wan, L.-J.; Bai, C.-L. Pt hollow nanospheres: facile synthesis and enhanced electrocatalysts. Angew. Chem., Int. Ed. 2004, 43, 1540-1543.

Seo, J. S.; Whang. D.; Lee, H.; Jun, S. I.; Oh, Jeon, Y. J.; Kim, K. A homochiral metal-organic porous material for enantioselective separation and catalysis. Nature 2000, 404, 982-986.

Chen, H.; He, J.; Tang. H.; Yan, C. Porous silica nanocapsules and nanospheres: dynamic self-assembly synthesis and application ill controlled release. Chem. Mater. 2008, 20, 5894-5900.

Li, Y. Y.; Cunin, F.; Link, J. R. Gao, T.; Betts, R. E.; Reiver, S. H.; Chin, V.; Bhatia, S. N.; Sailor, M. J. Polymer replicas of photonic porous silicon for sensing and drug delivery applications. Science 2003, 299, 2045-2047.

Li, X.-L.; Lou, T.-J.; Sun, X.-M.; Li, Y.-D. Highly sensitive $WO_3$ hollow-sphere gas sensors. Inorg. Chem. 2004, 43, 5442-5449.

Ge, C.; Zhang. D.; Wang. A.; Yin, H.; Ren, M.; Liu, Y; Jiang. T.; Yu, L. Synthesis of porous hollow silica spheres using polystyrenemethyl acrylic acid latex template at different temperatures. J. Phys. Chem. Solids 2009, 70, 1432-1437.

Hosseini, S. H.; Rahimi, R.; Kerdari, H. Preparation of a nanocomposite of magnetic, conducting nanoporous polyaniline and hollow manganese ferrite. Polym. J. 2011, 43, 745-750.

Lee, H. J.; Cho, W.; Oh, M. Advanced fabrication of metal-organic frameworks: template-directed formation of polystyrene@ZIF-8 core-shell and hollow ZIF-8 microspheres. Chem. Commun. 2012, 48, 221.

Liu, J.; Deng. Y.; Liu, C.; Sun, Z.; Zhao, D. A simple approach to the synthesis of hollow microspheres with magnetite/silica hybrid walls. J. Colloid Interface Sci. 2009, 333, 329-334.

Lou, X. W.; Archer, L. A.; Yang. Z. Hollow micro-/nanostructures: synthesis and applications. Adv. Mater. 2008 20, 3987-4019.

Lou, X. W.; Yuan, C.; Rhoades, E.; Zhang, Q.; Archer, L. A. Encapsulation and Ostwald ripening of Au and Au—Cl complex nanostructures in silica shells. Adv. Funct. Mater. 2006, 16, 1679-1684.

Suarez, F. J.; Sevilla, M.; Alvarez, S.; Valdes-Solis, T.; Fuertes, A. B. Synthesis of highly uniform mesoporous sub-micrometric capsules of silicon oxycarbide and silica. Chem. Mater. 2007, 19, 3096-3098.

Wu, S.-H.; Tseng, C.-T.; Lin, Y.-S.; Lin, C.-H.; Hung. Y.; Mou, C.-Y. Catalytic nano-rattle of Au@hollow silica: towards a poison-resistant nanocatalyst. J. Mater. Chem. 2011, 21, 789-794.

Xu, X.; Asher, S. A. Synthesis and utilization of monodisperse hollow polymeric particles in photonic crystals. J. Am. Chem. Soc. 2004, 126, 7940-7945.

Zhao, Y.; Jiang. L. Hollow micro/nanomaterials with multilevel interior structures. Adv. Mater 2009, 21, 3621-3638.

Zoldesi, C. I.; Imhof, A. Synthesis of monodisperse colloidal spheres, capsules, and microballoons by emulsion templating. Adv. Mater. 2005, 17, 924-928.

Ding. S.; Chen, J. S.; Qi, G.; Duan, X.; Wang, Z.; Giannelis, E. P.; Archer, L. A.; Lou, X. W. Formation of $SnO_2$ hollow nanospheres inside mesoporous silica nanoreactors. J. Am. Chem. Soc. 2011, 133, 21-23.

Lou, X. W.; Li, C. M.; Archer, L. A. Designed synthesis of coaxial $SnO_2$@carbon hollow nanospheres for highly reversible lithium storage. Adv. Mater. 2009, 21, 2536-2539.

Boissiere, C.; Grosso, D.; Chaumonnot, A.; Nicole, L.; Sanchez, C. Aerosol route to functional nanostructured inorganic and hybrid porous materials. Adv. Mater. 2011, 23, 599-623.

Lu, Y.; Fan, H.; Stump, A.; Ward, T. L.; Rieker, T.; Brinker, C. J. Aerosol-assisted self-assembly of mesostructured spherical nanoparticles. Nature 1999, 398, 223-226.

Zheng. T.; Pang. J.; Tan, G.; He, J.; McPherson, G. L.; Lu, Y; John, V. T.; Zhan, J. Surfactant templating effects on the encapsulation of iron oxide nanoparticles within silica microspheres. Langmuir 2007, 23, 5143-5147.

Y. Zhao and L. Jiang, Adv. Mater., 2009, 21, 3621-3638.

X. W. Lou, L. A. Archer and Z. Yang, Adv. Mater., 2008, 20, 3987-4019.

M. Fujiwara, K. Shiokawa, K. Hayashi, K. Morigaki and Y. Nakahara, J. Biomed. Mater. Res. A 2007, 81A, 103-112.

S. J. Teng, J. N. Wang and X. X. Wang, J. Mater. Chem., 2011, 21, 5443-5450.

J. S. Seo, D. Whang, H. Lee, S. I. Jun, J. Oh, Y. J. Jeon and K. Kim, Nature, 2000, 404, 982-986.

H.-P. Liang, H.-M. Zhang, J.-S. Hu, Y.-G. Guo, L.-J. Wan and C.-L. Bai, Angew. Chem. Int. Ed., 2004, 43, 1540-1543.

Z. Yang, J. Wei, H. Yang, L. Liu, H. Liang and Y. Yang, Eur. J. Inorg. Chem., 2010, 2010, 3354-3359.

C.-Y. Cao, W. Guo, Z.-M. Cui, W.-G. Song and W. Cai, J. Mater. Chem., 2011, 21, 3204-3209.

Z. Lei, Z. Chen and X. S. Zhao, J. Phys. Chem. C, 2010, 114, 19867-19874.

X.-L. Li, T.-J. Lou, X.-M. Sun and Y.-D. Li, Inorg. Chem., 2004, 43, 5442-5449.

X. Lai, J. Li, B. A. Korgel, Z. Dong, Z. Li, F. Su, J. Du and D. Wang, Angew. Chem. Int. Ed., 2011, 50, 2738-2741.

H. Chen, J. He, H. Tang and C. Yan, Chem. Mater., 2008, 20, 5894-5900.

H. Wu, G. Liu, S. Zhang, J. Shi, L. Zhang, Y. Chen, F. Chen and H. Chen, J. Mater. Chem., 2011, 21, 3037-3045.

Z. Xu, Y. Cao, C. Li, P. a. Ma, X. Zhai, S. Huang, X. Kang, M. Shang, D. Yang, Y. Dai and J. Lin, J. Mater. Chem., 2011, 21, 3686-3694.

Y. Zhu, J. Shi, W. Shen, X. Dong, J. Feng, M. Ruan and Y. Li, Angew. Chem. Int. Ed., 2005, 44, 5083-5087.

G. Zhang, L. Yu, H. B. Wu, H. E. Hoster and X. W. Lou, Adv. Mater., 2012, 24, 4609-4613.

X. W. Lou, Y. Wang, C. Yuan, J. Y. Lee and L. A. Archer, Adv. Mater., 2006, 18, 2325-2329.

L. Jin, L. Xu, C. Morein, C.-h. Chen, M. Lai, S. Dharmarathna, A. Dobley and S. L. Suib, Adv. Funct. Mater., 2010, 20, 3373-3382.

Z. Dong, X. Lai, J. E. Halpert, N. Yang, L. Yi, J. Zhai, D. Wang, Z. Tang and L. Jiang, Adv. Mater., 2012, 24, 1046-1049.

K. Saravanan, H. S. Lee, M. Kuezma, J. J. Vittal and P. Balaya, J. Mater. Chem., 2011, 21, 10042-10050.

X. Lai, J. E. Halpert and D. Wang, Energy Environ. Sci., 2012, 5, 5604-5618.

L. Zhou, D. Zhao and X. W. Lou, Adv. Mater., 2012, 24, 745-748.

Y. Wang, B. Sunkara, J. Zhan, J. He, L. Miao, G. L. McPherson, V. T. John and L. Spinu, Langmuir, 2012, 28, 13783-13787.

X. Wang, X.-L. Wu, Y.-G. Guo, Y. Zhong, X. Cao, Y. Ma and J. Yao, Adv. Funct. Mater., 2010, 20, 1680-1686.

K. Zhang, H. Chen, Y. Zheng, Y. Chen, M. Ma, X. Wang, L. Wang, D. Zeng and J. Shi, J. Mater. Chem., 2012, 22, 12553-12561.

J. Liu, H. Q. Yang, F. Kleitz, Z. G. Chen, T. Yang, E. Strounina, G. Q. Lu and S. Z. Qiao, Adv. Funct. Mater., 2012, 22, 591-599.

J. Gao, G. Liang, B. Zhang, Y. Kuang, X. Zhang and B. Xu, J. Am. Chem. Soc., 2007, 129, 1428-1433.

J. Liu, S. Z. Qiao, J. S. Chen, X. W. Lou, X. Xing and G. Q. Lu, Chem. Commun., 2011, 47, 12578-12591.

H. J. Lee, W. Cho and M. Oh, Chem. Commun., 2012, 48, 221-223.

J. Liu, Y. Deng, C. Liu, Z. Sun and D. Zhao, J. Colloid Interface Sci., 2009, 333, 329-334.

Tissot, J. P. Reymond, F. Lefebvre and E. Bourgeat-Lami, Chem. Mater., 2002, 14, 1325-1331.

X. W. Lou, C. Yuan, E. Rhoades, Q. Zhang and L. A. Archer, Adv. Funct. Mater., 2006, 16, 1679-1684.

S.-H. Wu, C.-T. Tseng, Y.-S. Lin, C.-H. Lin, Y. Hung and C.-Y. Mou, J. Mater. Chem., 2011, 21, 789-794.

J. Yuan, X. Bai, M. Zhao and L. Zheng, Langmuir, 2010, 26, 11726-11731.

C. I. Zoldesi and A. Imhof, Adv. Mater., 2005, 17, 924-928.

S. Hyuk Im, U. Jeong and Y. Xia, Nat. Mater., 2005, 4, 671-675.

Y. Jing, Y. Zhu, X. Yang, J. Shen and C. Li, Langmuir, 2010, 27, 1175-1180.

H. J. Kim, H. Matsuda, H. Zhou and I. Honma, Adv. Mater., 2006, 18, 3083-3088.

Y. Lu, H. Fan, A. Stump, T. L. Ward, T. Rieker and C. J. Brinker, Nature, 1999, 398, 223-226.

T. Zheng, J. Pang, G. Tan, J. He, G. L. McPherson, Y. Lu, V. T. John and J. Zhan, Langmuir, 2007, 23, 5143-5147.

S. Brunauer, L. S. Deming, W. E. Deming and E. Teller, J. Am. Chem. Soc., 1940, 62, 1723-1732.

E. B. Flint and K. S. Suslick, Science, 1991, 253, 1397-1399.

The invention claimed is:

1. A method of forming amphiphilic nanoparticles having a bilayer comprising a hydrophilic, ceramic-containing outer layer and a hydrophobic, carbon-containing inner layer surrounding a hollow core, and iron oxide nanoparticles located within the bilayer and/or hollow core, comprising the steps of:
   a) atomizing a solution comprising a ceramic precursor, a carbon precursor comprising a saccharide, a metal salt, and a templating surfactant into aerosol droplets, wherein the metal salt comprises an iron salt;
   b) heating the aerosol droplets to form particles comprising a hydrophilic, ceramic-containing outer layer derived from the ceramic precursor and a core containing the carbon precursor and the templating surfactant, wherein the metal salt is located within the shell and/or the core; and
   c) pyrolyzing the particles, thereby generating internal pressure, which pushes the carbon precursor to the inner surface of the hydrophilic, ceramic-containing outer layer to form a hydrophobic, carbon-containing inner layer derived from the carbon precursor, a hollow core, and metal oxide nanoparticles derived from the metal salt, wherein the metal oxide nanoparticles comprise iron oxide and are located within the hydrophilic, ceramic-containing outer layer, the hydrophobic, carbon-containing inner layer, and/or hollow core, thereby forming the amphiphilic nanoparticles having a bilayer comprising a hydrophilic ceramic-containing outer layer and a hydrophobic carbon-containing inner layer surrounding a hollow core, and iron oxide nanoparticles located within the bilayer and/or hollow core, wherein the hydrophilic, ceramic-containing outer layer is in the form of a non-mesoporous dense, low-porosity shell.

2. The method of claim 1, wherein the ceramic precursor includes silica, titania, zirconia, alumina, yttria, ceria, or mixtures thereof.

3. The method of claim 1, wherein the metal salt further comprises palladium, chromium, zinc, rhodium, ruthenium, molybdenum, or mixtures thereof.

4. The method of claim 1, wherein the saccharide comprises a monosaccharide, a polysaccharide, or mixtures thereof.

5. The method of claim 1, wherein the templating surfactant is cetyltrimethyl ammonium bromide (CTAB), cetyltrimethyl ammonium chloride (CTAC), cetyltrimethyl ammonium iodide (CTAI), cetyltrimethyl ammonium fluoride (CTAF), cetyltrimethyl ammonium astatide (CTAA), or mixtures thereof.

6. The method of claim 1, further comprising the step of:
   d) etching the amphiphilic nanoparticles, thereby removing the hydrophilic, ceramic-containing outer layer of the bilayer; or
   d) calcining the amphiphilic nanoparticles, thereby removing the hydrophobic, carbon-containing inner layer of the bilayer.

7. The method of claim 1, wherein the hydrophobic, carbon-containing inner layer has an average thickness ranging from 5 nm to 100 nm and/or the hydrophilic, ceramic-containing outer layer has an average thickness ranging from 5 nm to 100 nm.

8. The method of claim 1, wherein the amphiphilic nanoparticles have an average Brunauer-Emmet-Teller surface area ranging from 12.5 $m^2$/g to 372 $m^2$/g.

9. The method of claim 1 further comprising the step of:
   d) loading a compound into the core.

10. The method of claim 1, wherein at least one of the amphiphilic nanoparticles has a protrusion extending from the bilayer.

11. The method of claim 1, wherein the amphiphilic nanoparticles comprise pores having an average Barret-Joyner-Halenda desorption pore volume ranging from 0.0279 $cm^3$/g to 0.162 $cm^3$/g.

12. The method of claim 1, wherein the solution has an iron salt to ceramic precursor molar ratio ranging from 1:13 to 1:2.7.

13. The method claim 12, wherein the solution further comprises sodium chloride such that the solution has a sodium to iron molar ratio ranging from 0.6:1 to 2:1.

14. The method of claim 2, wherein the ceramic precursor comprises silica, titania, or a combination thereof.

15. The method of claim 14, wherein the ceramic precursor is tetraethyl orthosilicate (TEOS), titania isopropoxide, or a combination thereof.

16. The method of claim 1, wherein the iron salt is iron chloride.

17. The method of claim 4, wherein the saccharide comprises sucrose, glucose, cellulose, cyclodextrin, or mixtures thereof.

18. The method of claim 17, wherein the saccharide is sucrose.

19. The method of claim 5, wherein the templating surfactant is cetyltrimethyl ammonium bromide (CTAB).

20. The method of claim 1, wherein the amphiphilic nanoparticles have an average Brunauer-Emmet-Teller surface area ranging from 12.5 $m^2/g$ to 33.3 $m^2/g$.

* * * * *